(12) United States Patent
Haseba et al.

(10) Patent No.: US 10,308,870 B2
(45) Date of Patent: *Jun. 4, 2019

(54) LIQUID CRYSTAL MEDIUM, OPTICAL DEVICE AND LIQUID CRYSTAL COMPOUND

(71) Applicants: JNC CORPORATION, Tokyo (JP); JNC PETROCHEMICAL CORPORATION, Tokyo (JP)

(72) Inventors: Yasuhiro Haseba, Chiba (JP); Koki Sago, Chiba (JP); Shinichi Yamamoto, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/100,979

(22) PCT Filed: Dec. 4, 2014

(86) PCT No.: PCT/JP2014/082134
§ 371 (c)(1),
(2) Date: Jun. 1, 2016

(87) PCT Pub. No.: WO2015/087778
PCT Pub. Date: Jun. 18, 2015

(65) Prior Publication Data
US 2016/0304784 A1    Oct. 20, 2016

(30) Foreign Application Priority Data

Dec. 10, 2013 (JP) ................................. 2013-254837

(51) Int. Cl.
*C09K 19/20* (2006.01)
*C09K 19/34* (2006.01)
(Continued)

(52) U.S. Cl.
CPC ........ *C09K 19/3402* (2013.01); *C07C 43/225* (2013.01); *C09K 19/20* (2013.01);
(Continued)

(58) Field of Classification Search
CPC .................................................. C09K 19/586
See application file for complete search history.

(56) References Cited

U.S. PATENT DOCUMENTS 6,329,027 B1    12/2001   Kondo et al.
9,458,125 B2 *  10/2016   Sago ..................... C07D 319/06
(Continued)

FOREIGN PATENT DOCUMENTS

CN        100487545       5/2009
CN        102666785       9/2012
(Continued)

OTHER PUBLICATIONS

Hirotsugu Kikuchi, et al., "Polymer-stabilized liquid crystal blue phases," Nature Materials, vol. 1, Sep. 2002, pp. 64-68.
(Continued)

*Primary Examiner* — Chanceity N Robinson
(74) *Attorney, Agent, or Firm* — JCIPRNET

(57) ABSTRACT

A liquid crystal medium that has stability to heat, light and so forth, a wide temperature range of a liquid crystal phase and significantly large dielectric anisotropy to develop an optically isotropic liquid crystal phase is required. Moreover, various optical devices that can be used in a wide temperature range, and have a short response time, a large contrast ratio and a low drive voltage are required. A liquid crystal composition contains an achiral component T containing at least one compound (1) represented by formula (1) and a chiral agent to develop an optically isotropic liquid crystal phase, wherein in formula (1), $R^1$ is alkyl having 1 to
(Continued)

12 carbons, $L^1$, $L^2$ and $L^3$ are each independently hydrogen, fluorine or chlorine; and $Y^1$ is fluorine, $CF_3$, or $-OCF_3$.

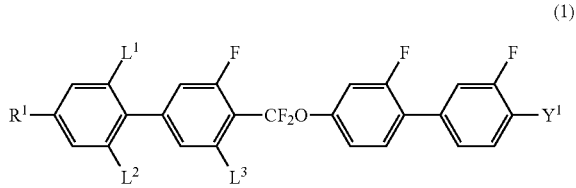

(1)

12 Claims, 3 Drawing Sheets

(51) Int. Cl.
  *C09K 19/58*   (2006.01)
  *C07C 43/225*   (2006.01)
  *C09K 19/56*   (2006.01)
  *C09K 19/04*   (2006.01)
  *G02F 1/1343*   (2006.01)

(52) U.S. Cl.
  CPC ...... *C09K 19/3444* (2013.01); *C09K 19/3458* (2013.01); *C09K 19/56* (2013.01); *C09K 19/586* (2013.01); *C09K 19/588* (2013.01); *C09K 2019/0466* (2013.01); *C09K 2019/3422* (2013.01); *G02F 1/134309* (2013.01)

(56) References Cited

U.S. PATENT DOCUMENTS

| | | | |
|---|---|---|---|
| 9,487,701 | B2 | 11/2016 | Hattori et al. |
| 2006/0006363 | A1 | 1/2006 | Heckmeier et al. |
| 2006/0050354 | A1 | 3/2006 | Heckmeier et al. |
| 2006/0227283 | A1 | 10/2006 | Ooi et al. |
| 2008/0259254 | A1 | 10/2008 | Kikuchi et al. |
| 2011/0242473 | A1* | 10/2011 | Haseba .................. C09K 19/20 349/139 |
| 2016/0257882 | A1 | 9/2016 | Furusato et al. |

FOREIGN PATENT DOCUMENTS

| | | | |
|---|---|---|---|
| CN | 105637066 | 6/2016 | |
| EP | 1690917 | 8/2006 | |
| JP | 2003327966 | 11/2003 | |
| JP | 2005157109 | 6/2005 | |
| JP | 2005336477 | 12/2005 | |
| JP | 2006506477 | 2/2006 | |
| JP | 2006506515 | 2/2006 | |
| JP | 2006089622 | 4/2006 | |
| JP | 2006127707 | 5/2006 | |
| JP | 2006225655 | 8/2006 | |
| JP | 2006299084 | 11/2006 | |
| JP | WO 2010058681 A1 * | 5/2010 | ............. C09K 19/20 |
| WO | 9823561 | 6/1998 | |
| WO | 2005080529 | 9/2005 | |
| WO | 2005090520 | 9/2005 | |
| WO | 2006063662 | 6/2006 | |
| WO | 2010058681 | 5/2010 | |
| WO | WO-2014097952 A1 * | 6/2014 | ........... C07D 319/06 |

OTHER PUBLICATIONS

Yoshiaki Hisakado., et al., "Large Electro-optic Kerr Effect in Polymer-Stabilized Liquid-Crystalline Blue Phases," Advanced Materials, vol. 17, No. 1, Jan. 6, 2005, pp. 96-98.

Yasuhiro Haseba, et al., "Electro-optic effects of the optically isotropic state induced by the incorporative effects of a polymer network and the chirality of liquid crystal," Journal of the Society for Information Display, vol. 14, Issue 6, Jun. 2006, pp. 551-556.

"International Search Report (Form PCT/ISA/210) of PCT/JP2014/082134", dated Feb. 3, 2015, with English translation thereof, pp. 1-4.

"Office Action of China Counterpart Applciation," with machine English translation thereof, dated Sep. 22, 2017, p. 1-p. 14, in which the listed references were cited.

"Office Action of Taiwan Counterpart Application," dated Feb. 12, 2018, with English translation thereof, pp. 1-13.

"Office Action of China Counterpart Application," dated Apr. 17, 2018, with English translation thereof, p. 1-p. 12.

"Office Action of Taiwan Counterpart Application," dated Oct. 9, 2018, with English translation thereof, p. 1-p. 10.

* cited by examiner

Optical system for measurement
(use of comb electrode cell)

LIQUID CRYSTAL MEDIUM, OPTICAL DEVICE AND LIQUID CRYSTAL COMPOUND

CROSS-REFERENCE TO RELATED APPLICATION

This application is a 371 application of the international PCT application serial no. PCT/JP2014/082134, filed on Dec. 4, 2014, which claims the priority benefit of Japan application no. 2013-254837, filed on Dec. 10, 2013. The entirety of each of the above-mentioned patent applications is hereby incorporated by reference herein and made a part of this specification.

TECHNICAL FIELD

The invention relates to a liquid crystal compound useful, for example, as an optical device material, a liquid crystal composition and an optical device in which the liquid crystal composition is used, and so forth.

BACKGROUND ART

A liquid crystal display device in which a liquid crystal composition is used is widely used for a display of a watch, a calculator, a cellular phone, a personal computer, a television receiver and so forth. The liquid crystal display devices utilize refractive index anisotropy or dielectric anisotropy of a liquid crystal compound, or the like. As an operating mode of the liquid crystal display device, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode or the like is known, in which one or more polarizing plates are mainly used. Further, a research has been recently conducted into a mode in which an electric field is applied thereto in an optically isotropic liquid crystal phase to develop electric birefringence (Patent literature Nos. 1 to 15, Non-patent literature Nos. 1 to 3).

Further, a proposal has been made on a wavelength variable filter, a wavefront control device, a liquid crystal lens, an aberration correction device, an aperture control device, an optical head device or the like utilizing electric birefringence in a blue phase being one of optically isotropic liquid crystal phases (Patent literature Nos. 10 to 12).

A classification based on a driving mode in the device includes a passive matrix (PM) and an active matrix (AM). The passive matrix (PM) is classified into static, multiplex and so forth, and the AM is classified into a thin film transistor (TFT), a metal insulator metal (MIM) and so forth according to a kind of a switching device thereof.

As a liquid crystal composition used for a liquid crystal display device, Patent literature No. 14 includes an example of reporting an optically isotropic liquid crystal composition containing a compound having two biphenyl groups and a difluoromethoxy linking group. However, although the liquid crystal composition disclosed in Patent literature No. 14 exhibits a large dielectric anisotropy and is effective in reducing a drive voltage of a display, the composition has had an issue of a large temperature dependence of the drive voltage in a temperature range centering on an operating temperature.

Compound (1) of the present application has features of having two biphenyl groups and a difluoromethoxy linking group, and an optically isotropic liquid crystal composition containing compound (1) of the present application has features of small temperature dependence of the drive voltage in the temperature range centering on the operating temperature. No description of the temperature dependence of drive voltage is found in Patent literature No. 14. An effect of minimizing the temperature dependence of the drive voltage is a finding that has been found out for the first time according to the instant invention.

CITATION LIST

Patent Literature

Patent literature No. 1: JP 2003-327966 A.
Patent literature No. 2: WO 2005/90520 A.
Patent literature No. 3: JP 2005-336477 A.
Patent literature No. 4: JP 2006-89622 A.
Patent literature No. 5: JP 2006-299084 A.
Patent literature No. 6: JP 2006-506477 A.
Patent literature No. 7: JP 2006-506515 A.
Patent literature No. 8: WO 2006/063662 A.
Patent literature No. 9: JP 2006-225655 A.
Patent literature No. 10: JP 2005-157109 A.
Patent literature No. 11: WO 2005/80529 A.
Patent literature No. 12: JP 2006-127707 A.
Patent literature No. 13: WO 1998/023561 A.
Patent literature No. 14: WO 2010/058681 A.

Non-Patent Literature

Non-patent literature NO. 1: Nature Materials, 1, 64, (2002)
Non-patent literature NO. 2: Adv. Mater., 17, 96, (2005)
Non-patent literature NO. 3: Journal of the SID, 14, 551 (2006)

SUMMARY OF INVENTION

Technical Problem

Under the situations described above, a liquid crystal medium that has stability to heat, light and so forth, a wide liquid crystal phase temperature range and a significantly large dielectric anisotropy and develops an optically isotropic liquid crystal phase is required. Moreover, an optical device or the like that can be used in a wide temperature range, and has a short response time, a large contrast ratio and a low drive voltage, and a small temperature dependence of drive voltage in a temperature range centering on an operating temperature is required.

Solution to Problem

The invention provides, for example, a liquid crystal compound, a liquid crystal medium (a liquid crystal composition, a polymer/liquid crystal composite material), a mixture of a polymerizable monomer and the liquid crystal composition, and an optical device including the liquid crystal medium as described below.

Item 1. A liquid crystal composition that contains an achiral component T containing at least one compound (1) represented by formula (1) and a chiral agent to develop an optically isotropic liquid crystal phase:

(1)

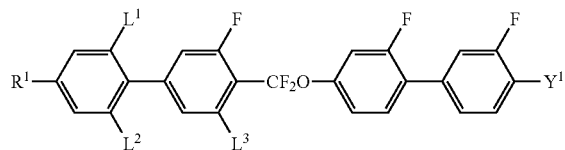

(wherein, in formula (1), $R^1$ is hydrogen, alkyl having 1 to 12 carbons, alkenyl having 2 to 12 carbons, alkynyl having 2 to 12 carbons or alkoxy having 1 to 11 carbons; $L^1$, $L^2$ and $L^3$ are each independently hydrogen, fluorine or chlorine; and $Y^1$ is fluorine, chlorine, —$CF_3$ or —$OCF_3$.)

Item 2. The liquid crystal composition according to item 1, containing the achiral component T containing at least one compound represented by any one of formulas (1-1) to (1-12) and the chiral agent to develop the optically isotropic liquid crystal phase:

(1-1)

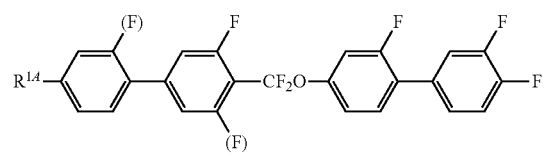

(1-2)

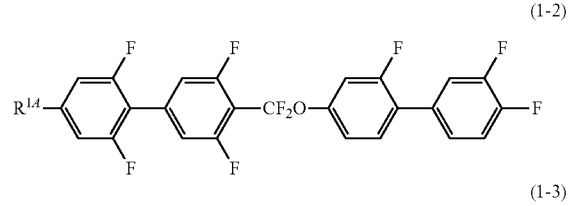

(1-3)

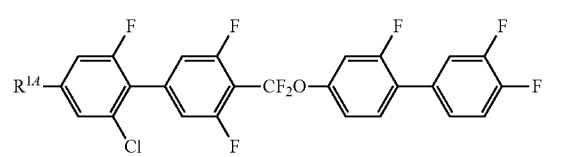

(1-4)

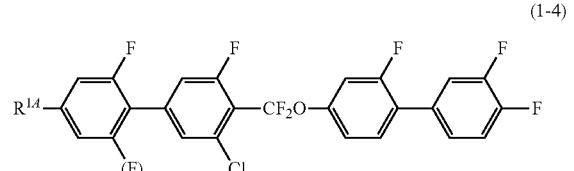

(1-5)

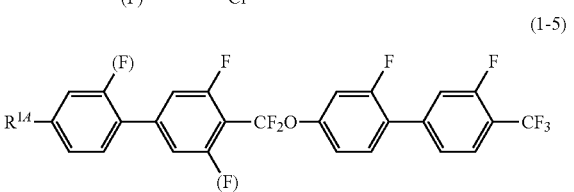

(1-6)

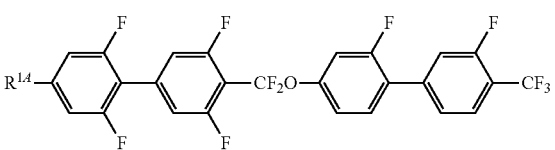

(1-7)

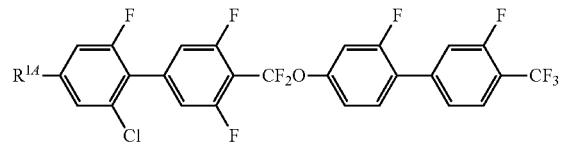

(1-8)

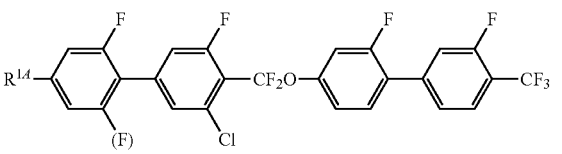

(1-9)

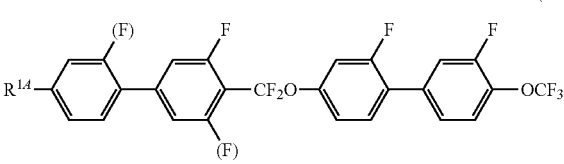

(1-10)

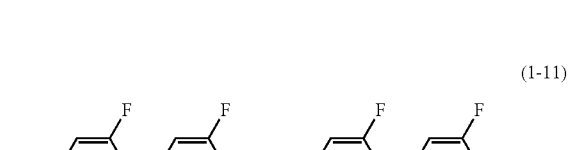

(1-11)

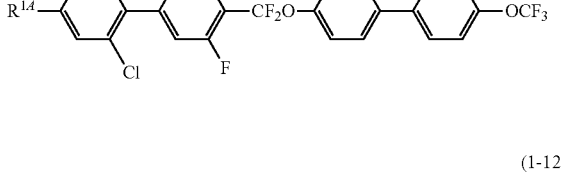

(1-12)

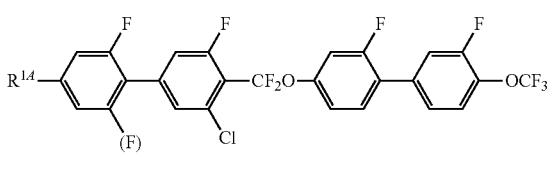

(wherein, in the formulas described above, $R^{14}$ is each independently hydrogen, alkyl having 1 to 12 carbons or alkenyl having 2 to 12 carbons; and (F) is each independently hydrogen or fluorine.).

Item 3. The liquid crystal composition according to item 1 or 2, further containing at least one of compound (3) represented by formula (3) or compound (7) represented by formula (7) as a second component of the achiral component T:

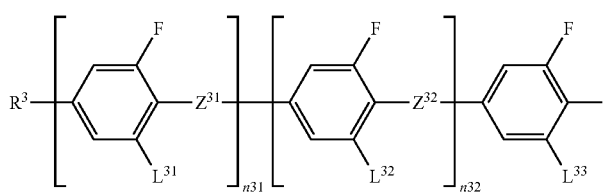 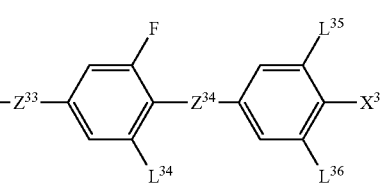

(3)

(wherein, in formula (3), $R^3$ is hydrogen or alkyl having 1 to 12 carbons, at least one piece of —$CH_2$— in $R^3$ may be replaced by —O—, —S—, —COO— or —OCO—, at least one piece of —$CH_2$—$CH_2$— in $R^3$ may be replaced by —CH=CH—, —CF=CF— or —C≡C—, and at least one piece of hydrogen in $R^3$ may be replaced by fluorine or chlorine, however, in $R^3$, a case where —O— and —CH=CH— are adjacent is excluded, and a case where —CO— and —CH=CH— are adjacent is excluded;

$Z^{31}$, $Z^{32}$, $Z^{33}$ and $Z^{34}$ are each independently a single bond or alkylene having 1 to 4 carbons, and at least one piece of —$CH_2$— in the alkylene may be replaced by —O—, —COO— or —$CF_2$O—;

$L^{31}$, $L^{32}$, $L^{33}$, $L^{34}$, $L^{35}$ and $L^{36}$ are each independently hydrogen or fluorine;

$X^3$ is hydrogen, halogen, —$SF_5$ or alkyl having 1 to 10 carbons, at least one piece of —$CH_2$— in $X^3$ may be replaced by —O—, —S—, —COO— or —OCO—, at least one piece of —$CH_2$—$CH_2$— in $X^3$ may be replaced by —CH=CH—, —CF=CF— or —C≡C—, and at least one piece of hydrogen in $X^3$ may be replaced by fluorine or chlorine, however, in $X^3$, a case where —O— and —CH=CH— are adjacent is excluded, and a case where —CO— and —CH=CH— are adjacent is excluded;

n31 and n32 are each independently 0 or 1;

however, when n31+n32=1 and $Z^{33}$ is $CF_2O$, both $L^{35}$ and $L^{36}$ are fluorine);

n71 and n72 are each independently 0 or 1; and $X^7$ is hydrogen, halogen, —$SF_5$ or alkyl having 1 to 10 carbons, at least one piece of —$CH_2$— in $X^7$ may be replaced by —O—, —S—, —COO— or —OCO—, at least one piece of —$CH_2$—$CH_2$— in $X^7$ may be replaced by —CH=CH—, —CF=CF— or —C≡C—, and at least one piece of hydrogen in $X^7$ may be replaced by fluorine or chlorine, however, in the alkyl, a case where —O— and —CH=CH— are adjacent is excluded, and a case where —CO— and —CH=CH— are adjacent is excluded.).

Item 4. The liquid crystal composition according to item 3, wherein compound (3) is a compound represented by any one of formula (3-2) or (3-3):

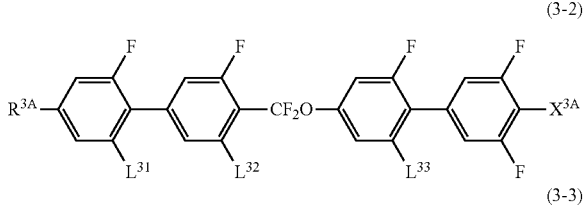

(3-2)

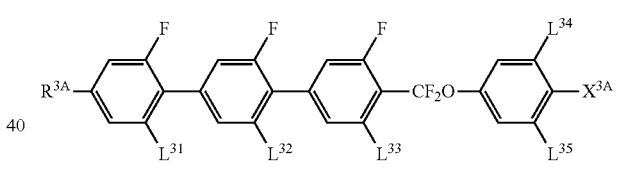

(3-3)

(7)

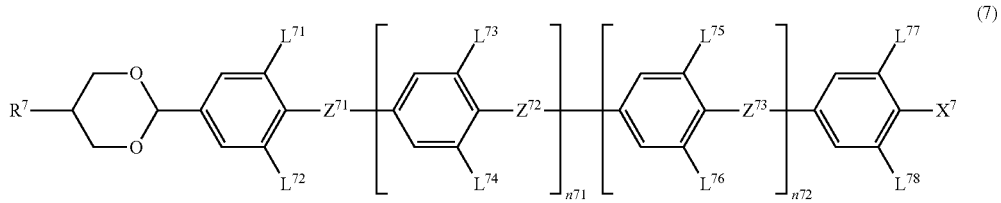

(wherein, in formula (7), $R^7$ is hydrogen or alkyl having 1 to 12 carbons, at least one piece of —$CH_2$— in $R^7$ may be replaced by —O—, —S—, —COO— or —OCO—, at least one piece of —$CH_2$—$CH_2$— in $R^7$ may be replaced by —CH=CH—, —CF=CF— or —C≡C—, and at least one piece of hydrogen in $R^7$ may be replaced by fluorine or chlorine, however, in $R^7$, a case where —O— and —CH=CH— are adjacent is excluded, and a case where —CO— and —CH=CH— are adjacent is excluded;

$L^{71}$, $L^{72}$, $L^{73}$, $L^{74}$, $L^{75}$, $L^{76}$, $L^{77}$ and $L^{78}$ are each independently hydrogen or fluorine;

$Z^{71}$, $Z^{72}$ and $Z^{73}$ are each independently a single bond, —COO— or —$CF_2$O—;

(wherein, in the formula, $R^{3A}$ is each independently alkyl having 1 to 12 carbons, alkenyl having 2 to 12 carbons or alkoxy having 1 to 11 carbons;

$L^{31}$, $L^{32}$, $L^{33}$, $L^{34}$ and $L^{35}$ are each independently hydrogen or fluorine; and $X^{3A}$ is fluorine, chlorine, —$CF_3$ or —$OCF_3$.)

Item 5. The liquid crystal composition according to item 3, wherein compound (7) is a compound represented by any one of formulas (7-1) to (7-8):

(7-1)
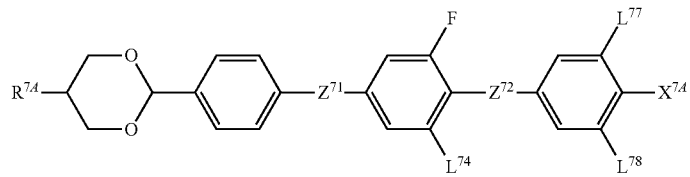
(7-2)
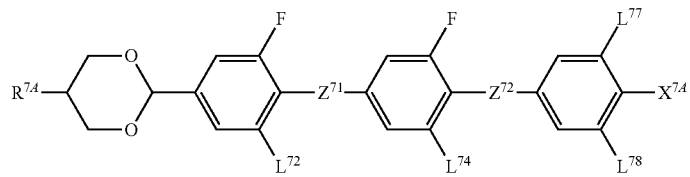
(7-3)
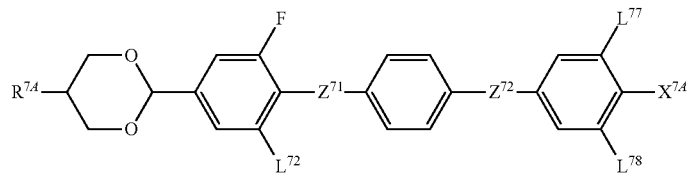
(7-4)
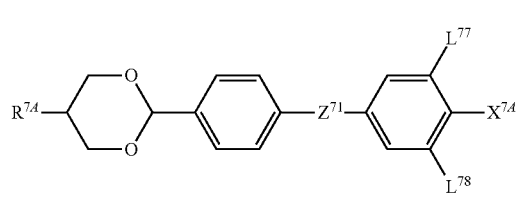
(7-5)
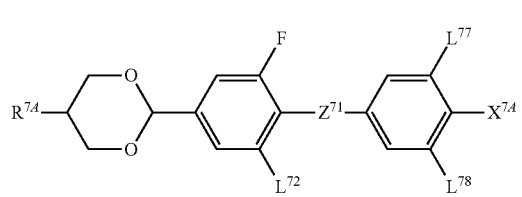
(7-6)
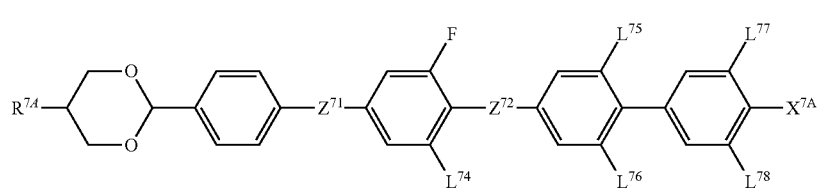
(7-7)
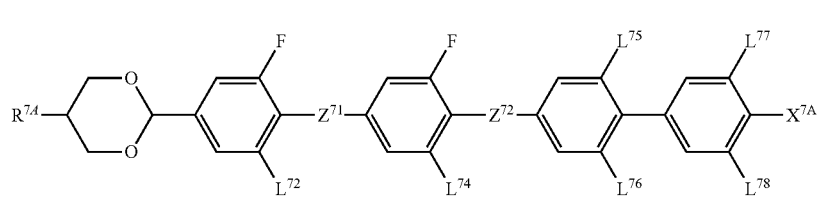
(7-8)
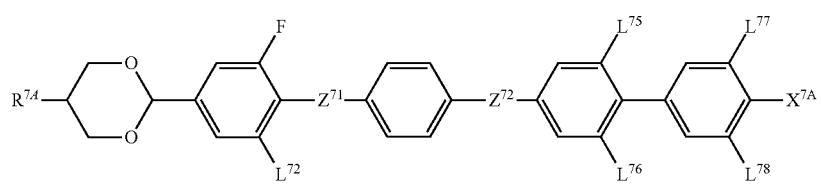

(wherein, in the formula, $R^{74}$ is each independently hydrogen, alkyl having 1 to 12 carbons or alkenyl having 2 to 12 carbons or alkoxy having 1 to 11 carbons;

$L^{72}$, $L^{74}$, $L^{75}$, $L^{76}$, $L^{77}$ and $L^{78}$ are each independently hydrogen or fluorine;

$X^{74}$ is each independently fluorine, chlorine, —$CF_3$ or —$OCF_3$, and $Z^{71}$ and $Z^{72}$ are each independently a single bond, —COO— or —$CF_2O$—, but at least one thereof is —COO— or —$CF_2O$—.)

Item 6. The liquid crystal composition according to item 3, wherein compound (7) is a compound represented by any one of formulas (7-2-2-E), (7-2-5-E), (7-2-7-E), (7-2-2-F), (7-2-5-F), (7-2-6-F) or (7-2-7-F):

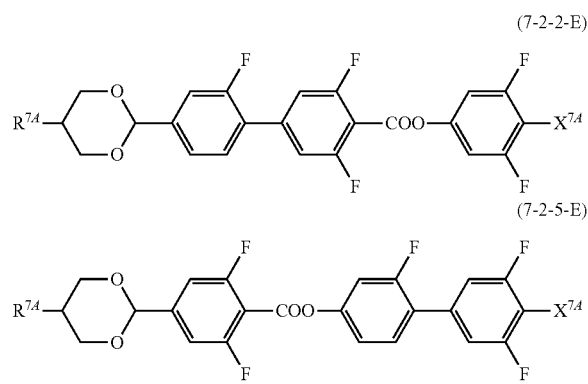

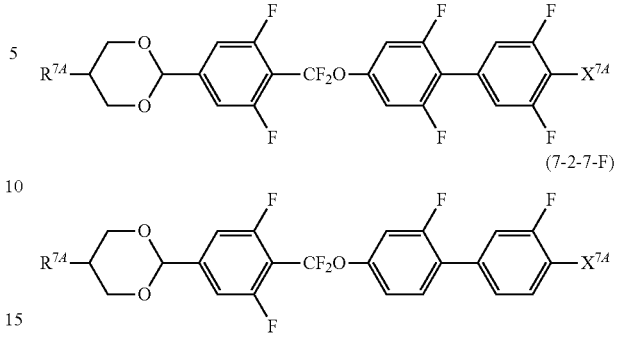

(wherein, in the formula, $R^{74}$ is each independently alkyl having 1 to 12 carbons, alkenyl having 2 to 12 carbons or alkoxy having 1 to 11 carbons; and $X^{74}$ is fluorine, chlorine, —$CF_3$ or —$OCF_3$.)

Item 7. The liquid crystal composition according to any one of items 3 to 6, containing 10% by weight to 30% by weight of compound (1) in total, 20% by weight to 60% by weight of compound (3) in total and 30% by weight to 70% by weight of compound (7) in total, based on the total weight of the achiral component T.

Item 8. The liquid crystal composition according to any one of items 1 to 7, further containing at least one of compound (4) represented by formula (4) and compound (2) represented by formula (2) as a third component of the achiral component T;

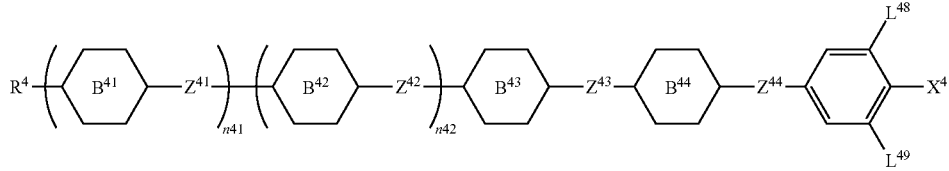

-continued

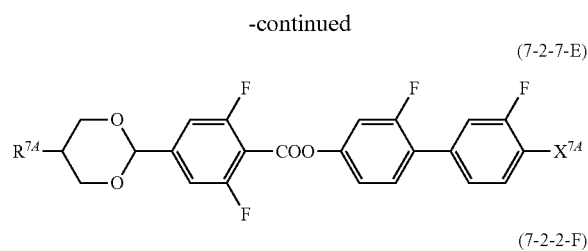

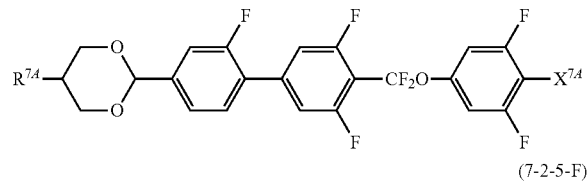

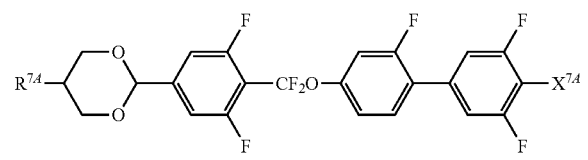

(wherein, in formula (4), $R^4$ is alkyl having 1 to 12 carbons, alkenyl having 2 to 12 carbons, or alkoxy having 1 to 11 carbons;

$B^{41}$, $B^{42}$, $B^{43}$ and $B^{44}$ are each independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine 2,5-diyl;

$Z^{41}$, $Z^{42}$, $Z^{43}$ and $Z^{44}$ are each independently a single bond, ethylene, —COO—, —OCO—, —$CF_2O$— or —$OCF_2$—;

$L^{48}$ and $L^{49}$ are each independently hydrogen or fluorine;

$X^4$ is fluorine, chlorine, —$CF_3$ or —$OCF_3$;

n41 and n42 are each independently 0 or 1;

however, a case where all of $B^{41}$, $B^{42}$, $B^{43}$ and $B^{44}$ are 1,4-phenylene replaced by fluorine is excluded; and when n41+n42=1 and $Z^{43}$ is —$CF_2O$—, both $L^{48}$ and $L^{49}$ are fluorine);

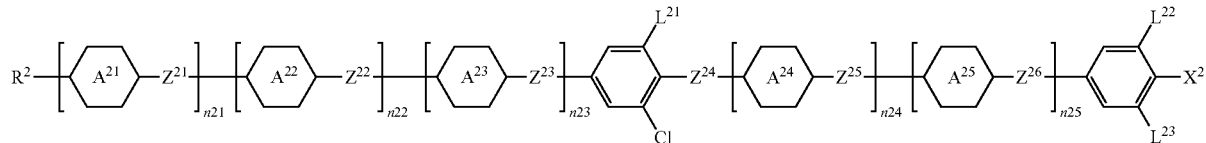

(2)

(wherein, in formula (2), $R^2$ is hydrogen or alkyl having 1 to 12 carbons, at least one piece of —$CH_2$— in $R^2$ may be replaced by —O—, —S—, —COO—, —OCO—, —CH=CH—, —CF=CF— or —C≡C—, and at least one piece of hydrogen in $R^2$ may be replaced by halogen or alkyl having 1 to 3 carbons;

however, in $R^2$, a case where —O— and —CH=CH— are adjacent is excluded, and a case where —CO— and —CH=CH— are adjacent is excluded;

$A^{21}$, $A^{22}$, $A^{23}$, $A^{24}$ and $A^{25}$ are each independently 1,4-cyclohexylene, 1,3-dioxane-2,5-diyl, 1,4-phenylene, 1,4-phenylene in which one or two pieces of hydrogen are replaced by fluorine, 1,4-phenylene in which two pieces of hydrogen are each replaced by fluorine and chlorine, pyridine-2,5-diyl or pyrimidine-2,5-diyl;

$Z^{21}$, $Z^{22}$, $Z^{23}$, $Z^{24}$, $Z^{25}$ and $Z^{26}$ are each independently a single bond or alkylene having 1 to 4 carbons, and at least one piece of —$CH_2$— in the alkylene may be replaced by —O—, —COO— or —$CF_2$O—;

$L^{21}$, $L^{22}$ and $L^{23}$ are each independently hydrogen or fluorine;

$X^2$ is fluorine, chlorine, —$CF_3$ or —$OCF_3$;

n21, n22, n23, n24 and n25 are each independently 0 or 1, and an expression: $2 \leq n21+n22+n23+n24+n25 \leq 3$ holds, however, when n21+n22+n23+n24+n25=2, both $L^{22}$ and $L^{23}$ are fluorine.)

Item 9. The liquid crystal composition according to item 8, wherein compound (4) is a compound represented by any one of formulas (4-1) to (4-9):

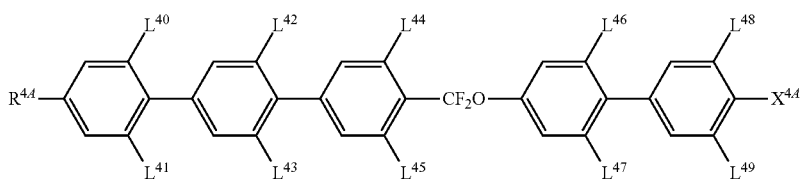

(4-1)

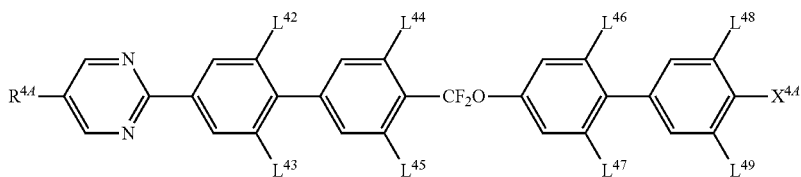

(4-2)

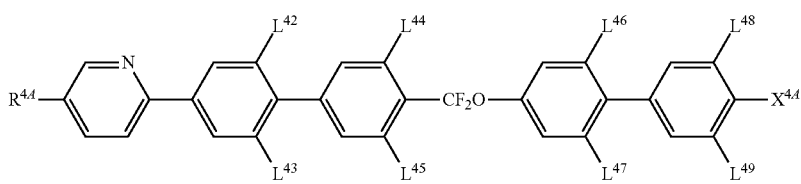

(4-3)

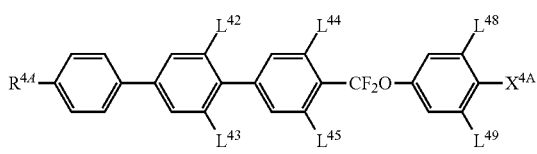

(4-4)

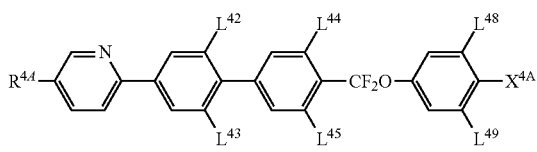

(4-6)

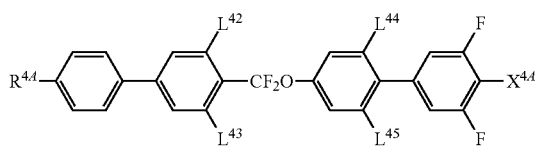

(4-7)

(4-5)

-continued (4-8)
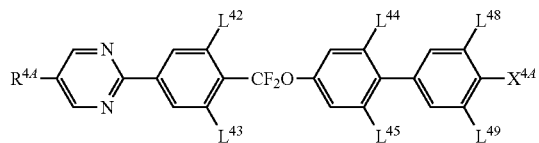

(4-9)
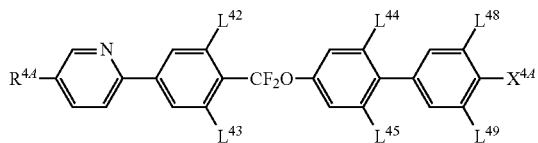

(wherein, in the formulas, $R^{4A}$ is each independently alkyl having 1 having 12 carbons, alkenyl having 2 to 12 carbons or alkoxy having 1 to 11 carbons;

$X^{4A}$ is fluorine, chlorine, —$CF_3$ or —$OCF_3$; and $L^{40}$ to $L^{49}$ are each independently hydrogen or fluorine.

Item 10. The liquid crystal composition according to item 8, wherein compound (2) is a compound represented by any one of formulas (2-1-1-2), (2-1-2-1), (2-1-3-1), (2-1-3-2), (2-1-4-2) or (2-1-4-3):

(wherein, in the formula, $R^{2A}$ is each independently alkyl having 1 to 12 carbons, alkenyl having 2 to 12 carbons or alkoxy having 1 to 11 carbons;

(F) is each independently hydrogen or fluorine; and $X^{2A}$ is fluorine, chlorine, —$CF_3$ or —$OCF_3$.)

Item 11. The liquid crystal composition according to any one of Items 1 to 10, wherein the chiral agent is any one of compounds (K1) to (K7) represented by formulas (K1) to (K7):

(2-1-1-2)
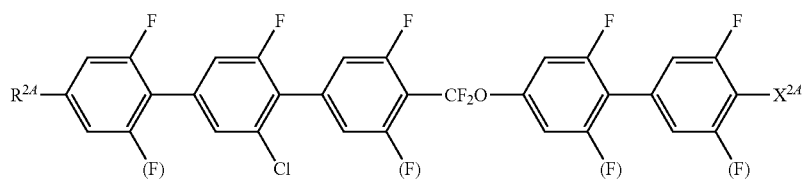

(2-1-2-1)
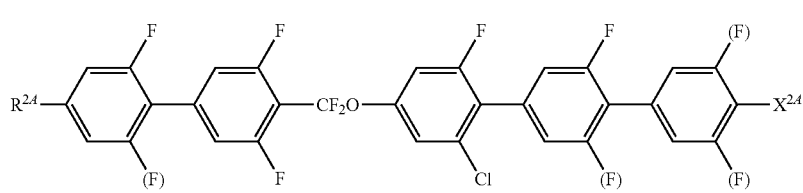

(2-1-3-1)
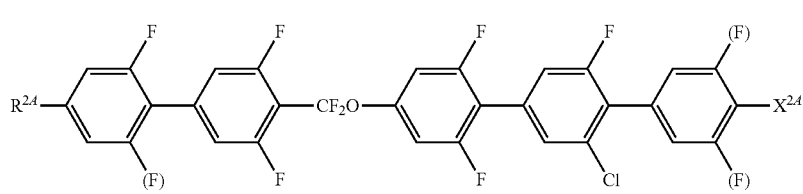

(2-1-3-2)
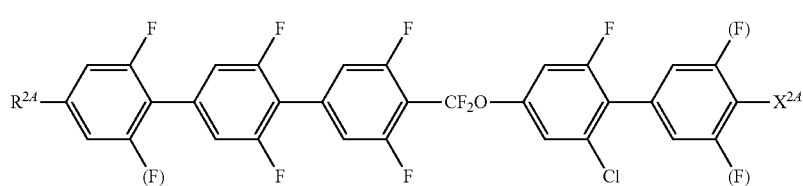

(2-1-4-2)
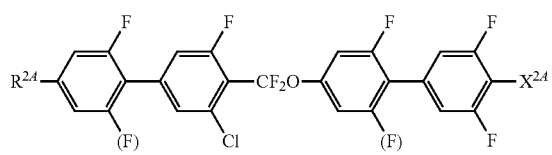

(2-1-4-3)
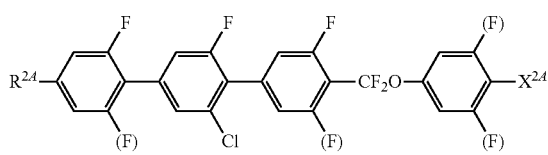

(K1) 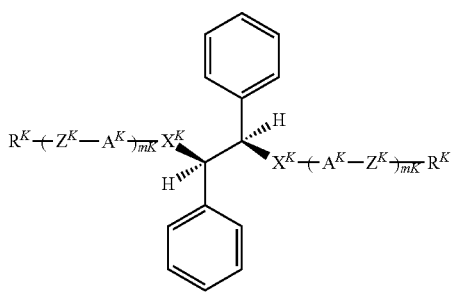

(K2) 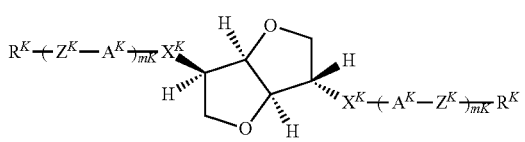

(K3) 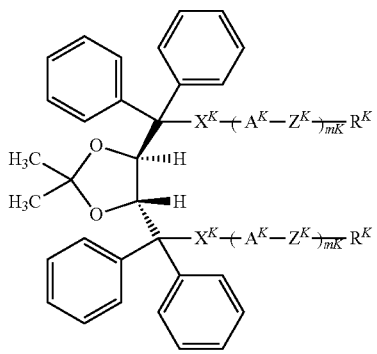

(K4) 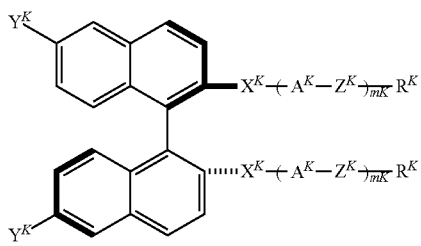

(K5) 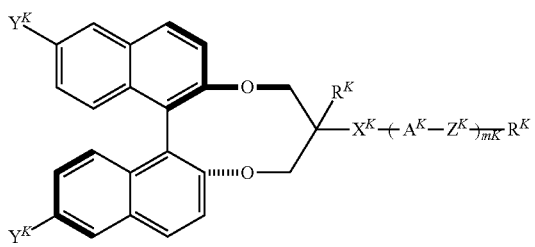

(K6) 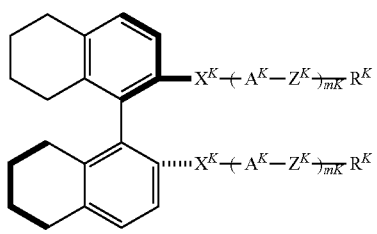

(K7) 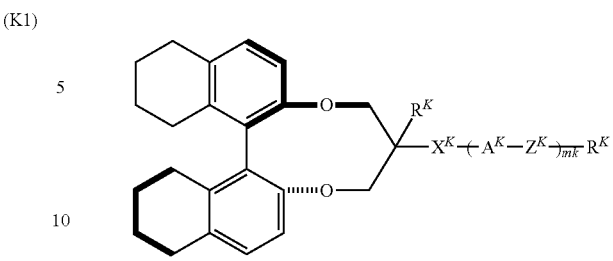

(wherein, in the formulas, $R^K$ is each independently hydrogen, halogen, —C≡N, —N=C=O, —N=C=S or alkyl having 1 to 12 carbons, at least one piece of —CH$_2$— in $R^K$ may be replaced by —O—, —S—, —COO— or —OCO—, at least one piece of —CH$_2$—CH$_2$— in $R^K$ may be replaced by —CH=CH—, —CF=CF— or —C≡C—, and at least one piece of hydrogen in $R^K$ may be replaced by fluorine or chlorine;

$A^K$ is each independently an aromatic 6-membered to 8-membered ring, a non-aromatic 3-membered to 8-membered ring or a condensed ring having 9 or more carbons, and at least one piece of hydrogen of the rings may be replaced by halogen, alkyl or haloalkyl having 1 to 3 carbons, —CH$_2$— of the rings may be replaced by —O—, —S— or —NH—, and —CH= may be replaced by —N=;

$Y^K$ is each independently hydrogen, halogen, alkyl having 1 to 3 carbons, haloalkyl having 1 to 3 carbons, an aromatic 6-membered to 8-membered ring, a non-aromatic 3-membered to 8-membered-ring or a condensed ring having 9 or more carbons, and at least one piece of hydrogen of the rings may be replaced by halogen, alkyl or haloalkyl having 1 to 3 carbons, —CH$_2$— in the alkyl may be replaced by —O—, —S— or —NH—, and —CH= may be replaced by —N=;

$Z^K$ is each independently a single bond or alkylene having 1 to 8 carbons, at least one piece of —CH$_2$— in the alkylene may be replaced by —O—, —S—, —COO—, —OCO—, —CSO—, —OCS—, —N=N—, —CH=N— or —N=CH—, at least one piece of —CH$_2$—CH$_2$— in the alkylene may be replaced by —CH=CH—, —CF=CF— or —C≡C—, and at least one piece of hydrogen of $Z^K$ may be replaced by halogen;

$X^K$ is each independently a single bond, —COO—, —OCO—, —CH$_2$O—, —OCH$_2$—, —CF$_2$O—, —OCF$_2$— or —CH$_2$CH$_2$—; and mK is each independently an integer from 1 to 3.).

Item 12. The liquid crystal composition according to any one of items 1 to 11, exhibiting a chiral nematic phase at any temperature in a temperature range from −20° C. to 70° C., and having 700 nanometers or less in a helical pitch in at least part of the temperature range.

Item 13. A mixture, containing the liquid crystal composition according to any one of items 1 to 12 and a polymerizable monomer.

Item 14. A polymer/liquid crystal composite material, obtained by polymerizing the mixture according to item 13 and used for a device driven by an optically isotropic liquid crystal phase.

Item 15. An optical device having electrodes arranged on one or both of substrates, a liquid crystal medium arranged between the substrates, and an electric field applying means for applying an electric field to the liquid crystal medium through the electrodes, wherein the liquid crystal medium is the liquid crystal composition according to any one of items 1 to 12, or the polymer/liquid crystal composite material according to item 14.

Item 16. Use of the liquid crystal composition according to any one of items 1 to 12, or the polymer/liquid crystal composite material according to item 14 in an optical device.

Item 17. A compound, represented by formula (1-1-1) or (1-5-1):

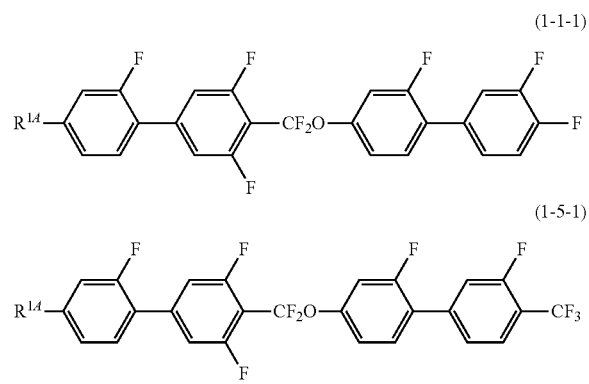

(1-1-1)

(1-5-1)

(wherein, in the formulas, $R^{14}$ is alkyl having 1 to 12 carbons.).

"Liquid crystal compound" herein represents a compound having a mesogen, and is not limited to a compound developing a liquid crystal phase. Specifically, "liquid crystal compound" is a generic term for a compound developing the liquid crystal phase such as a nematic phase and a smectic phase, and a compound having no liquid crystal phase but being useful as a component of a liquid crystal composition.

"Liquid crystal medium" is a generic term for the liquid crystal composition and the polymer/liquid crystal composite.

"Achiral component" is an achiral mesogen compound, and is a component contain neither an optically active compound nor a compound having a polymerizable functional group. Accordingly, "achiral component" contains no chiral agent, no monomer, no polymerization initiator, no antioxidant, no ultraviolet light absorbent, no curing agent, no stabilizer or the like.

"Chiral agent" is an optically active compound, and is a component used in order to provide the liquid crystal composition with desired twisted molecular arrangement.

"Liquid crystal display device" is a generic term for a liquid crystal display panel and a liquid crystal display module.

Moreover, "optical device" means various devices that perform a function of optical modulation, optical switching or the like by utilizing an electro-optic effect. Specific examples include an optical modulator used for a display device (liquid crystal display device), an optical communication system, optical information processing and various sensor systems. With regard to optical modulation that utilizes a change of a refractive index by applying voltage to an optically isotropic liquid crystal medium, a Kerr effect is known. The Kerr effect means a phenomenon in which a value of electric birefringence $\Delta n(E)$ is proportional to a square of electric field E, and an equation: $\Delta n(E)=K\lambda E^2$ holds in a material showing the Kerr effect (K: Kerr coefficient (Kerr constant), $\lambda$: wavelength). Here, the value of electric birefringence means a value of refractive index anisotropy induced when the electric field is applied to an isotropic medium.

"Liquid crystal compound," "liquid crystal composition" and "liquid crystal display device" may be occasionally abbreviated as "compound," "composition" and "device," respectively.

Moreover, for example, a maximum temperature of a liquid crystal phase is a phase transition temperature between a liquid crystal phase and an isotropic phase, and may be occasionally abbreviated simply as a clearing point or maximum temperature. A minimum temperature of the liquid crystal phase may be occasionally abbreviated as a minimum temperature. In compounds (2) to (5), a symbol $A^1$, $B^1$, $C^1$ or the like surrounded by a hexagonal shape corresponds to ring $A^1$, ring $B^1$, ring $C^1$ or the like, respectively. An amount of compound expressed in terms of percentage is expressed in terms of weight percentage (% by weight) based on the total weight of the composition. A plurality of identical symbols such as ring $A^1$, $Y^1$ and B are described in identical formulas or different formulas, but the symbols may be identical or different.

"Alkyl" herein may have a straight chain or a branched chain, and specific examples include —$CH_3$, —$C_2H_5$, —$C_3H_7$, —$C_4H_9$, —$C_5H_{11}$, —$C_5H_{13}$, —$C_7H_{15}$, —$C_8H_{17}$, —$C_9H_{19}$, —$C_{10}H_{21}$, —$C_{11}H_{23}$ and —$C_{12}H_{25}$.

"Alkenyl" herein may have a straight chain or a branched chain, and specific examples include —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$ and —$(CH_2)_3$—CH=$CH_2$.

Moreover, a preferred configuration of —CH=CH— depends on a position of a double bond. A trans configuration is preferred in alkenyl having the double bond in an odd-numbered position, such as —CH=$CHCH_3$, —CH=$CHC_2H_5$, —CH=$CHC_3H_7$, —CH=$CHC_4H_9$, —$C_2H_4$CH=$CHCH_3$ and —$C_2H_4$CH=$CHC_2H_5$. A cis configuration is preferred in alkenyl having the double bond at an even-numbered position, such as —$CH_2$CH=$CHCH_3$, —$CH_2$CH=$CHC_2H_5$ and —$CH_2$CH=$CHC_3H_7$. An alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327. As the position of the alkenyl group, a position in which no conjugation is formed with a benzene ring is preferred.

"Alkynyl" herein may have a straight chain or a branched chain, and specific examples include —C≡CH, —C≡$CCH_3$, —$CH_2$C≡CH, —C≡$CC_2H_5$, —$CH_2$C≡$CCH_3$, —$(CH_2)_2$—C≡CH, —C≡$CC_3H_7$, —$CH_2$C≡$CC_2H_5$, —$(CH_2)_2$—C≡$CCH_3$ and —C≡$C(CH_2)_5$.

"Alkoxy" herein may have a straight chain or a branched chain, and specific examples include —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$, —$OC_9H_{19}$, —$OC_{10}H_{21}$ and —$OC_{11}H_{23}$.

"Alkoxyalkyl" herein may have a straight chain or a branched chain, and specific examples include —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$ and —$(CH_2)_5$—$OCH_3$.

"Alkenyloxy" herein may have a straight chain or a branched chain, and specific examples include —$OCH_2$CH=$CH_2$, —$OCH_2$CH=$CHCH_3$ and —$OCH_2$CH=$CHC_2H_5$.

Specific examples of "halogen" herein include fluorine, chlorine, bromine and iodine.

Advantageous Effects of Invention

A preferred compound of the invention exhibits liquid crystallinity, and has a comparatively high clearing point, a wide nematic phase temperature range and a comparatively large dielectric anisotropy.

A preferred liquid crystal composition, a polymer/liquid crystal composite material or the like of the invention show stability to heat, light and so forth, a high maximum temperature and a low minimum temperature of an optically isotropic liquid crystal phase, has a large dielectric anisotropy and a small temperature dependence of drive voltage in a temperature range centering on an operating temperature.

Moreover, the polymer/liquid crystal composite material in a preferred aspect of the invention shows a high maximum temperature and a low minimum temperature of the optically isotropic liquid crystal phase, and has a low drive voltage in an optical device driven in the optically isotropic liquid crystal phase and the small temperature dependence of drive voltage in the temperature range centering on the operating temperature.

Further, the optical device in the preferred aspect of the invention driven in the optically isotropic liquid crystal phase can be used in a wide temperature range, driven at a low voltage, has the small temperature dependence of drive voltage in the temperature range centering on the operating temperature, and has a high-speed electro-optic response and a large contrast ratio.

DESCRIPTION OF EMBODIMENTS

Figure 1:
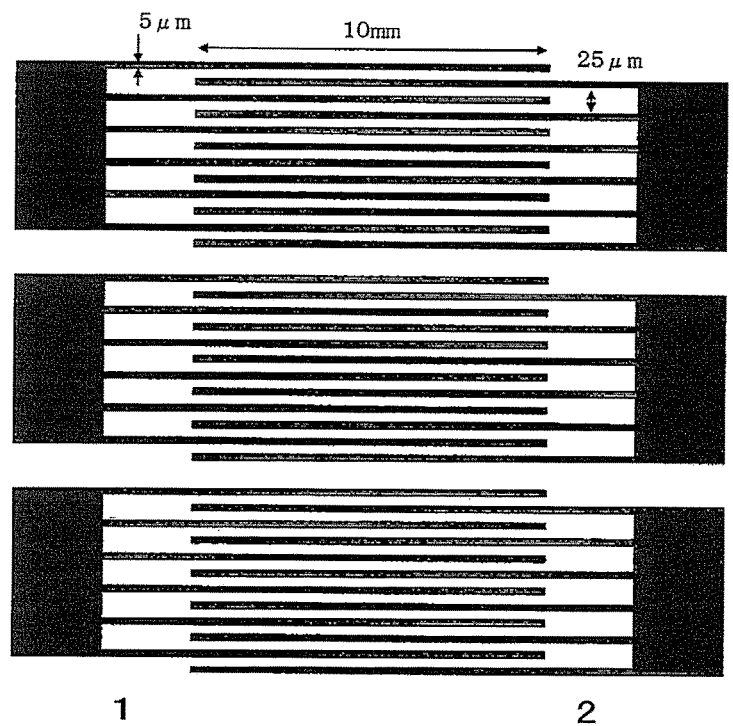
FIG. 1 shows a comb-shaped electrode substrate used in Examples.

A liquid crystal composition having an optically isotropic liquid crystal phase according to the invention contains an achiral component T and a chiral agent, and the achiral component T contains compound (1) as a first component. A first aspect of the liquid crystal composition of the invention is a composition containing the first component and any other component a name of which is not particularly described herein. First, compound (1) is described. The liquid crystal composition of the invention may further contain a solvent, a monomer, a polymerization initiator, a curing agent, a stabilizer (an antioxidant, an ultraviolet light absorbent or the like) in addition to the component described above.

1-1 Compound (1)

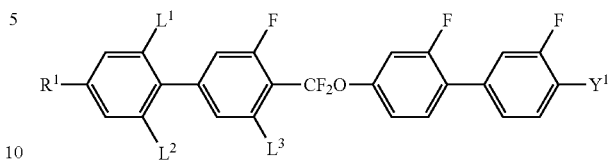

In compound (1), $R^1$ is hydrogen, alkyl having 1 to 12 carbons, alkenyl having 2 to 12 carbons, alkynyl having 2 to 12 carbons or alkoxy having 1 to 11 carbons.

$R^1$ preferably has a structure represented by formulas (CHN-1) to (CHN-4). $R^1$ is further preferably (CHN-1) or (CHN-2)

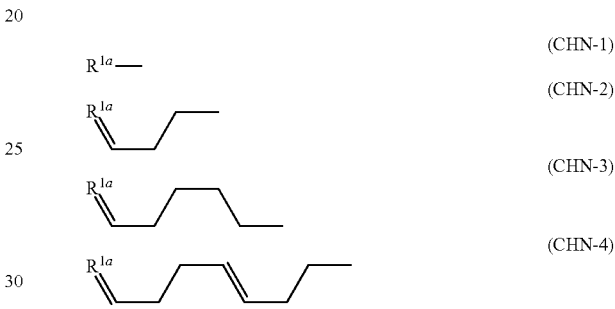

(In the formulas, $R^1$ is hydrogen or alkyl having 1 to 12 carbons.).

$L^1$, $L^2$ and $L^3$ are each independently hydrogen, fluorine or chlorine, but $L^2$ is preferably hydrogen and $L^1$ and $L^3$ are preferably fluorine or chlorine.

$Y^1$ is fluorine, chlorine, —$CF_3$ or —$OCF_3$, but $Y^1$ is preferably fluorine or —$CF_3$.

In compound (1), compounds (1-1) to (1-12) are preferably used.

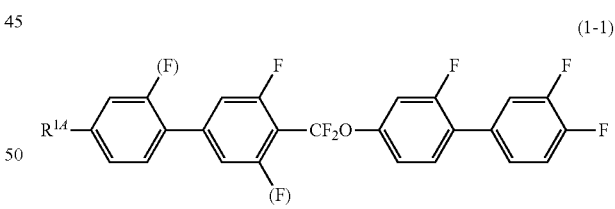

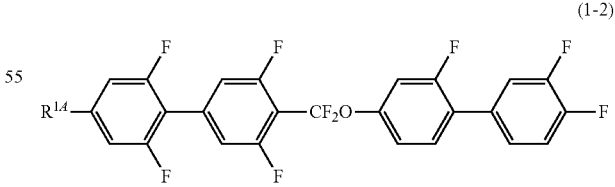

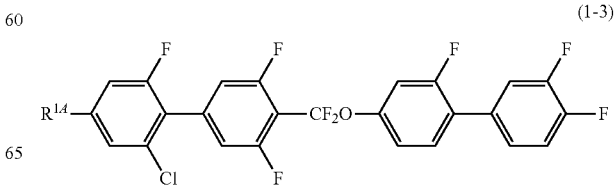

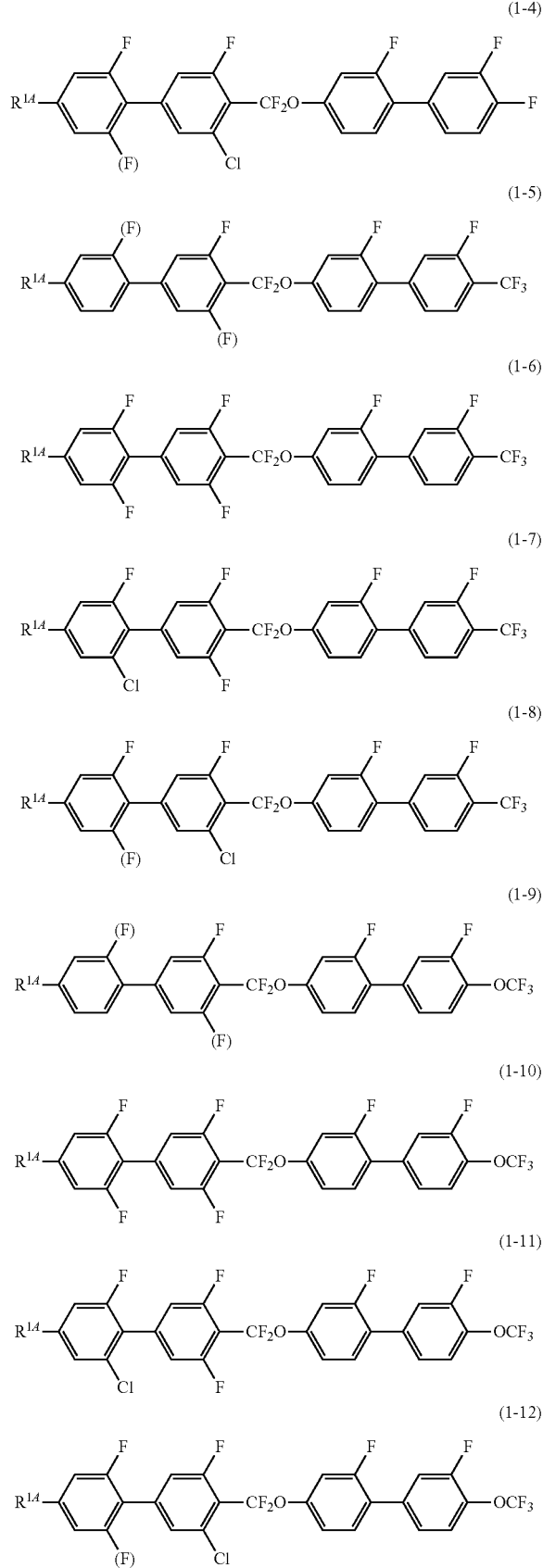

(In the formulas, $R^{14}$ is each independently hydrogen, alkyl having 1 to 12 carbons or alkenyl having 2 to 12 carbons, and (F) is fluorine or hydrogen.).

1-2 Properties of Compound (1)

Under conditions in which a device is ordinarily used, compound (1) is significantly stable physically and chemically, has a comparatively large dielectric anisotropy and a large refractive index anisotropy, and has a high clearing point and a comparatively good compatibility with other compounds. A composition containing the compound is stable under conditions in which the device is ordinarily used.

In compound (1), $L^1$, $L^2$ and $L^3$ are each independently hydrogen, fluorine or chlorine. In compound (1) in which $L^2$ is hydrogen, the compatibility at a low temperature is good, and in compound (1) in which $L^2$ is fluorine, the dielectric anisotropy is large. In compound (1) in which all of $L^1$, $L^2$ and L are hydrogen, the clearing point is high, and the compatibility at the low temperature is good. In compound (1) in which one of $L^1$, $L^2$ and $L^3$ is fluorine, the dielectric anisotropy is large. In compound (1) in which $L^1$ and $L^3$ are fluorine and $L^2$ is hydrogen, a balance between magnitude of dielectric anisotropy and compatibility is good. Moreover, in compound (1) in which $L^2$ or $L^3$ is chlorine, the refractive index is large, the melting point is low and the compatibility with other compounds is good.

$Y^1$ is fluorine, chlorine, —$CF_3$ or —$OCF_3$. In compound (1) in which $Y^1$ is fluorine or —$OCF_3$, the dielectric anisotropy is large, and the compatibility with other compounds is good. In compound (1) in which $Y^1$ is —$CF_3$, the dielectric anisotropy is significantly large. In compound (1) in which $Y^1$ is chlorine, the refractive index anisotropy is large.

Accordingly, if compound (1) in which any one of $L^1$, $L^2$ or $L^3$ is fluorine and $Y^1$ is fluorine, for example, is used in the liquid crystal composition, the temperature range of the liquid crystal phase can be extended, and compound (1) can be used in the form of a display device in the wide temperature range. Moreover, if compound (1) in which $L^2$, $L^3$ or $Y^1$ is chlorine is used, compound (1) has the comparatively large dielectric anisotropy and the large refractive index anisotropy, and therefore is useful as a component for decreasing drive voltage of the liquid crystal composition driven in the optically isotropic liquid crystal phase.

Compound (1) has an excellent feature of capability of increasing the clearing point of the liquid crystal composition, decreasing the drive voltage or extending the temperature range on a low temperature side by using only a small amount thereof.

1-3 Synthesis of Compound (1)

Compound (1) can be prepared by suitably combining publicly known techniques in synthetic organic chemistry. A plurality of methods of preparing compound (1) are provided, and compound (1) can be appropriately prepared from commercially available reagents.

Moreover, upon preparing compound (1), methods for introducing objective terminal groups, rings and linking groups into starting materials are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza, in Japanese) (Maruzen Co., Ltd.).

One example of a scheme for preparing compound (1) is shown below, but synthesis of compound (1) is not limited to the scheme.

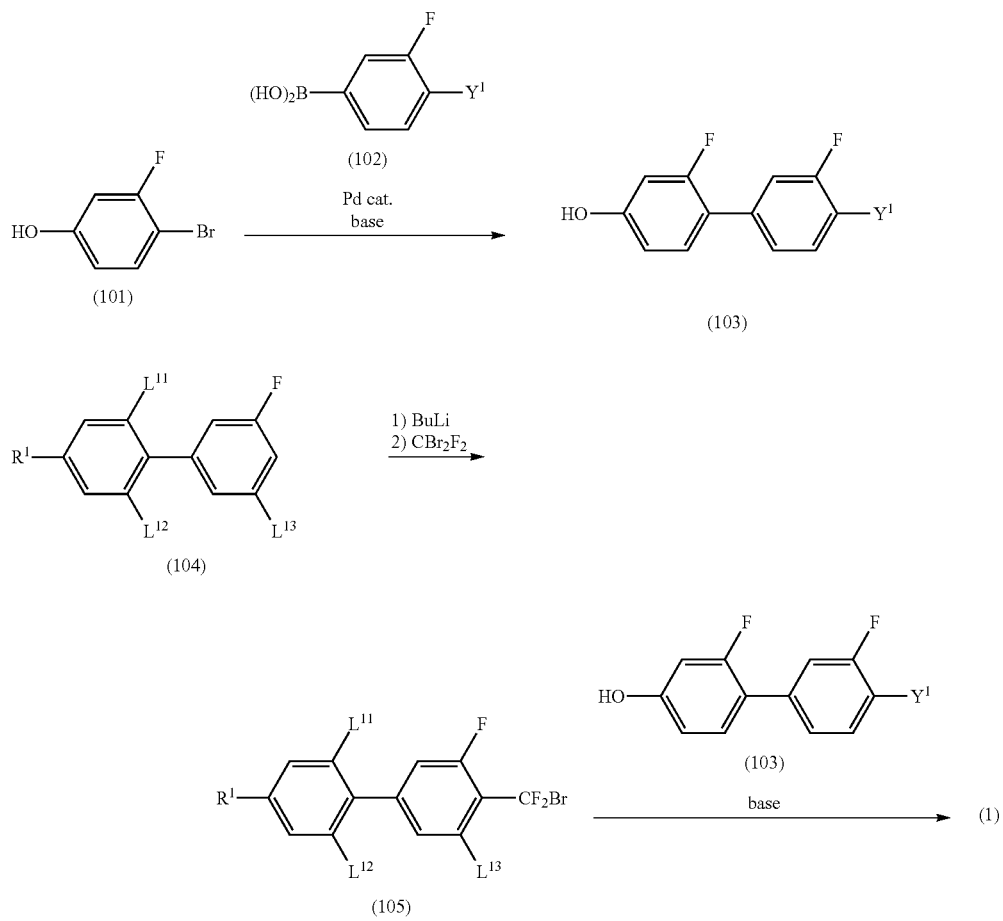

Compounds (101), (102) and (104) are commercially available, or can be prepared by a general synthetic method in organic chemistry. Compound (103) is obtained by allowing a metal catalyst such as palladium to act on a mixture of halogen compounds (101) and (102) to perform a coupling reaction in the presence of a base.

Compound (105) is obtained by preparing a lithium reagent by using butyl lithium or the like on compound (104) and subsequently allowing dibromodifluoromethane to act on the reagent.

Compound (1) is obtained by performing an etherification reaction on compounds (105) and (103) in the presence of a base.

2-1 Liquid Crystal Composition

The liquid crystal composition of the invention contains compound (1) and is a composition that develops the optically isotropic liquid crystal phase. An optically isotropic liquid crystal composition may contain a chiral agent in addition to the achiral component T containing compound (1), and may also contain an antioxidant, an ultraviolet light absorbent, a stabilizer or the like.

The achiral component T is a composition containing one kind of compound (1), and a liquid crystal composition containing two or more kinds of compounds (1). The achiral component T of the invention may further contain at least one compound selected from compounds (3) to (7) when necessary. The achiral component T preferably contains at least one compound selected from compound (2), (3), (5) or (7) in addition to compound (1), and particularly preferably contains compound (3) or (7). According to required properties, the achiral component T contains compound (4) or (6). Compounds (1) to (7) are a liquid crystal compound.

Because compound (1) simultaneously has the comparatively high clearing point, the comparatively large dielectric anisotropy and a good compatibility at a low temperature, the achiral component T using compound (1) also develops a wide temperature range of the liquid crystal phase and a large dielectric anisotropy. Therefore, the optically isotropic liquid crystal composition using the achiral component T is useful as the composition to be used in an optical device.

Based on the total weight of the achiral component T, compound (1) is contained preferably in 1% by weight to 60% by weight in total, further preferably in 5% by weight to 40% by weight in total, and particularly preferably in 10% by weight to 30% by weight in total.

In order to develop the large dielectric anisotropy, further addition of compound (3) or (7) is preferred. Such a composition develops a significantly large dielectric anisotropy, and therefore is the composition significantly effective in achieving a low voltage of the optical device.

2-2-1 Compound (2)

The achiral component T of the invention may further contain at least one compound (2) in addition to compound (1). The liquid crystal composition of the invention may also contain at least one compound selected from compounds (3) to (7) in addition to compound (1).

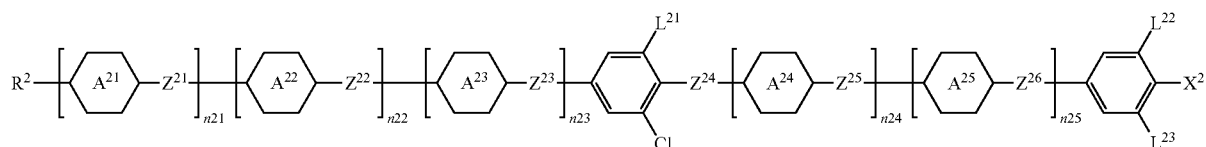

(2)

In compound (2), $R^2$ is hydrogen or alkyl having 1 to 12 carbons, at least one piece of —$CH_2$— in $R^2$ may be replaced by —O—, —S—, —COO—, —OCO—, —CH=CH—, —CF=CF— or —C≡C—, and at least one piece of hydrogen in $R^2$ may be replaced by halogen or alkyl having 1 to 3 carbons, However, in $R^2$, a case where —O— and —CH=CH— are adjacent is excluded, and a case where —CO— and —CH=CH— are adjacent is excluded.

$R^2$ is preferably alkyl having 1 to 12 carbons, alkenyl having 2 to 12 carbons or alkoxy having 1 to 11 carbons.

$A^{21}$ to $A^{25}$ are each independently 1,4-cyclohexylene, 1,3-dioxane-2,5-diyl, 1,4-phenylene, 1,4-phenylene in which one or two pieces of hydrogen are replaced by fluorine, 1,4-phenylene in which two pieces of hydrogen are replaced by fluorine and chlorine, respectively, pyridine-2,5-diyl or pyrimidine-2,5-diyl.

$A^{21}$ to $A^{L5}$ are preferably 1,4-phenylene, 1,4-phenylene in which one or two pieces of hydrogen are replaced by fluorine, in which the stability and the dielectric anisotropy of the compound are large.

$Z^{21}$ to $Z^{26}$ are each independently a single bond or alkylene having 1 to 4 carbons, and at least one piece of —$CH_2$— in the alkylene may be replaced by —O—, —COO— or —$CF_2O$—.

All of $Z^{21}$ to $Z^{26}$ are preferably a single bond or at least one of $Z^{21}$ to $Z^{26}$ is preferably —$CF_2O$—, in which the good compatibility with other liquid crystal compounds is obtained. A case where n24=1 and $Z^{25}$ is —$CF_2O$— is particularly preferred.

$L^{21}$, $L^{22}$, and $L^{23}$ are each independently hydrogen or fluorine, but $L^{33}$, $L^{35}$ and $L^{36}$ are preferably fluorine, in which the dielectric anisotropy is large.

$X^2$ is fluorine, chlorine, —$CF_3$ or —$OCF_3$, and preferably fluorine and —$CF_3$.

Then, n21, n22, n23, n24 and n25 are each independently 0 or 1, and an expression: 2≤n21+n22+n23+n24+n25≤3 holds.

However, when n21+n22+n23+n24+n25=2, both $L^{22}$ and $L^{23}$ are fluorine.)

A compound in which the expression: n21+n22+n23+n24+n25=2 holds has the high clearing point, and a compound in which the expression: n21+n22+n23+n24+n25=1 holds has a low melting point.

Compound (2) has a chlorophenylene ring. Compound (2) is significantly stable physically and chemically under conditions in which the device is ordinarily used, and has the good compatibility with other liquid crystal compounds. Further, the compound is hard to develop a smectic phase. A composition containing the compound is stable under conditions in which the device is ordinarily used.

A compound having objective physical properties can be obtained by suitably selecting kinds of a ring system, a terminal group and a linking group of compound (2).

When linking groups $Z^{21}$ to $Z^{26}$ are a single bond or —$CF_2O$— in compound (2), compound (2) is comparatively stable chemically and comparatively hard to cause deterioration. Further, when the linking group is a single bond, viscosity is small. When the linking group is —$CF_2O$—, the dielectric anisotropy is large. When $X^2$ is fluorine, chlorine or —$OCF_3$, compatibility with other liquid crystal compounds at the low temperature is excellent, and when $X^2$ is —$CF_3$, the dielectric anisotropy is large.

In compound (2), a compound represented by formula (2-1) is preferably used.

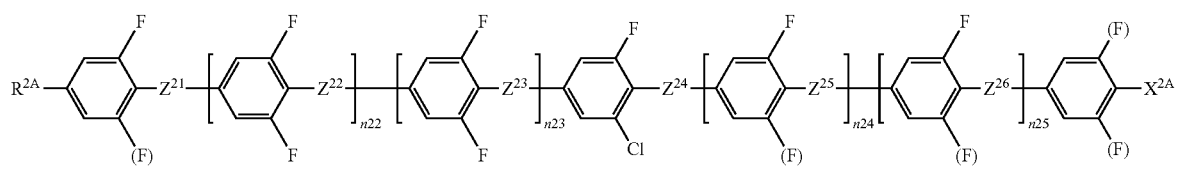

(2-1)

In the formula, $R^{2A}$ is alkyl having 1 to 12 carbons, alkenyl having 2 to 12 carbons or alkoxy having 1 to 11 carbons; $Z^{21}$, $Z^{22}$, $Z^{23}$, $Z^{24}$, $Z^{25}$ and $Z^{26}$ are each independently a single bond or —$CF_2O$—; n22, n23, n24, and n25 are each independently 0 or 1, and a value of the expression: n22+n23+n24+n25 is an integer of 1 or 2. $X^{2A}$ is fluorine, chlorine, —$CF_3$ and —$OCF_3$; and (F) each independently represents hydrogen or fluorine.

In compound (2), compounds (2-1-1) to (2-1-5) are preferably used.

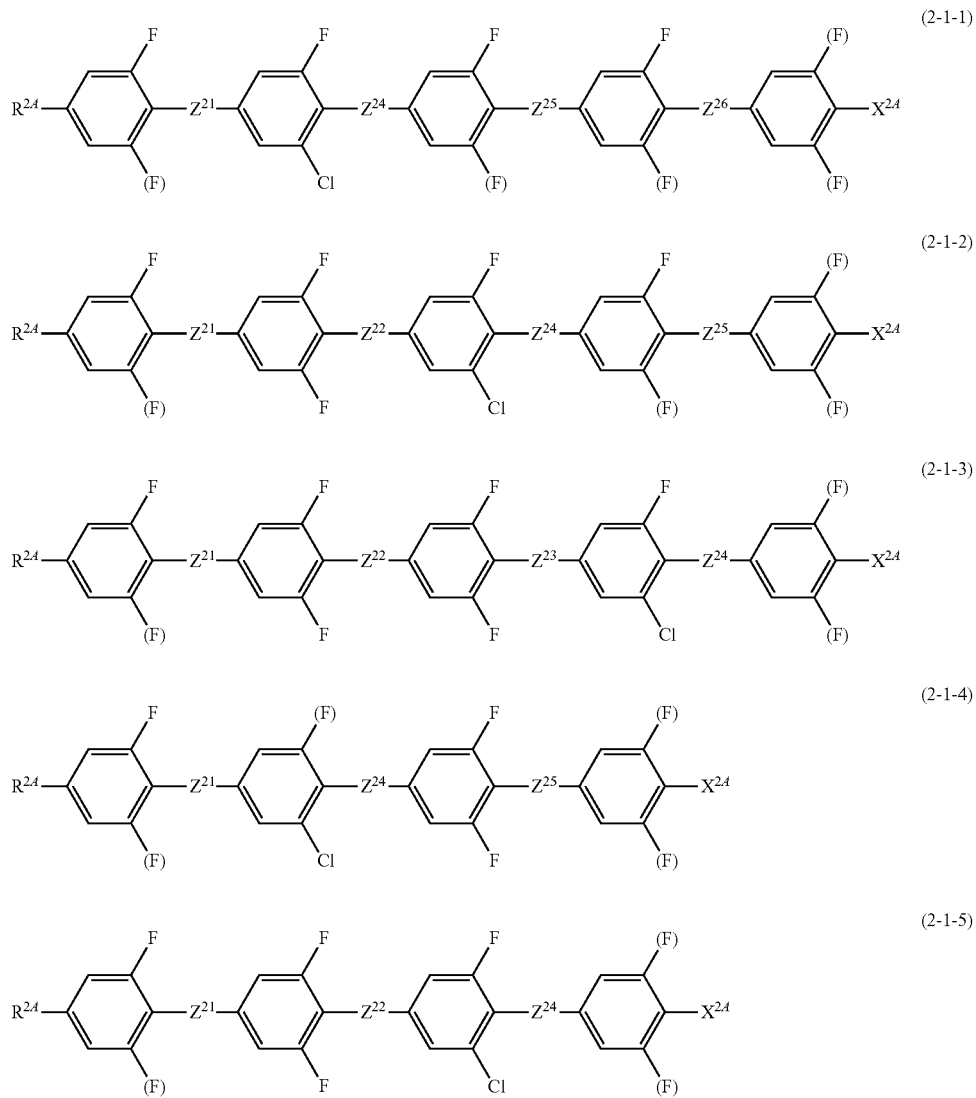
(In the formulas, definitions of $R^{2A}$, $X^{2A}$ and (F) are the same with the definitions in compound (2-1).).
In compound (2), compounds (2-1-1-1) to (2-1-1-3), (2-1-2-1) to (2-1-2-3), (2-1-3-1) to (2-1-3-3), (2-1-4-1) to (2-1-4-3) or (2-1-5-1) to (2-1-5-3) are preferably used, and compounds represented by formula (2-1-1-1) or (2-1-1-2), formula (2-1-2-1) or (2-1-2-2) or formula (2-1-3-1), (2-1-3-2), (2-1-4-2), (2-1-4-3) or (2-1-5-3) is further preferably used.
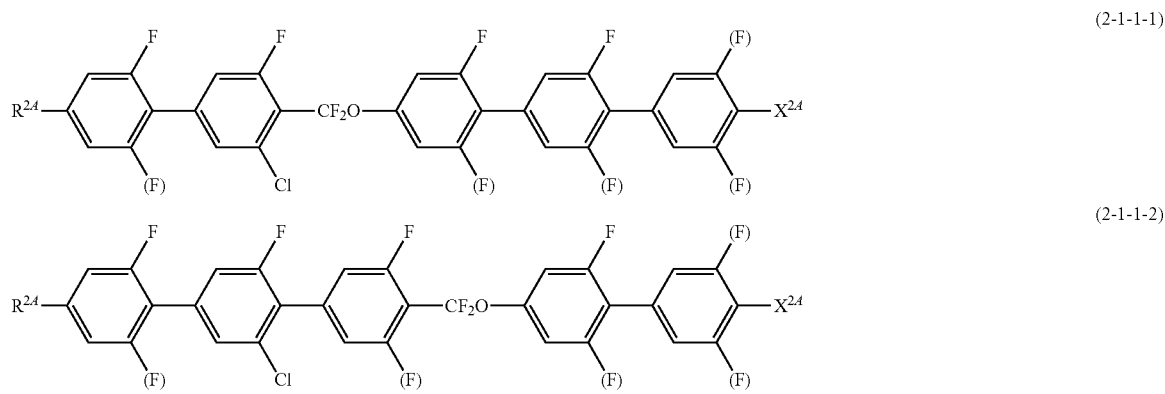

-continued
(2-1-1-3)
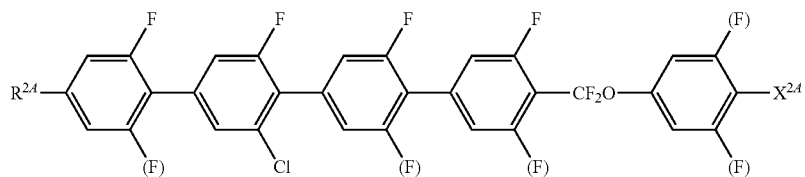
(2-1-2-1)
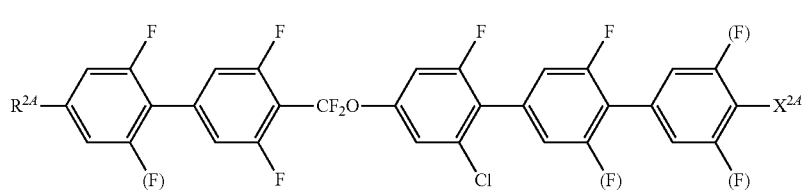
(2-1-2-2)
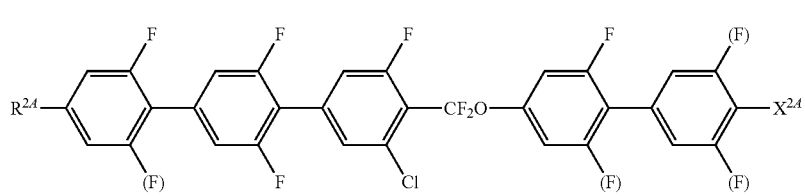
(2-1-2-3)
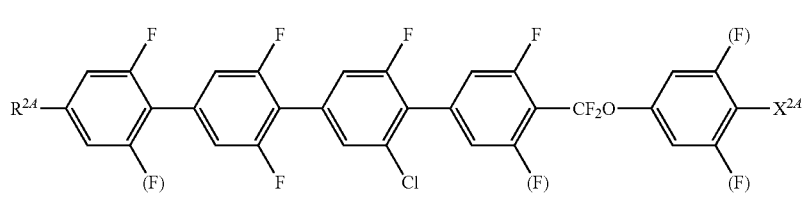
(2-1-3-1)
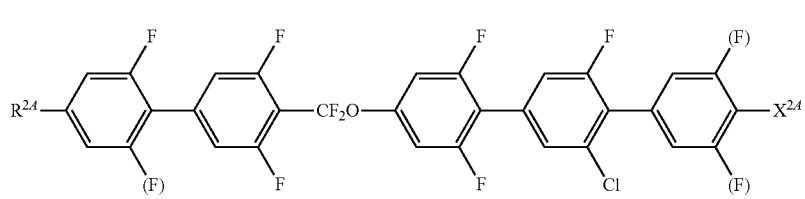
(2-1-3-2)
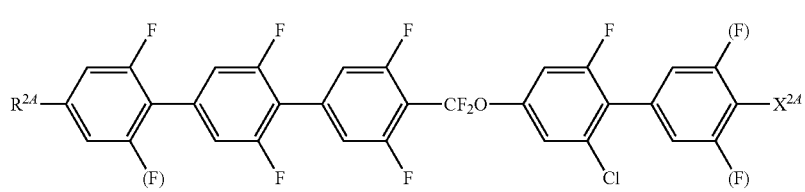
(2-1-3-3)
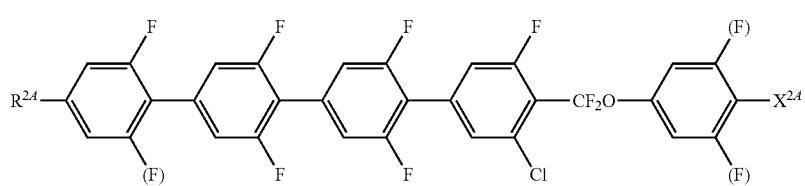
(2-1-4-1)
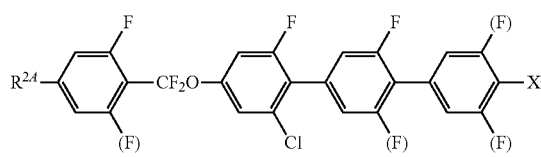
(2-1-4-2)
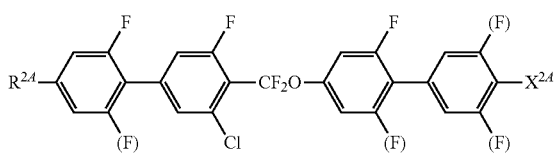

(2-1-4-3)

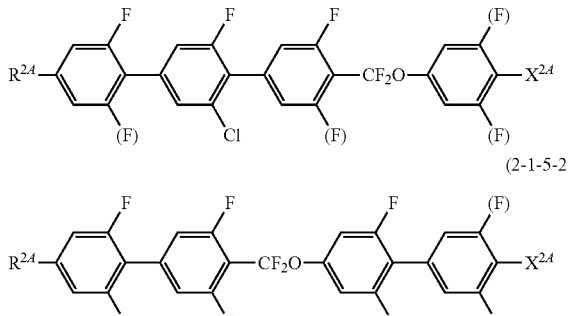

(2-1-5-1)

(2-1-5-2)

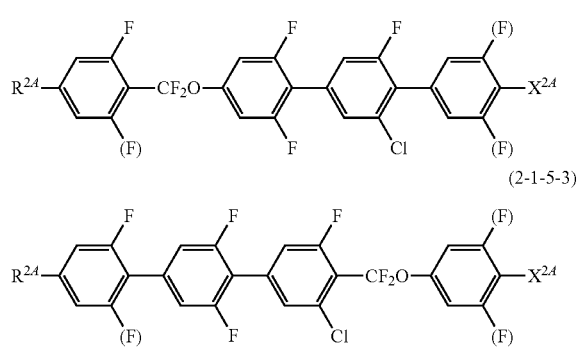

(2-1-5-3)

(In the formulas, definitions of $R^{2A}$, (F) and $X^{2A}$ are the same with the definitions in compound (2-1).).

Compound (2) has the good compatibility, the large dielectric anisotropy and the large refractive index anisotropy. Based on the total weight of the achiral component T, compound (2) is contained preferably in 0.5% by weight to 70% by weight in total, further preferably in 5% by weight to 60% by weight in total, and particularly preferably in 10% by weight to 50% by weight in total.

2-3-1 Compound (3)

The achiral component T of the invention may also contain at least one compound (3) in addition to compound (1). The liquid crystal composition of the invention may also contain at least one of compounds (2) and (4) to (7) in addition to compound (1) and compound (3).

$X^3$ is hydrogen, halogen, —$SF_5$ or alkyl having 1 to 10 carbons, at least one piece of —$CH_2$— in the alkyl may be replaced by —O—, —S—, —COO— or —OCO—, at least one piece of —$CH_2$—$CH_2$— in the alkyl may be replaced by —CH=CH—, —CF=CF— or —C≡C—, and at least one piece of hydrogen in the alkyl may be replaced by fluorine or chlorine, however, in the alkyl, a case where —O— and —CH=CH— are adjacent is excluded and a case where —CO— and —CH=CH— are adjacent is excluded.

Specific examples of alkyl in which at least one piece of hydrogen in $X^3$ is replaced by halogen include —$CH_2F$, —$CHF_2$, —$CF_3$, —$(CH_2)_2$—F, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$, —$CHFCF_2CF_3$, —$(CH_2)_4$—F, —$(CF_2)_4$—F, —$(CH_2)_5$—F and —$(CF_2)_5$—F.

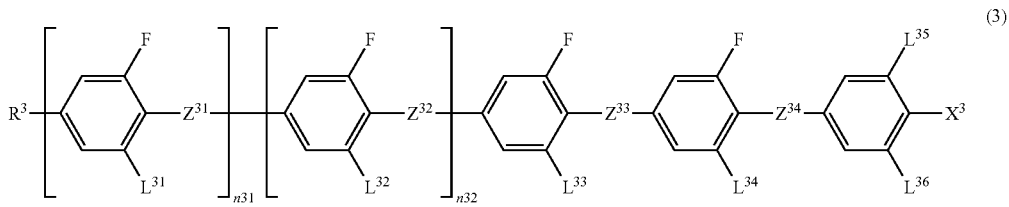

(3)

In compound (3), $R^3$ is hydrogen or alkyl having 1 to 12 carbons, at least one piece of —$CH_2$— in $R^3$ may be replaced by —O—, —S—, —COO— or —OCO—, at least one piece of —$CH_2$—$CH_2$— in $R^3$ may be replaced by —CH=CH—, —CF=CF— or —C≡C—, and at least one piece of hydrogen in $R^3$ may be replaced by fluorine or chlorine, however, in $R^3$, a case where —O— and —CH=CH— are adjacent is excluded, and a case where —CO— and —CH=CH— are adjacent is excluded.

$R^3$ is preferably alkyl having 1 to 12 carbons, alkenyl having 2 to 12 carbons or alkoxy having 1 to 11 carbons.

$Z^{31}$, $Z^{32}$, $Z^{33}$ and $Z^{34}$ are each independently a single bond or alkylene having 1 to 4 carbons, and at least one piece of —$CH_2$— in the alkylene may be replaced by —O—, —COO— or —$CF_2O$—.

$Z^{31}$, $Z^{32}$ and $Z^{33}$ are preferably a single bond, —COO— or —$CF_2O$—, and further preferably single bonds in all, or —$CF_2O$— in any one thereof.

$L^{31}$, $L^{32}$, $L^{33}$, $L^{34}$, $L^{35}$ and $L^{36}$ are hydrogen or fluorine, but when n32 is 1 and $Z^{32}$ is —COO— or —$CF_2O$—, $L^{32}$, $L^{35}$ and $L^{36}$ are preferably fluorine, and when $Z^{33}$ is —COO— or —$CF_2O$—, $L^{33}$, $L^{35}$ and $L^{36}$ are preferably fluorine.

Specific examples of alkoxy in which at least one piece of hydrogen is replaced by halogen include —$OCH_2F$, —$OCHF_2$, —$OCF_3$, —O—$(CH_2)_2$—F, —$OCF_2CH_2F$, —$OCF_2CHF_2$, —$OCH_2CF_3$, —O—$(CH_2)_3$—F, —O—$(CF_2)_3$—F, —$OCF_2CHFCF_3$, —$OCHFCF_2CF_3$, —O—$(CH_2)_4$—F, —O—$(CF_2)_4$—F, —O—$(CH_2)_5$—F, and —O—$(CF_2)_5$—F.

Specific examples of alkenyl in which at least one piece of hydrogen is replaced by halogen include —CH=CHF, —CH=$CF_2$, —CF=CHF, —CH=$CHCH_2F$, —CH=$CHCF_3$, —$(CH_2)_2$—CH=$CF_2$, —$CH_2CH$=$CHCF_3$, —CH=$CHCF_3$ and —CH=$CHCF_2CF_3$.

$X^3$ is preferably fluorine, chlorine, —$CF_3$, —$CHF_2$, —$OCF_3$ or —$OCHF_2$, and further preferably fluorine, chlorine, —$CF_3$— or —$OCF_3$.

Then, n31 and n32 are each independently 0 or 1.

However, when an expression: n31+n32=1 holds and $Z^{33}$ is —$CF_2O$—, both $L^{35}$ and $L^{36}$ are fluorine.

Compound (3) is significantly stable physically and chemically under conditions in which the device is ordinarily used, and has the good compatibility with other liquid crystal compounds. A composition containing the compound is stable under conditions in which the device is ordinarily used. Compound (3) has the comparatively high clearing point, and has the large dielectric anisotropy and the large refractive index anisotropy.

In compound (3), compounds (3-1) to (3-3) are preferably used, and compounds (3-2) and (3-3) are further preferably used.

(3-1)
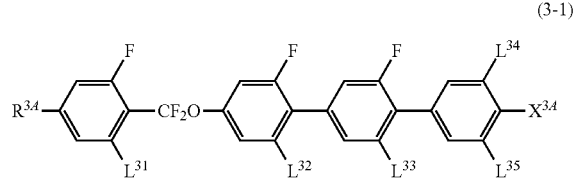

(3-2)
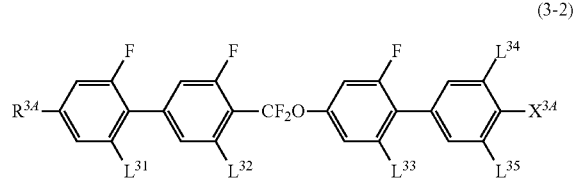

(3-3)
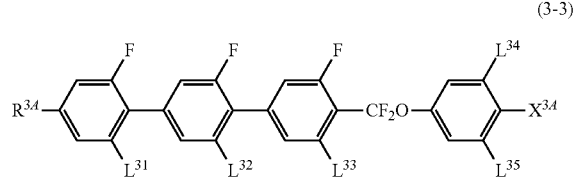

(In the formulas, $R^{3A}$ is each independently alkyl having 1 to 12 carbons, alkenyl having 2 to 12 carbons or alkoxy having 1 to 11 carbons; $L^3$, $L^{32}$, $L^{33}$, $L^{34}$ and $L^{35}$ are each independently hydrogen or fluorine; and $X^{3A}$ is fluorine, chlorine, —$CF_3$ or —$OCF_3$.)

In compound (3-2), compounds (3-2A) to (3-2H) are further preferably used, compounds (3-2A) to (3-2D) are particularly preferably used, and compounds (3-2A) and (3-2C) are most preferably used.

In compound (3-3), compounds (3-3A) to (3-3D) are further preferably used, compounds (3-3A) and (3-3C) are particularly preferably used, and compound (3-3A) is most preferably used.

(3-2A)
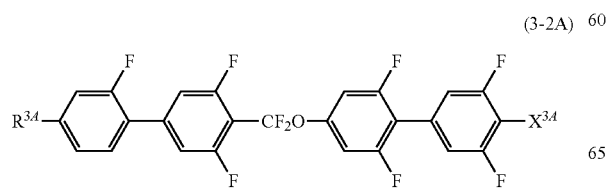

(3-2B)
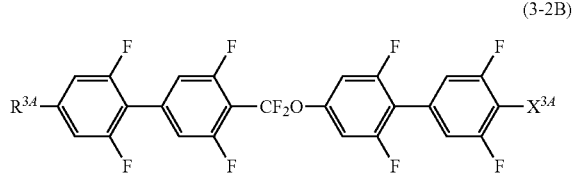

(3-2C)
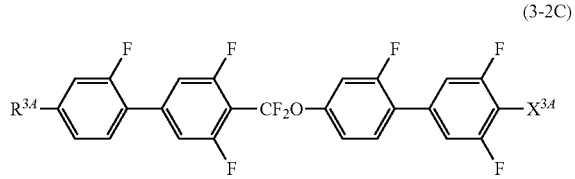

(3-2D)
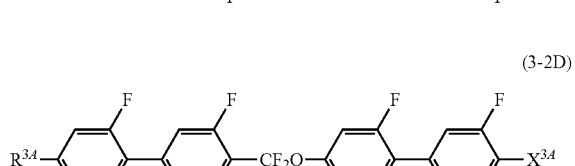

(3-2E)
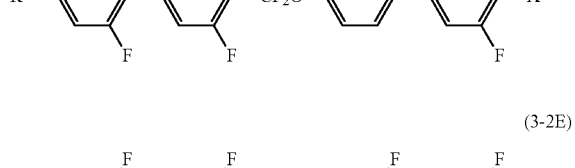

(3-2F)
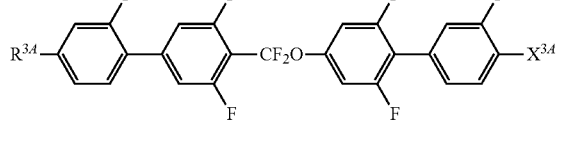

(3-3A)
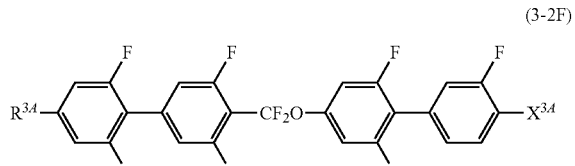

(3-3B)
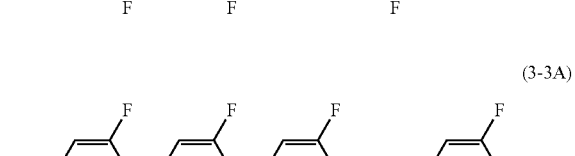

(3-3C)
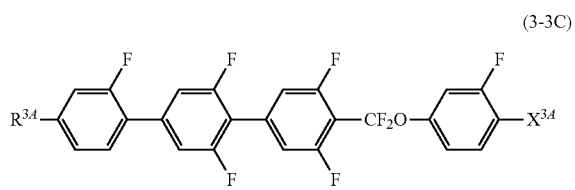

(3-3D)

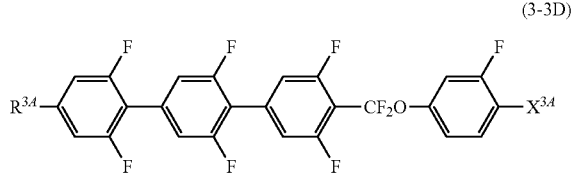

(In the formulas, $R^{3A}$ is independently alkyl having 1 to 12 carbons, alkenyl having 2 to 12 carbons or alkoxy having 1 to 11 carbons; and $X^{3A}$ is fluorine, chlorine, —$CF_3$ or —$OCF_3$.).

Based on the total weight of the achiral component T, compound (3) is contained preferably in 0.5% by weight to 70% by weight in total, further preferably in 5% by weight to 60% by weight in total, and particularly preferably in 10% by weight to 50% by weight in total.

In compound (3), physical properties such as the clearing point, the refractive index anisotropy and the dielectric anisotropy can be arbitrarily adjusted by suitably selecting $R^3$, a group on a phenylene ring ($L^{31}$ to $L^{36}$, and $X^3$) or $Z^{31}$ to $Z^{34}$.

When the number of fluorine in $L^{31}$ to $L^{35}$ is large, the dielectric anisotropy is large. When both $L^{31}$ and $L^{32}$ are hydrogen, compound (3) is excellent in compatibility with other liquid crystals. When both $L^{35}$ and $L^{36}$ are fluorine, the dielectric anisotropy is particularly large.

When $Z^{31}$ to $Z^{34}$ are a single bond or —$CF_2O$—, the viscosity is small and compound (3) is chemically stable. When $Z^{31}$ to $Z^{34}$ are —$CF_2O$—, the dielectric anisotropy is large.

When $X^3$ is fluorine, chlorine, —$SF_5$, —$CF_3$, —$CHF_2$, —$CH_2F$, —$OCF_3$, —$OCHF_2$ or —$OCH_2F$, the dielectric anisotropy is large. When $X^3$ is fluorine, —$OCF_3$ or —$CF_3$, compound (3) is particularly stable chemically.

When n31+n32=0, the clearing point is low, the viscosity is low and the compatibility with other liquid crystal compounds is good. When n31+n32=1, the clearing point is comparatively high, the dielectric anisotropy is large, and refractive index anisotropy is large. When n31+n32=2, the clearing point is significantly high, the dielectric anisotropy is large, and the refractive index anisotropy is significantly large.

2-4-1 Compound (4)

The achiral component T of the invention may also contain at least one compound (4) in addition to compound (1). The liquid crystal composition of the invention may also contain at least one of compounds (2), (3) and (5) to (7) in addition to compound (1) and compound (4).

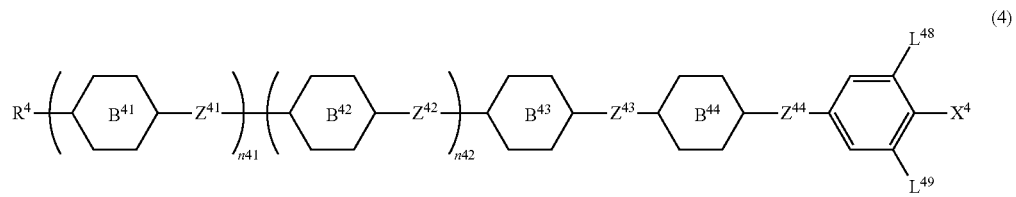

(4)

In compound (4), $R^4$ is alkyl having 1 to 12 carbons, alkenyl having 2 to 12 carbons or alkoxy having 1 to 11 carbons.

$B^{41}$, $B^{42}$, $B^{43}$ and $B^{44}$ are independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine 2,5-diyl.

$B^{41}$, $B^{42}$, $B^{43}$ and $B^{44}$ are preferably 1,4-phenylene, 3-fluoro-1,4-phenylene or 3,5-difluoro-1,4-phenylene for increasing the optical anisotropy, and 1,4-cyclohexylene for decreasing the viscosity.

$L^{48}$ and $L^{49}$ are independently hydrogen or fluorine, but when both $L^{48}$ and $L^{49}$ are fluorine, the dielectric anisotropy is large. When both $L^{48}$ and $L^{49}$ are hydrogen, the clearing point is high.

$Z^{41}$, $Z^{42}$, $Z^{43}$ and $Z^{44}$ are independently a single bond, ethylene, —COO—, —OCO—, —$CF_2O$— or —$OCF_2$—, but when $Z^{43}$ is —$CF_2O$—, both $L^{48}$ and $L^{49}$ are fluorine. In order to enhance the dielectric anisotropy and improve the compatibility, any one of $Z^{41}$, $Z^{42}$, $Z^{43}$ and $Z^{44}$ is preferably —$CF_2O$—.

When $Z^{41}$, $Z^{42}$, $Z^{43}$ and $Z^{44}$ are a single bond, the viscosity is low.

$X^4$ is fluorine, chlorine, —$CF_3$ or —$OCF_3$. When $X^4$ is fluorine or —$CF_3$, the dielectric anisotropy is large. When $X^4$ is fluorine or —$OCF_3$, the compatibility with other compound is good. When $X^4$ is chlorine, the refractive index anisotropy is large.

Then, n41 and n42 are 0 or 1. When n41+n42=1 and $Z^{43}$ is —$CF_2O$—, both $L^{48}$ and $L^{49}$ are fluorine. When a value: n41+n42 is 1 or 2, any one of $Z^{41}$, $Z^{42}$, $Z^{43}$ and $Z^{44}$ is particularly preferably —$CF_2O$—.

In compound (4), compounds (4-1) to (4-10) are preferably used.

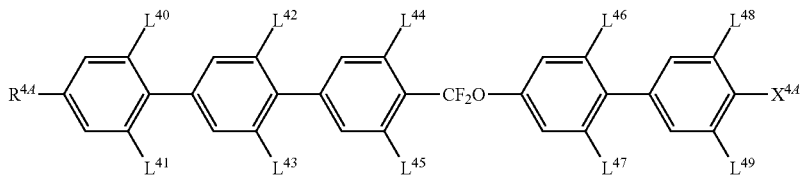

(4-1)

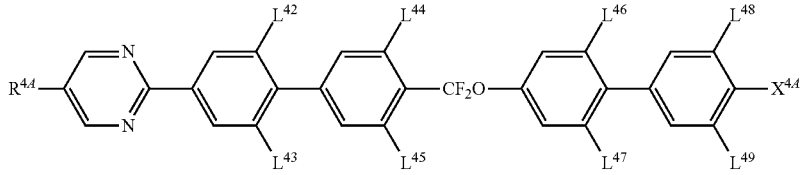

(4-2)

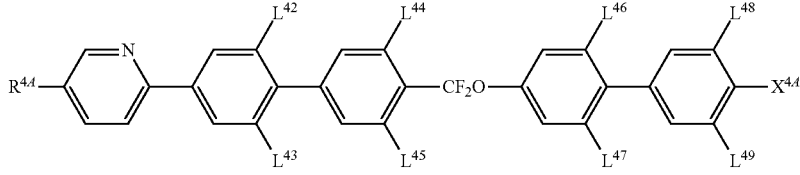

(4-3)

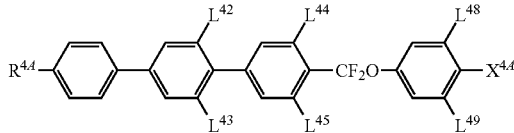

(4-4)

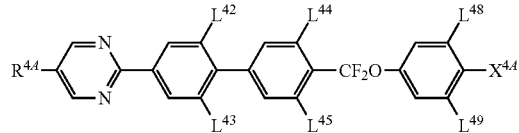

(4-5)

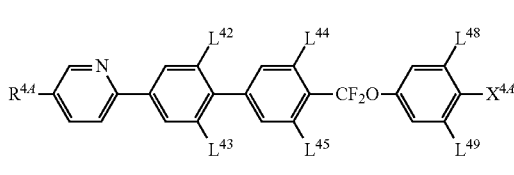

(4-6)

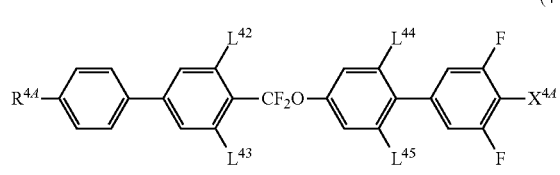

(4-7)

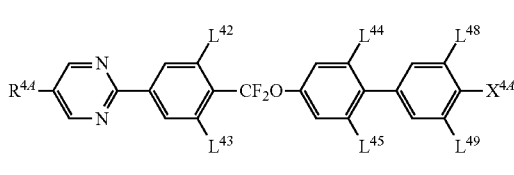

(4-8)

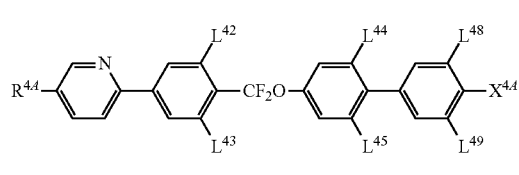

(4-9)

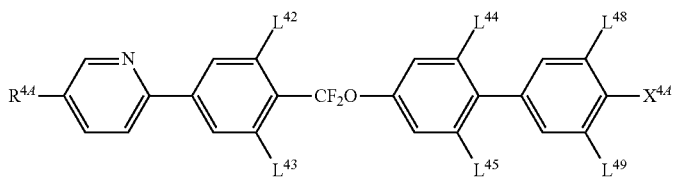

(4-10)

(In formulas (4-1) to (4-10), $R^{4A}$ is independently alkyl having 1 to 12 carbons, alkenyl having 2 to 12 carbons or alkoxy having 1 to 12 carbons;

$X^{4A}$ is fluorine, chlorine, —$CF_3$ or —$OCF_3$, and $L^{40}$ to $L^{49}$ are independently hydrogen or fluorine.).

In compounds (4-1) to (4-3), the clearing point is high and the compatibility is excellent as a pentacyclic compound. In compounds (4-5) to (4-7), the clearing point is high and the refractive index anisotropy is large, and in compounds (4-8) to (4-10), the compatibility is excellent. In $L^{40}$ to $L^{49}$, accordingly as the number of fluorine is larger, the dielectric anisotropy is larger.

Compound (4) is suitable for preparing the composition having the large dielectric anisotropy or the good compatibility at the low temperature. Based on the total weight of the achiral component T, compound (4) is contained preferably in 5% by weight to 40% by weight in total, further preferably in 5% by weight to 30% by weight in total, and particularly preferably in 5% by weight to 20% by weight in total.

2-5-1 Compound (5)

The achiral component T of the invention may also contain at least one compound (5) in addition to compound (1). Moreover, the liquid crystal composition of the invention may also contain at least one compound selected from compounds (2) to (4), (6) and (7) in addition to compound (1) and compound (5).

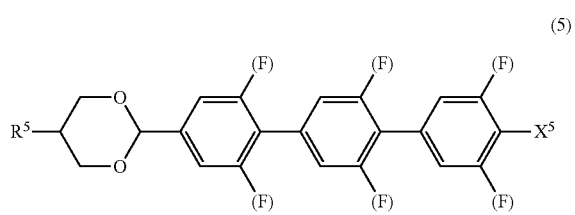

(5)

In compound (5), $R^5$ is hydrogen or alkyl having 1 to 12 carbons, at least one piece of —$CH_2$— in $R^5$ may be replaced by —O—, —S—, —COO— or —OCO—, at least one piece of —$CH_2$—$CH_2$— in $R^5$ may be replaced by —CH=CH—, —CF=CF— or —C≡C—, and at least one piece of hydrogen in $R^5$ may be replaced by fluorine or chlorine, however, in $R^5$, a case where —O— and —CH=CH— are adjacent is excluded, and a case where —CO— and —CH=CH— are adjacent is excluded.

$X^5$ is hydrogen, halogen, —$SF_5$ or alkyl having 1 to 10 carbons, at least one piece of —$CH_2$— in $X^5$ may be replaced by —O—, —S—, —COO— or —OCO—, at least one piece of —$CH_2$—$CH_2$— in $X^5$ may be replaced by —CH=CH—, —CF=CF— or —C≡C—, and at least one piece of hydrogen in $X^5$ may be replaced by fluorine or chlorine, however, in $X^5$, a case where —O— and —CH=CH— are adjacent is excluded, and a case where —CO— and —CH=CH— are adjacent is excluded.

Specific examples of $X^5$ include fluorine, chlorine, —$CF_3$, —$CHF_2$, —$OCF_3$ and —$OCHF_2$, and fluorine, chlorine, —$CF_3$ and —$OCF_3$ are preferred. When $X^5$ is chlorine or fluorine, the melting point is comparatively low and the compatibility with other liquid crystal compounds is particularly excellent. When $X^5$ is —$CF_3$, —$CHF_2$, —$OCF_3$ or —$OCHF_2$, the dielectric anisotropy is comparatively large.

When $X^5$ is fluorine, chlorine, —$SF_5$, —$CF_3$, —$OCF_3$ or —CH=CH—$CF_3$, the dielectric anisotropy is comparatively large, and when $X^5$ is fluorine, —$CF_3$, or —$OCF_3$, compound (5) is particularly stabilized chemically.

(F) is each independently hydrogen or fluorine.

In $R^5$ or $X^5$, specific examples of alkyl in which at least one piece of hydrogen is replaced by fluorine include —$CHF_2$, —$CF_3$, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$ and —$CHFCF_2CF_3$.

In $R^5$ and $X^5$, specific examples of alkoxy in which at least one piece of hydrogen is replaced by fluorine include —$OCHF_2$, —$OCF_3$, —$OCF_2CH_2F$, —$OCF_2CHF_2$, —$OCH_2CF_3$, —O—$(CF_2)_3$—F, —$OCF_2CHFCF_3$ and —$OCHFCF_2CF_3$.

In $R^5$ or $X^5$, specific examples of alkenyl in which at least one piece of hydrogen is replaced by fluorine include —CH=$CF_2$, —CF=CHF, —CH=$CHCH_2F$, —CH=$CHCF_3$, —$(CH_2)_2$—CH=$CF_2$, —$CH_2CH$=$CHCF_3$ and —CH=$CHCF_2CF_3$.

Compound (5) has a dioxane ring and three phenylene rings. Compound (5) is significantly stable physically and chemically under conditions in which the device is ordinarily used, and even with the high clearing point, has the comparatively good compatibility with other liquid crystal compounds. A composition containing compound (5) is stable under conditions in which the device is ordinarily used. Accordingly, in the composition containing compound (5), the temperature range of the optically isotropic liquid crystal phase can be extended, and compound (5) can be used in the form of the display device in the wide temperature range. Compound (5) is also useful as a component for decreasing the drive voltage of the composition driven in the optically isotropic liquid crystal phase. If a blue phase is developed in the composition containing the chiral agent and compound (5) in the preferred aspect, a uniform blue phase without coexistence with an N* phase or an isotropic phase is formed. Thus, the composition containing compound (5) in the preferred aspect is easy to develop the uniform blue phase. If compound (5) is used, the clearing point of the liquid crystal composition tends to increase.

In compound (5), compounds (5-1) to (5-4) are preferably used, and compounds (5-1) to (5-3) are further preferably used. In the compounds, compounds (5-1-1), (5-1-2), (5-2-1) to (5-2-4), (5-3-1) or (5-3-2) are particularly preferably used, and compound (5-2-1), (5-2-2) or (5-3-2) is most preferably used.

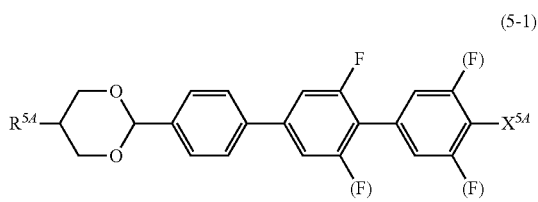

(5-1)

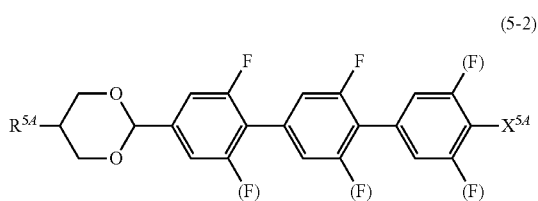

(5-2)

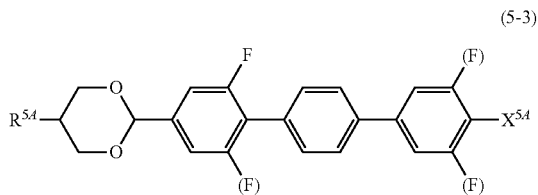

(5-3)

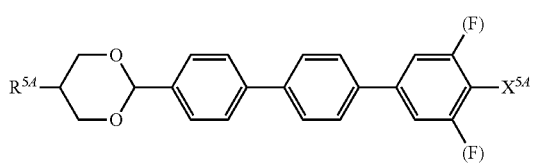

(5-4)

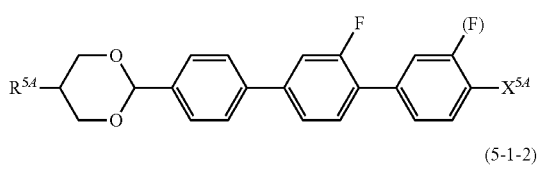

(5-1-1)

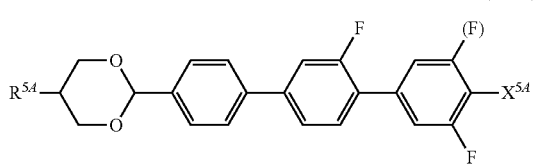

(5-1-2)

-continued

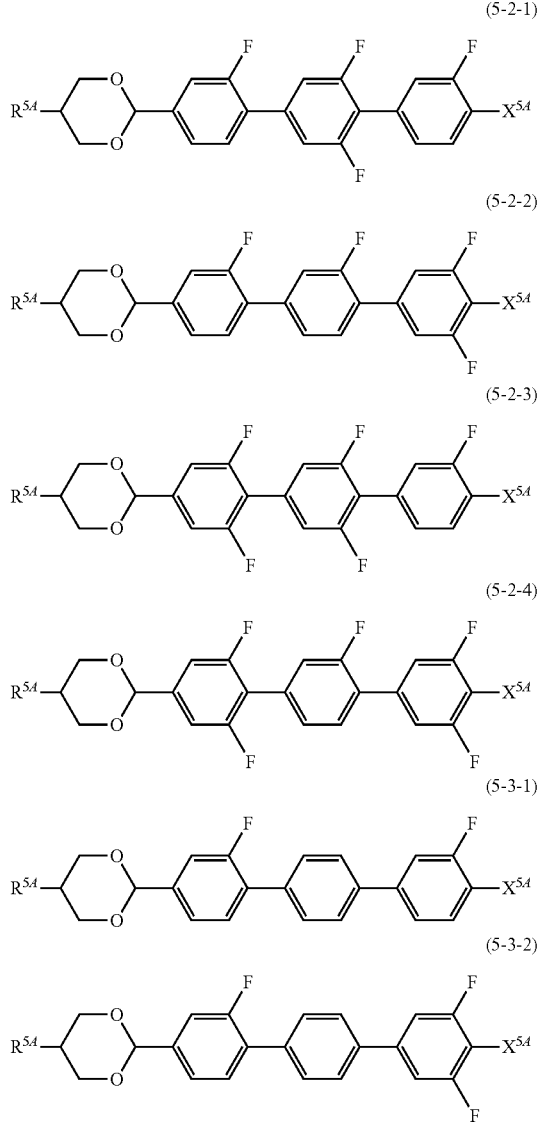

(In the formulas, $R^{5A}$ is alkyl having 1 to 12 carbons, alkenyl having 2 to 12 carbons or alkoxy having 1 to 11 carbons; (F) is independently hydrogen or fluorine; and $X^{5A}$ is fluorine, chlorine, —CF or —OCF$_3$.).

Compound (5) is suitable for preparation of the composition having the large dielectric anisotropy. In order to increase the clearing point, compound (5) is contained preferably in about 1.0% by weight or more in total based on the total weight of the achiral component T. Moreover, in order to decrease the minimum temperature of the liquid crystal phase, compound (5) is contained preferably in about 1% by weight to 50% by weight in total based on the total weight of the achiral component T. Further, based on the total weight of the achiral component T, compound (5) is contained preferably in about 1% by weight to 25% by weight in total, and further preferably in 1% by weight to 15% by weight.

2-6-1 Compound (6)

The achiral component T of the invention may also contain at least one compounds (6) in addition to compound (1). Moreover, for example, the liquid crystal composition of the invention may also contain at least one of compounds (2) to (5) and (7) in addition to compound (1) and compound (6).

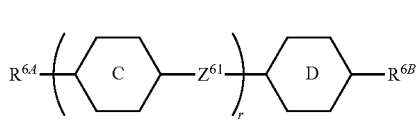

Here, r in compound (6) is 1, 2 or 3.

A compound in which r is 1 in compound (6) is effective mainly in adjusting the viscosity or the refractive index anisotropy, and a compound in which r is 2 or 3 is effective in extending the temperature range of the optically isotropic liquid crystal phase, such as increasing the clearing point, or effective in adjusting the refractive index anisotropy.

If a content of the compound represented by formula (6) is increased, the drive voltage of the liquid crystal composition is increased and the viscosity is decreased. Therefore, as long as a desired value of the viscosity of the liquid crystal composition is fulfilled, the content is desirably as low as possible from a viewpoint of the drive voltage. The content of compound (6) in the achiral component T is preferably 0% by weight to 40% by weight, based on the total weight of the achiral component T, further preferably 1% by weight to 40% by weight thereon, and particularly preferably 1% by weight to 20% by weight thereon.

$R^{6A}$ and $R^{6B}$ are each independently alkyl having 1 to 12 carbons, alkenyl having 2 to 12 carbons, alkoxy having 1 to 12 carbons, or alkenyl having 2 to 12 carbons in which at least one piece of hydrogen is replaced by fluorine. In order to decrease the viscosity of compound (6), $R^{6A}$ and $R^{6B}$ in compound (6) is preferably alkenyl having 2 to 12 carbons. In order to increase the stability to ultraviolet light or in order to increase the stability to heat, $R^{6A}$ and $R^{6B}$ are preferably alkyl having 1 to 12 carbons.

Alkyl in $R^{6A}$ and $R^{6B}$ is preferably ethyl, propyl, butyl, pentyl or heptyl in order to decrease the viscosity.

Alkoxy in $R^{6A}$ and $R^{6B}$ is preferably methoxy or ethoxy in order to decrease the viscosity.

In $R^{6A}$ and $R^{6B}$, alkenyl in which at least one piece of hydrogen is replaced by fluorine is preferably 2,2-difluorovinyl, 3,3-difluoro-2-propenyl, 4,4-difluoro-3-butenyl, 5,5-difluoro-4-pentenyl and 6,6-difluoro-5-hexenyl.

In order to decrease the viscosity of the composition containing compound (6), $R^{6A}$ and $R^{6B}$ are preferably 2,2-difluorovinyl and 4,4-difluoro-3-butenyl.

Rings C and D are independently 1,4-cyclohexylene, 1,4-phenylene, 2-fluoro-1,4-phenylene, 3-fluoro-1,4-phenylene or 2,5-difluoro-1,4-phenylene, and when r is 2 or more, at least two of rings C thereamong may be identical or different. In order to increase the optical anisotropy of compound (6), ring C and ring D are preferably 1,4-phenylene or 3-fluoro-1,4-phenylene. In order to decrease the viscosity of compound 6, ring C and ring D are preferably 1,4-cyclohexylene.

$Z^{61}$ in compound (6) is each independently a single bond, ethylene, —COO— or —OCO—, and when r is 2 or more, at least two pieces of $Z^{61}$ thereamong may be identical or different. Preferred $Z^{61}$ is a single bond in order to decrease the viscosity.

Compound (6) has a small absolute value of dielectric anisotropy, and is a compound close to neutrality.

In compound (6), compounds represented by formulas (6-1) to (6-13) are preferably used.

(In the formulas, $R^{6A}$ and $R^{6B}$ are independently alkyl having 1 to 12 carbons, alkenyl having 2 to 12 carbons, alkoxy having 1 to 11 carbons, or alkenyl having 2 to 12 carbons in which at least one piece of hydrogen is replaced by fluorine.).

In the compounds, compounds (6-1) to (6-3) have the comparatively low viscosity, compounds (6-4) to (6-8) have the comparatively high clearing point, and compounds (6-9) to (6-13) have the comparatively high clearing point.

Compound (6) is used for decreasing the viscosity or increasing the clearing point, when necessary. However, compound (6) increases the drive voltage. Therefore, when the drive voltage is regarded as important, compound (6) is preferably not used or used only in a small amount. Compound (6) is contained preferably in 0% by weight to 30% by weight in total, further preferably in 0% by weight to 20% by weight in total, and particularly preferably in 0% by weight to 10% by weight in total.

2-7-1 Compound (7)

The achiral component T of the invention may also contain at least one compound (7) in addition to compound (1). The liquid crystal composition of the invention may also contain at least one compound selected from compounds (2) to (6) in addition to compound (1) and compound (7).

In compound (7), $R^7$ is hydrogen or alkyl having 1 to 12 carbons, at least one piece of —$CH_2$— in $R^7$ may be replaced by —O—, —S—, —COO— or —OCO—, at least one piece of —$CH_2$—$CH_2$— in R may be replaced by —CH=CH—, —CF=CF— or —C≡C—, and at least one piece of hydrogen in $R^7$ may be replaced by fluorine or chlorine, however, in $R^7$, a case where —O— and —CH=CH— are adjacent is excluded, and a case where —CO— and —CH=CH— are adjacent is excluded. $R^7$ is preferably alkyl having 1 to 12 carbons.

$L^{71}$ to $L^{78}$ are each independently hydrogen or fluorine. In compound (7) in which $L^{72}$ is hydrogen, the compatibility with other compound is good. In compound (7) in which $L^{77}$ and $L^{78}$ are fluorine, the dielectric anisotropy is large, and such a compound is preferred.

$Z^{71}$, $Z^{72}$ and $Z^{73}$ are each independently a single bond, —COO— or —$CF_2O$—. In compound (7) in which any one of $Z^{71}$, $Z^{72}$ and $Z^{73}$ is —$CF_2O$—, the dielectric anisotropy is large and the compatibility with other compounds is good, and such a compound is preferred.

Here, n71 and n72 are each independently 0 or 1. In compound (7) in which n71+n72=2, the dielectric anisotropy is large and the clearing point is high. In compound (7) in which n71+n72=1, the dielectric anisotropy is large and the compatibility with other compounds is good. In compound (7) in which n71+n72=0, the melting point is low, and the viscosity is low.

$X^7$ is hydrogen, halogen, —$SF_5$ or alkyl having 1 to 10 carbons, at least one piece of —$CH_2$— in $X^7$ may be replaced by —O—, —S—, —COO— or —OCO—, at least one piece of —$CH_2$—$CH_2$— in $X^7$ may be replaced by —CH=CH—, —CF=CF— or —C≡C—, and at least one piece of hydrogen in $X^7$ may be replaced by fluorine or chlorine, however, in $X^7$, a case where —O— and —CH=CH— are adjacent is excluded, and a case where —CO— and —CH=CH— are adjacent is excluded.

Specific examples of alkyl in which at least one piece of hydrogen is replaced by fluorine in $X^7$ include —$CHF_2$, —$CF_3$, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$ and —$CHFCF_2CF_3$.

Specific examples of alkoxy in which at least one piece of hydrogen is replaced by fluorine in $X^7$ include —$OCHF_2$, —$OCF_3$, —$OCF_2CH_2F$, —$OCF_2CHF_2$, —$OCH_2CF_3$, —O—$(CF_2)_3$—F, —$OCF_2CHFCF_3$ and —$OCHFCF_2CF_3$.

Specific examples of alkenyl in which at least one piece of hydrogen is replaced by fluorine in $X^7$ include —CH=$CF_2$, —CF=CHF, —CH=$CHCH_2F$, —CH=$CHCF_3$, —$(CH_2)_2$—CH=$CF_2$, —$CH_2CH$=$CHCF_3$ and —CH=$CHCF_2CF_3$.

Specific preferred examples of $X^7$ include fluorine, chlorine, —$CF_3$, —$CHF_2$, —$OCF_3$ and —$OCHF_2$, and fluorine, chlorine, —$CF_3$ and —$OCF_3$ are further preferred. When $X^7$ is chlorine or fluorine, the melting point of compound (7) is comparatively low and the compatibility with other liquid crystal compounds is particularly good. When $X^7$ is —$CF_3$, —$SF_5$, —$CHF_2$, —$OCF_3$ and —$OCHF_2$, compound (7) shows the comparatively large dielectric anisotropy.

When $X^7$ is fluorine, —$CF_3$ or —$OCF_3$, compound (7) is chemically stable.

Compound (7) has a dioxane ring and two to four phenylene rings, and at least one piece of —$CF_2O$— or —COO— linking group. Compound (7) is significantly stable physically and chemically under conditions in which the device is ordinarily used, and even with the high clearing point, the compatibility with other liquid crystal compounds is comparatively good. A composition containing compound (7) is comparatively stable under the conditions in which the device is ordinarily used. Therefore, in the composition containing compound (7), the temperature range of the optically isotropic liquid crystal phase can be extended, and the composition can be used in the form of the display device in the wide temperature range. Further, compound 7 is useful as the component for decreasing the drive voltage of the composition driven in the optically isotropic liquid crystal phase. Moreover, if the blue phase is developed in the composition containing compound (7) and the chiral agent, the uniform blue phase without coexistence with the N* phase or the isotropic phase is easily formed. More specifically, compound (7) is a compound easy to develop the uniform blue phase. Moreover, the significantly large dielectric anisotropy is also developed.

In compound (7), compounds represented by compounds (7-1) to (7-8) are preferably used, compounds (7-1-1), (7-1-2), (7-2-1) to (7-2-7), (7-3-1) to (7-3-4), (7-4-1), (7-5-1) or (7-5-2) are further preferably used, compounds (7-2-1) to (7-2-7) are still further preferably used and compound (7-2-2-E), (7-2-5-E), (7-2-7-E), (7-2-2-F), (7-2-5-F), (7-2-6-F) or (7-2-7-F) is particularly preferably used.

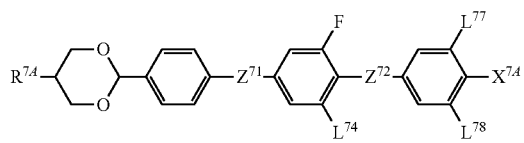

(7-1)

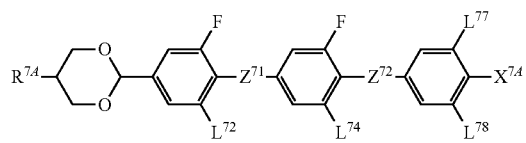

(7-2)

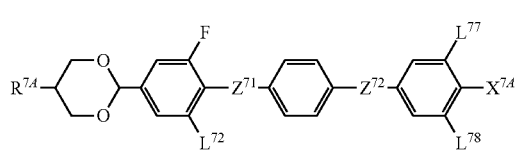

(7-3)

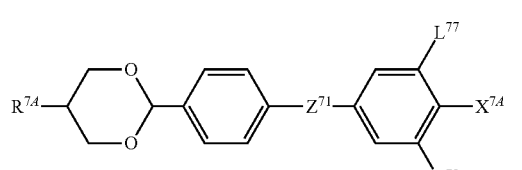

(7-4)

(7-5)
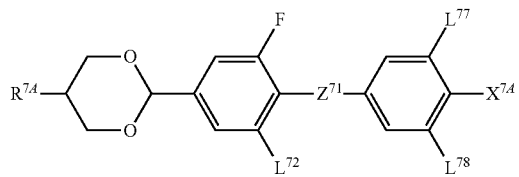
(7-6)
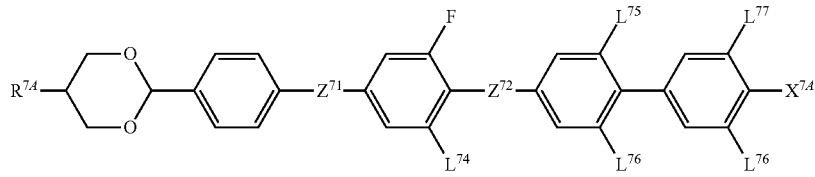
(7-7)
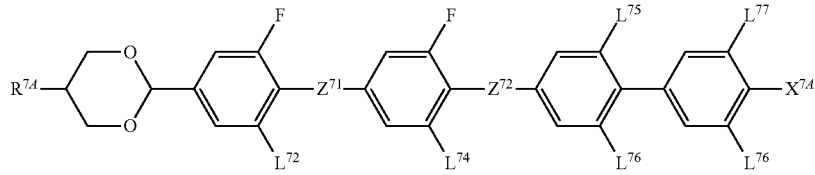
(7-8)
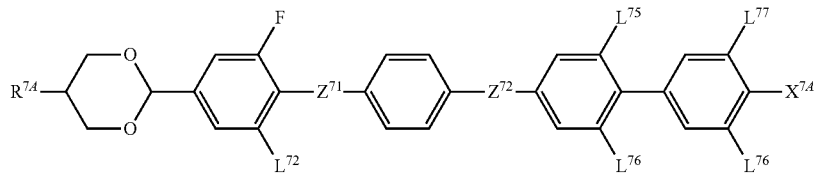
(7-1-1)
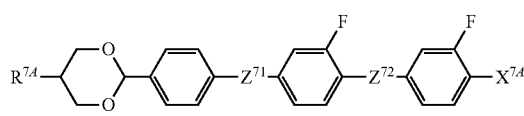
(7-1-2)
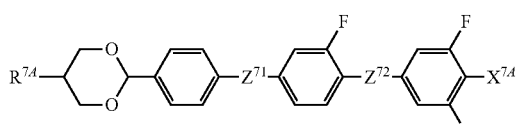
(7-2-1)
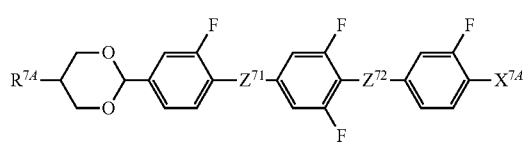
(7-2-2)
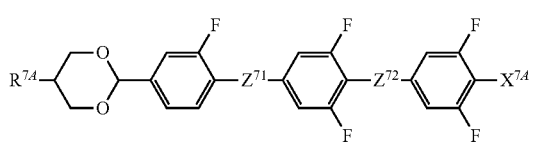
(7-2-3)
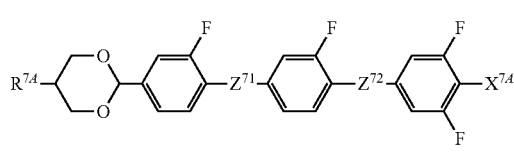
(7-2-4)
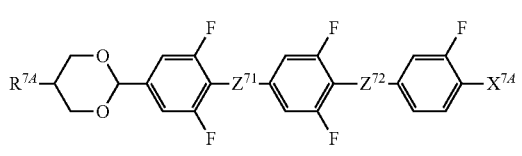
(7-2-5)
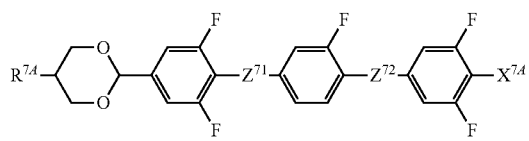
(7-2-6)
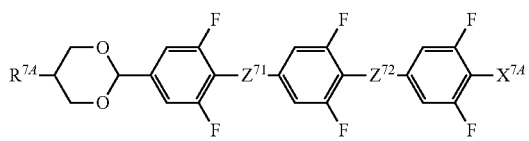
(7-2-7)
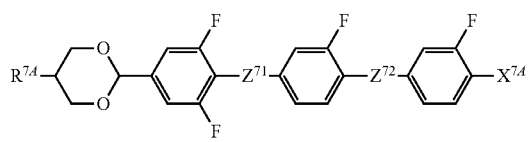
(7-3-1)
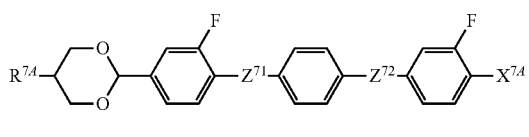

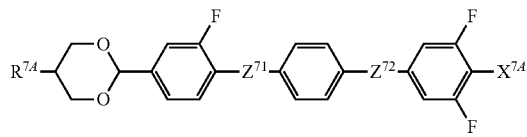
(7-3-2)

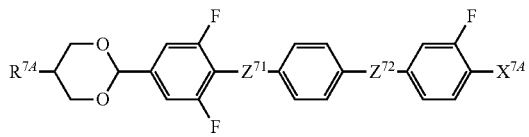
(7-3-3)

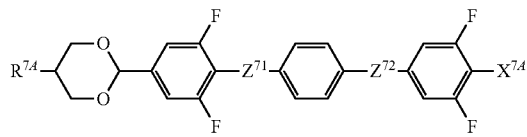
(7-3-4)

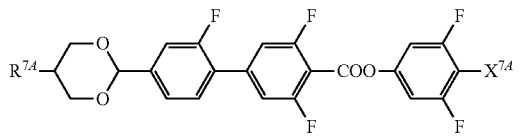
(7-2-2-E)

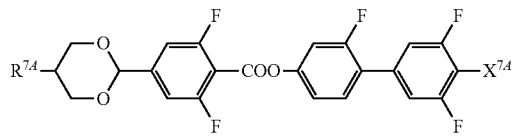
(7-2-5-E)

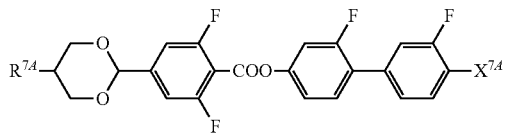
(7-2-7-E)

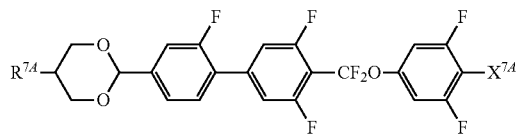
(7-2-2-F)

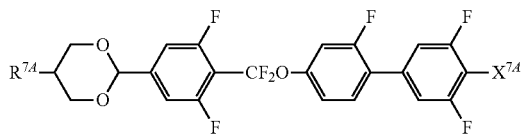
(7-2-5-F)

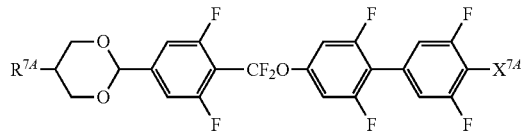
(7-2-6-F)

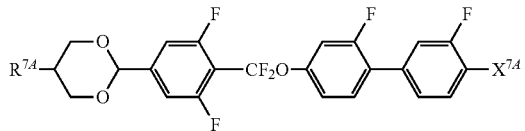
(7-2-7-F)

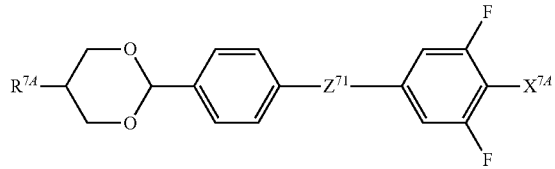
(7-4-1)

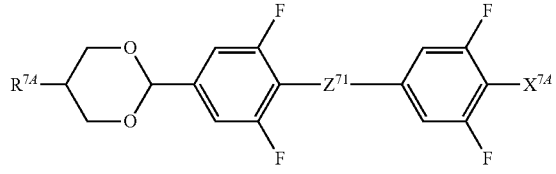
(7-5-1)

(7-5-2)

(In the formulas, $R^{74}$ is alkyl having 1 to 12 carbons, alkenyl having 2 to 12 carbons, alkoxy having 1 to 11 carbons, or alkenyl having 2 to 12 carbons in which at least one piece of hydrogen is replaced by fluorine; $X^{74}$ is fluorine, chlorine, —$CF_3$ or —$OCF_3$; $Z^{71}$ and $Z^{72}$ are each independently a single bond, —COO— or —$CF_2O$—, but at least one of $Z^{71}$ and $Z^{72}$ is —COO— or —$CF_2O$—.)

Compound (7) is suitable for preparing the composition having the large dielectric anisotropy, and can decrease the drive voltage of the device of the invention. Based on the total weight of the achiral component T, compound (7) is contained preferably in 5% by weight to 80% by weight in total, further preferably in 20% by weight to 75% by weight in total, and particularly preferably in 30% by weight to 70% by weight in total.

3 Optically Isotropic Liquid Crystal Composition

The liquid crystal composition of the invention contains the achiral component T and the chiral agent, and includes an aspect of the composition that develops the optically isotropic liquid crystal phase (optically isotropic liquid crystal composition).

3-1 Achiral Component T

The achiral component T contained in the optically isotropic liquid crystal composition of the invention contains compound (1), and at least one of compounds (2) to (7), when necessary.

3-2 Chiral Agent

The chiral agent contained in the optically isotropic liquid crystal composition or the like according to the invention is an optically active compound, and preferably composed of a compound selected from compounds having no radically polymerizable group.

As the chiral agent used in the liquid crystal composition of the invention, a compound having a large helical twisting power is preferred. In the compound having the large helical twisting power, an amount of addition required for obtaining a desired pitch can be minimized, and therefore a rise of the drive voltage can be suppressed, and such a compound is advantageous in practical use. Specifically, compounds represented by compounds (K1) to (K7) are preferred. In addition, in compounds (K4) to (K7), a binaphthyl group or an octahydronaphthyl group is an optically active moiety, and chirality of the chiral agent does not matter.

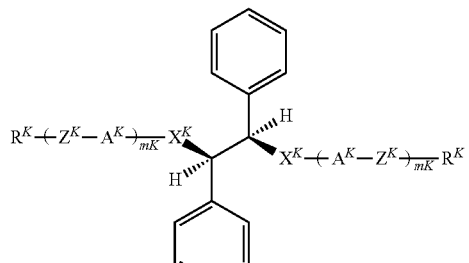
(K1)

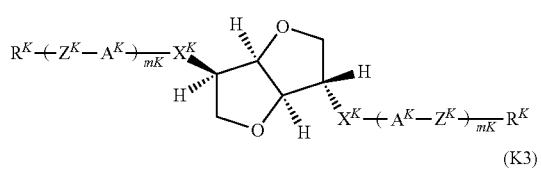
(K2)

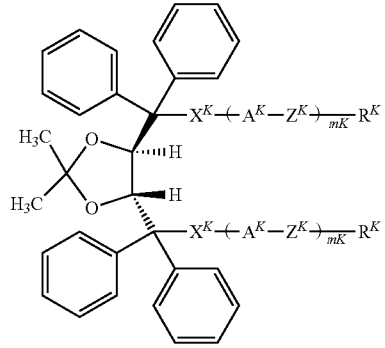
(K3)

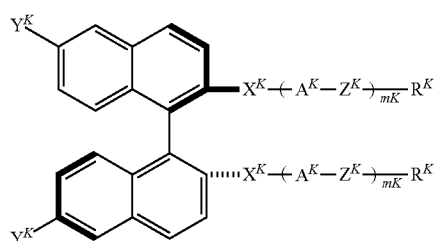
(K4)

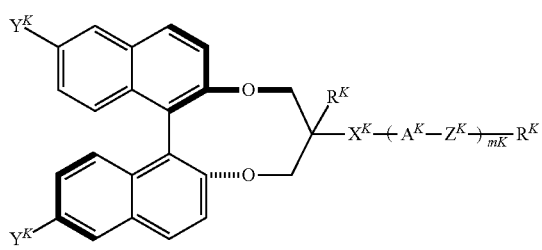
(K5)

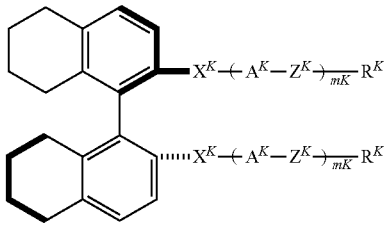
(K6)

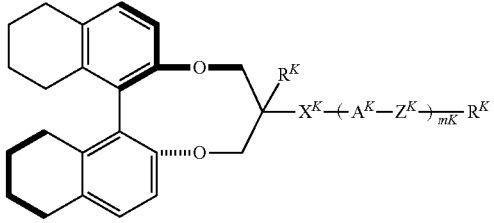
(K7)

(wherein, in the formulas, $R^K$ is each independently hydrogen, halogen, —C≡N, —N=C=O, —N=C=S or alkyl having 1 to 12 carbons, at least one piece of —CH$_2$— in $R^K$ may be replaced by —O—, —S—, —COO— or —OCO—, at least one piece of —CH$_2$—CH$_2$— in $R^K$ may be replaced by —CH=CH—, —CF=CF— or —C≡C—, and at least one piece of hydrogen in $R^K$ may be replaced by fluorine or chlorine;

$A^K$ is each independently an aromatic 6-membered to 8-membered ring, a non-aromatic 3-membered to 8-membered ring or a condensed ring having 9 or more carbons, and at least one piece of hydrogen of the rings may be replaced by halogen, alkyl or haloalkyl having 1 to 3 carbons, —CH$_2$— of the rings may be replaced by —O—, —S— or —NH—, and —CH= may be replaced by —N=;

$Y^K$ is each independently hydrogen, halogen, alkyl having 1 to 3 carbons, haloalkyl having 1 to 3 carbons, an aromatic 6-membered to 8-membered ring, a non-aromatic 3-membered to 8-membered ring or a condensed ring having 9 or more carbons, and at least one piece of hydrogen of the rings may be replaced by halogen, alkyl or haloalkyl having 1 to 3 carbons, —CH$_2$— in the alkyl may be replaced by —O—, —S— or —NH—, and —CH= may be replaced by —N=;

$Z^K$ is each independently a single bond or alkylene having 1 to 8 carbons, at least one piece of —CH$_2$— in $Z^K$ may be replaced by —O—, —S—, —COO—, —OCO—, —CSO—, —OCS—, —N=N—, —CH=N— or —N=CH—, at least one piece of —CH$_2$—CH$_2$— in $Z^K$ may be replaced by —CH=CH—, —CF=CF— or —C≡C—, and at least one piece of hydrogen of $Z^K$ may be replaced by halogen;

$X^K$ is each independently a single bond, —COO—, —OCO—, —CH$_2$O—, —OCH$_2$—, —CF$_2$O—, —OCF$_2$— or —CH$_2$CH$_2$—; and mK is each independently an integer from 1 to 3).

In the compounds, compounds (K4-1) to (K4-6), (K5-1) to (K5-3), (K6-1) to (K6-6) and (K7-1) to (K7-6) are preferred as the chiral agent added to the liquid crystal composition, and compounds (K4-5), (K5-1) to (K5-3), (K6-5) to (K6-6) are further preferred.

(K4-1) 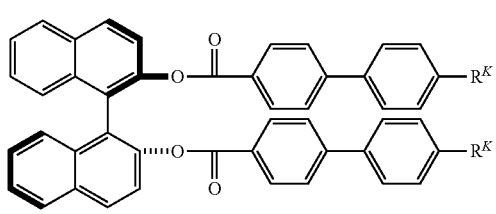
(K4-2) 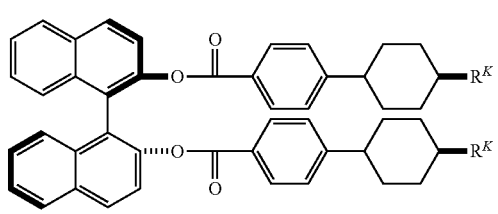
(K4-3) 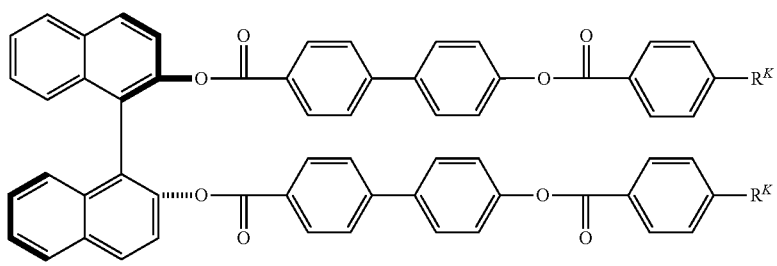
(K4-4) 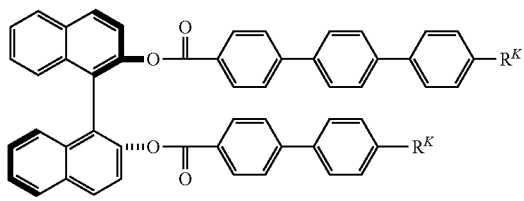
(K4-5) 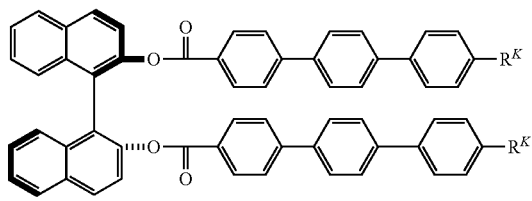
(K4-6) 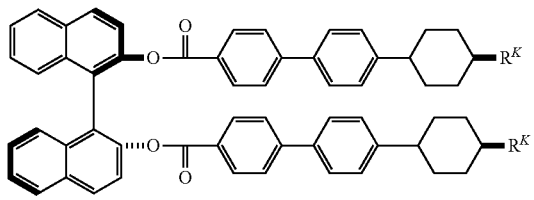
(K5-1) 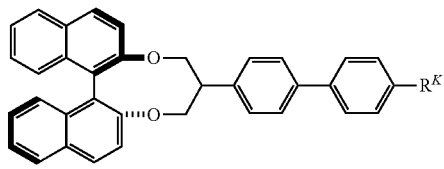
(K5-2) 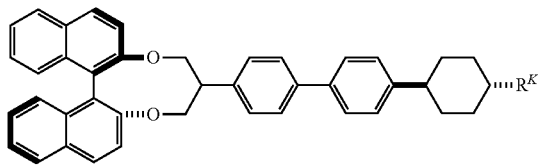
(K5-3) 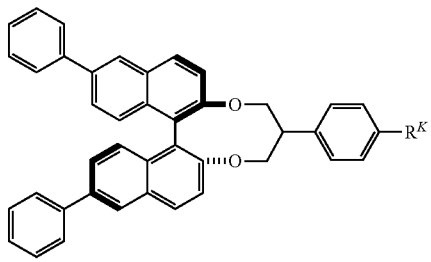
(K6-1) 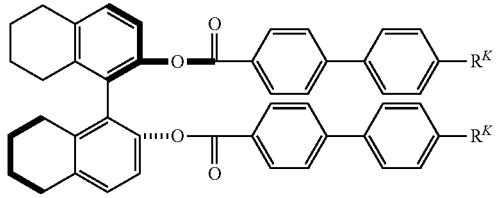
(K6-2) 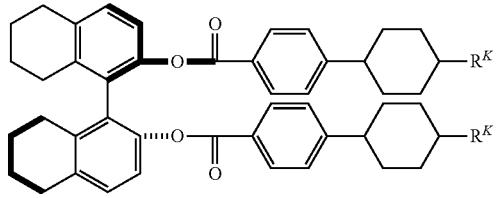

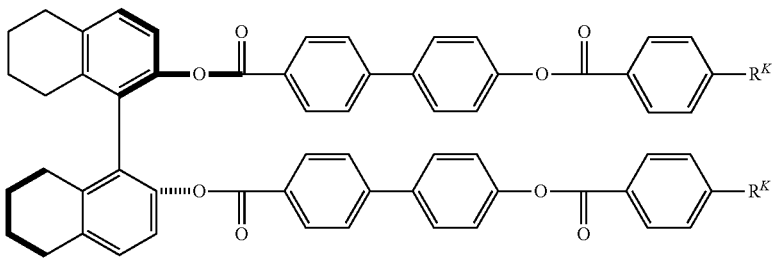
(K6-3)

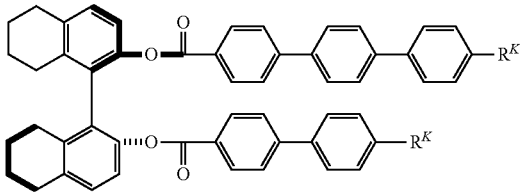
(K6-4)

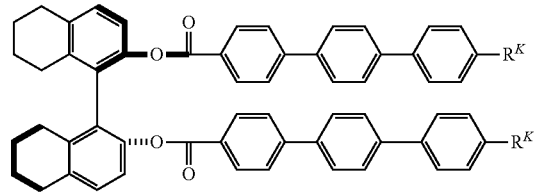
(K6-5)

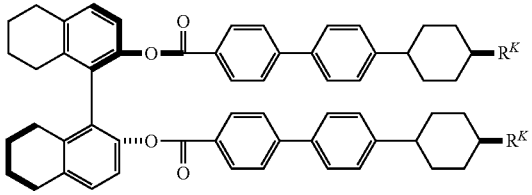

(K6-6)

($R^K$ in the formulas has a meaning identical with $R^K$ in formulas (K1) to (K7)).

As the chiral agent to be contained in the liquid crystal composition, one compound may be used or two or more compounds may be used.

In order to facilitate development of the optically isotropic liquid crystal phase, based on the total weight of the liquid crystal composition of the invention, the chiral agent is contained preferably in 1 to 40% by weight, further preferably in 3 to 25% by weight, and particularly preferably in 3 to 15% by weight.

3-3 Optically Isotropic Liquid Crystal Phase

An expression "liquid crystal composition has optical isotropy" herein means that the liquid crystal composition exhibits the optical isotropy macroscopically because arrangement of liquid crystal molecules is isotropic, in which liquid crystal order is microscopically present. "Pitch based on the liquid crystal order of the liquid crystal composition microscopically (hereinafter, occasionally referred to as a pitch)" is preferably 700 nanometers or less, further preferably 500 nanometers or less, and most preferably 350 nanometers or less.

"Non-liquid crystal isotropic phase" herein means a generally defined isotropic phase, more specifically, a disordered phase, and an isotropic phase in which, even if an area in which a local order parameter is not zero is produced, the area is caused by a fluctuation. For example, the isotropic phase developed on a side of a higher temperature of the nematic phase corresponds to the non-liquid crystal isotropic phase herein. A similar definition is applied to chiral liquid crystals herein.

"Optically isotropic liquid crystal phase" herein represents a phase that develops the optically isotropic liquid crystal phase, and not by the fluctuation. One example includes a phase that develops a platelet texture (blue phase in a narrow sense).

Unless otherwise noted, the nematic phase herein means the nematic phase including no chiral nematic phase in the narrow sense.

In the optically isotropic liquid crystal composition according to the invention, the platelet texture typical to the blue phase is not occasionally observed under observation by means of a polarizing microscope, although the liquid crystal composition has the optically isotropic liquid crystal phase. Then, the phase that develops the platelet texture is herein referred to as the blue phase, and the optically isotropic liquid crystal phase including the blue phase is referred to as the optically isotropic liquid crystal phase. More specifically, the blue phase is included in the optically isotropic liquid crystal phase.

In general, the blue phases are classified into three kinds, namely, blue phase I, blue phase II and blue phase III, and all of the three kinds of blue phases are optically active, and isotropic. In the blue phase of blue phase I or blue phase II, two or more kinds of diffracted light resulting from Bragg reflection from different lattice planes are observed. The blue phase is generally observed between the non-liquid crystal isotropic phase and a chiral nematic phase.

"State in which the optically isotropic liquid crystal phase does not show diffracted light having two or more colors" means that the optically isotropic liquid crystal phase has almost monochrome in everywhere in which the platelet texture to be observed in blue phase I and blue phase II is not observed. In the optically isotropic liquid crystal phase that shows no diffracted light having two or more colors, uniformity of contrast in the plane is unnecessary.

The optically isotropic liquid crystal phase that shows no diffracted light having two or more colors has advantages in which intensity of reflected light by Bragg reflection is suppressed, or reflection is shifted to a side of a lower wavelength.

Moreover, in a liquid crystal medium that reflects visible light, color may occasionally become a problem when the liquid crystal material is utilized in the form of the display device. However, in the liquid crystals that show no diffracted light having two or more colors, the reflection wavelength is shifted to the side of the lower wavelength. Therefore, reflection of visible light is allowed to disappear by a pitch longer than a pitch of the blue phase in the narrow sense (phase that develops the platelet texture).

In the liquid crystal composition containing the achiral component T and the chiral agent according to the invention, the chiral agent is added preferably at a concentration to be 700 nanometers or less in the pitch. In addition, the composition that develops the nematic phase contains compound 1, and when necessary, other components.

Moreover, the optically isotropic liquid crystal composition according to the invention can also be obtained by adding the chiral agent to the composition having the chiral nematic phase and no optically isotropic liquid crystal phase. In addition, the composition having the chiral nematic phase and no optically isotropic liquid crystal phase contains compound 1, the optically active compound, and when necessary, other components. On the above occasion, in order to allow no development of the optically isotropic liquid crystal phase, the chiral agent is added preferably at a concentration to be 700 nanometers in the pitch. Here, as the chiral agent to be added, the compounds (K1) to (K7) having large helical twisting power as described later can be used, and compounds (K2-1) to (K2-8), (K4-1) to (K4-6), (K5-1) to (K5-3), (K6-1) to (K6-6) or (K7-1) to (K7-2) are further preferably used.

The temperature range in which the liquid crystal composition of the preferred aspect according to the invention develops the optically isotropic liquid crystal phase can be extended by adding the chiral agent to the liquid crystal composition in which the temperature range of coexistence of the nematic phase or the chiral nematic phase and the isotropic phase is wide to develop the optically isotropic liquid crystal phase. For example, the composition that develops the optically isotropic liquid crystal phase in the wide temperature range can be prepared by mixing a liquid crystal compound having a high clearing point and a liquid crystal compound having a low clearing point to prepare a liquid crystal composition in which the temperature range of coexistence of the nematic phase and the isotropic phase is wide in the wide temperature range, and adding the chiral agent thereto.

As the liquid crystal composition having the wide temperature range of coexistence of the nematic phase or the chiral nematic phase and the isotropic phase, a liquid crystal composition having a difference between the maximum temperature and the minimum temperature in which the chiral nematic phase and the non-liquid crystal isotropic phase coexist is 3 to 150° C. is preferred, and a liquid crystal composition having a difference in the range of 5 to 150° C. is further preferred. A liquid crystal compound having a difference between the maximum temperature and the minimum temperature in which the nematic phase and the non-liquid crystal isotropic phase coexist is 3 to 150° C. is also preferred.

If an electric field is applied to the liquid crystal medium according to the invention in the optically isotropic liquid crystal phase, electric birefringence is caused, but the birefringence does not necessarily result from the Kerr effect.

The electric birefringence in the optically isotropic liquid crystal phase becomes larger accordingly as the pitch becomes longer. Therefore, the electric birefringence can be increased by adjusting a kind and a content of the chiral agent to set a long pitch, as long as a demand for other optical characteristics (transmittance, a diffraction wavelength or the like) is satisfied.

3-4 Any Other Component

The liquid crystal composition according to the invention may further contain a solvent, a monomer, a polymer substance, a polymerization initiator, an antioxidant, an ultraviolet light absorbent, a curing agent, a stabilizer, a dichroic dye, a photochromic compound or the like within the range in which the characteristics of the composition are not significantly influenced.

Specific examples of the dichroic dye to be used in the liquid crystal composition according to the invention include a merocyanine type, a styryl type, an azo type, an azomethine type, an azoxy type, a quinophthalone type, an anthraquinone type and a tetrazine type.

4 Optically Isotropic Polymer/Liquid Crystal Composite Material 4-1 Polymer/Liquid Crystal Composite Material The polymer/liquid crystal composite material according to the invention is a composite material containing the liquid crystal composition and the polymer to optically exhibit isotropy, and can be used in the optical device driven in the optically isotropic liquid crystal phase. The liquid crystal composition contained in the polymer/liquid crystal composite material according to the invention is the liquid crystal composition according to the invention.

"Polymer/liquid crystal composite material" herein is not particularly limited, as long as the composite material contains both the liquid crystal material and the polymer compound, but may be in a state in which the polymer is subjected to phase separation from the liquid crystal material in a state in which the polymer is not partially or wholly dissolved into the liquid crystal material, the solvent or the like.

The optically isotropic polymer/liquid crystal composite material according to the preferred aspect of the invention can develop the optically isotropic liquid crystal phase in the wide temperature range. Moreover, the polymer/liquid crystal composite material according to the preferred aspect of the invention has a significantly high response velocity. Moreover, the polymer/liquid crystal composite material according to the preferred aspect of the invention can be preferably used for the optical device such as the display device, based on the effects.

4-2 Polymer Compound

The composite material according to the invention can be manufactured by mixing the optically isotropic liquid crystal composition and the polymer obtained by allowing polymerization in advance, but is preferably manufactured by mixing a low molecular weight monomer, macro monomer, oligomer or the like (hereinafter, collectively referred to as "monomer or the like") serving as a material of the polymer, and the liquid crystal composition CLC, and then performing a polymerization reaction in the mixture. The mixture containing the monomer or the like and the liquid crystal composition is referred to as "polymerizable monomer/liquid crystal mixture" herein. "Polymerizable monomer/liquid crystal mixture" may contain, when necessary, a polymerization initiator, a curing agent, a catalyst, a stabilizer, a dichroic dye or a photochromic compound or the like as described later in the range in which advantageous effects of the invention are not adversely affected. For example, the polymerizable monomer/liquid crystal mixture according to the invention may contain, when necessary, 0.1 to 20 parts by weight of the polymerization initiator based on 100 parts by weight of the polymerizable monomer. "Polymerizable monomer/liquid crystal mixture" is essentially the liquid crystal medium when the mixture is polymerized in the blue phase, but when the mixture is polymerized in the isotropic phase, the mixture is not necessarily the liquid crystal medium.

A polymerization temperature preferably includes temperature at which the polymer/liquid crystal composite material exhibits high transparency and isotropy. The polymerization temperature further preferably includes temperature at which the mixture of the monomer and the liquid crystal material develops the isotropic phase or the blue phase, and the polymerization is terminated in the isotropic phase or the optically isotropic liquid crystal phase. More specifically, the polymerization temperature is preferably adjusted to temperature at which, after the polymerization, the polymer/liquid crystal composite material does not substantially scatter light on a side of a wavelength longer than a wavelength of visible light, and develops an optically isotropic state.

As a raw material of the polymer that constitutes the composite material according to the invention, a low molecular weight monomer, macromonomer or oligomer can be used, for example. "Raw material monomer of the polymer" herein is used in the meaning including the low molecular weight monomer, macro monomer or oligomer. Moreover, the polymer obtained preferably has a three-dimensional crosslinking structure, and therefore a polyfunctional monomer having two or more polymerizable functional groups is preferably used as the raw material monomer of the polymer. The polymerizable functional group is not particularly limited. Specific examples include an acrylic group, a methacrylic group, a glycidyl group, an epoxy group, an oxetanyl group and a vinyl group, but preferably an acrylic group and a methacrylic group from a viewpoint of a rate of polymerization. Among the raw material monomers of the polymer, if a monomer having two or more polymerizable functional groups is incorporated into the monomer in 10% by weight or more, high-level transparency and isotropy are easily developed in the composite material according to the invention, and therefore such a case is preferred.

In order to obtain a preferred composite material, the polymer preferably has a mesogen moiety, and a raw material monomer having the mesogen moiety can be partially or wholly used as the raw material monomer of the polymer.

4-2-1 Monofunctional, Bifunctional or Trifunctional Monomer Having Mesogen Moiety A monofunctional or bifunctional monomer having the mesogen moiety is not particularly limited structurally, but specific examples include a compound represented by formula (M1) or formula (M2) described below.

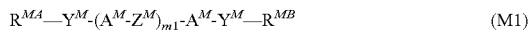

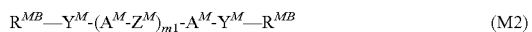

In compound (M1), $R^{MA}$ is hydrogen, halogen, —C≡N, —N=C=O, —N=C=S or alkyl having 1 to 20 carbons, and in the alkyl, at least one piece of —CH$_2$— may be replaced by —O—, —S—, —CO—, —COO— or —OCO—, at least one piece of —CH$_2$—CH$_2$— in the alkyl may be replaced by —CH=CH—, —CF=CF— or —C≡C—, and in the alkyl groups in which at least one piece of —CH$_2$— in the alkyl is replaced by —O—, —S—, —COO— or —OCO— or in the alkyl groups in which at least one piece of —CH$_2$—CH$_2$— in the alkyl is replaced by —CH=CH— or —C≡C—, at least one piece of hydrogen may be replaced by halogen or —C≡N. $R^{MB}$ is each independently a polymerizable group represented by formulas (M3-1) to (M3-7).

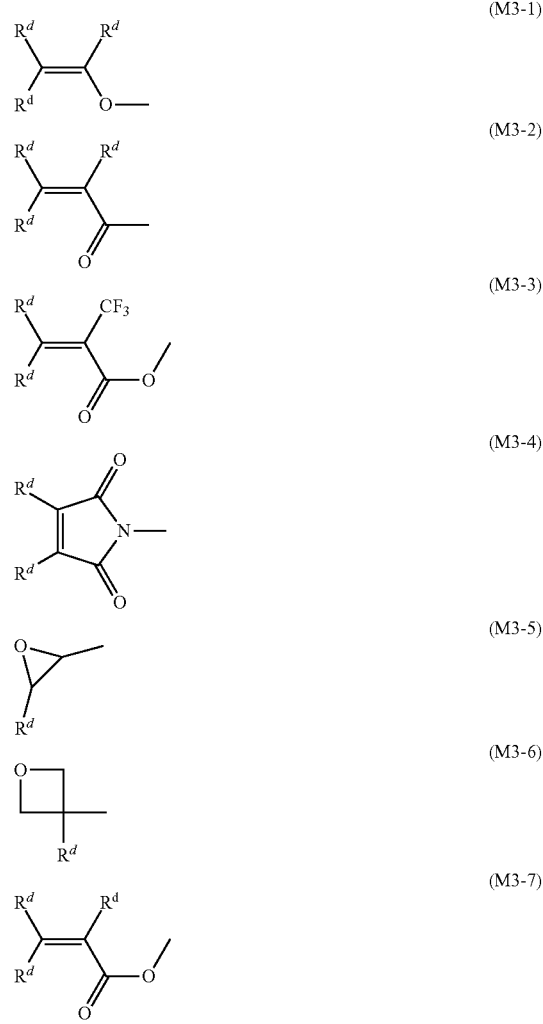

Preferred $R^{MA}$ is hydrogen, halogen, —C≡N, —CF$_3$, —CF$_2$H, —CFH$_2$, —OCF$_3$, —OCF$_2$H, alkyl having 1 to 20 carbons, alkoxy having 1 to 19 carbons, alkenyl having 2 to 21 carbons and alkynyl having 2 to 21 carbons. Particularly preferred $R^a$ is —C≡N, alkyl having 1 to 20 carbons and alkoxy having 1 to 19 carbons.

In compounds (M1) and (M2), $R^{MB}$ is each independently a polymerizable group represented by formulas (M3-1) to (M3-7).

Here, $R^d$ in formulas (M3-1) to (M3-7) is each independently hydrogen, halogen or alkyl having 1 to 5 carbons, and in the alkyl, at least one piece of hydrogen may be replaced by halogen. Preferred $R^d$ is hydrogen, halogen and methyl. Particularly preferred $R^d$ is hydrogen, fluorine and methyl.

Moreover, compounds represented by formulas (M3-2) to (M3-4) and (M3-7) are preferably polymerized according to radical polymerization. Compounds represented by formulas (M3-1), (M3-5) and (M3-6) are preferably polymerized according to cationic polymerization. If a small amount of radicals or cation active species is generated in a reaction system in all, the polymerization starts. The polymerization initiator can be used in order to accelerate generation of the active species. Light or heat can be used for generation of the active species, for example.

In compounds (M1) and (M2), $A^M$ is each independently an aromatic or non-aromatic 5-membered ring or 6-membered-ring or a condensed ring having 9 or more carbons, but —$CH_2$— in the ring may be replaced by —O—, —S—, —NH— or —$NCH_3$—, —CH= in the ring may be replaced by —N=, and a hydrogen atom in the ring may be replaced by halogen, alkyl having 1 to 5 carbons or alkyl halide. Specific examples of preferred $A^M$ include 1,4-cyclohexylene, 1,4-cyclohexenylene, 1,4-phenylene, naphthalene-2,6-diyl, tetrahydronaphthalene-2,6-diyl, fluorene-2,7-diyl or bicyclo[2.2.2]octane-1,4-diyl, and in the rings, at least one piece of —$CH_2$— may be replaced by —O—, at least one piece of —CH= may be replaced by —N=, and in the rings, at least one piece of hydrogen may be replaced by halogen, alkyl having 1 to 5 carbons or alkyl halide having 1 to 5 carbons.

In taking into account the stability of the compound, —$CH_2$—O—$CH_2$—O— in which oxygen and oxygen are not adjacent is further preferred to —$CH_2$—O—O—$CH_2$— in which oxygen and oxygen are adjacent.

In the compounds, particularly preferred $A^M$ is 1,4-cyclohexylene, 1,4-cyclohexenylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-methyl-1,4-phenylene, 2-trifluoromethyl-1,4-phenylene, 2,3-bis(trifluoromethyl)-1,4-phenylene, naphthalene-2,6-diyl, tetrahydronaphthalene-2,6-diyl, fluorene-2,7-diyl, 9-methyl-fluorene-2,7-diyl, 1,3-dioxane-2,5-diyl, pyridine-2,5-diyl or pyrimidine-2,5-diyl. In addition, with regard to a configuration of 1,4-cyclohexylene and 1,3-dioxane-2,5-diyl, trans is preferred to cis.

Because 2-fluoro-1,4-phenylene is structurally identical with 3-fluoro-1,4-phenylene, the latter is not illustrated. A same rule also applies to a relationship between 2,5-difluoro-1,4-phenylene and 3,6-difluoro-1,4-phenylene, or the like.

$Y^M$ is each independently a single bond or alkylene having 1 to 20 carbons, and in the alkylene, at least one piece of —$CH_2$— may be replaced by —O— and —S—, and at least one piece of —$CH_2$—$CH_2$— in the alkyl may be replaced by —CH=CH—, —C≡C—, —COO— or —OCO—. Preferred $Y^M$ is a single bond, —$(CH_2)_{m2}$—, —$O(CH_2)_{m2}$— and —$(CH_2)_{m2}O$— (in the formulas, m2 is an integer from 1 to 20). Particularly preferred $Y^M$ is a single bond, —$(CH_2)_{m2}$—, —$O(CH_2)_{m2}$— and —$(CH_2)_{m2}O$— (in the formula, m2 is an integer from 1 to 10). In taking into account the stability of the compound, —$Y^M$—$R^{MA}$ and —$Y^M$—$R^{MB}$ preferably have neither —O—O—, nor —O—S—, nor —S—O-nor —S—S— in the groups.

$Z^M$ is each independently a single bond, —$(CH_2)_{m3}$—, —$O(CH_2)_{m3}$—, —$(CH_2)_{m3}O$—, —$O(CH_2)_{m3}O$—, —CH=CH—, —C≡C—, —COO—, —OCO—, —$(CF_2)_2$—, —$(CH_2)_2$—COO—, —OCO—$(CH_2)_2$—, —CH=CH—COO—, —OCO—CH=CH—, —C≡C—COO—, —OCO—C≡C—, —CH=CH—$(CH_2)_2$—, —$(CH_2)_2$—CH=CH—, —CF=CF—, —C≡C—CH=CH—, —CH=CH—C≡C—, —$OCF_2$—$(CH_2)_2$—, —$(CH_2)_2$—$CF_2O$—, —$OCF_2$— or —$CF_2O$— (in the formulas, m3 is an integer from 1 to 20).

Preferred $Z^M$ is a single bond, —$(CH_2)_{m3}$—, —$O(CH_2)_{m3}$—, —$(CH_2)_{m3}O$—, —CH=CH—, —C≡C—, —COO—, —OCO—, —$(CH_2)_2$—COO—, —OCO—$(CH_2)_2$—, —CH=CH—COO—, —OCO—CH=CH—, —$OCF_2$— and —$CF_2O$—.

Then, m1 is an integer from 1 to 6. Preferred m1 is an integer from 1 to 3. When m1 is 1, the formula represents a bicyclic compound having two rings such as a 6-membered ring. When m1 is 2 and 3, the formula represents a tricyclic compound and a tetracyclic compound, respectively. For example, when m1 is 1, two pieces of $A^M$ may be identical or different. For example, when m1 is 2, three pieces of $A^M$ (or two pieces of $Z^M$) may be identical or different. When m1 is 3 to 6, a same rule also applies thereto. A same rule also applies to $R^{MA}$, $R^{MB}$, $R^d$, $Z^M$, $A^M$ and $Y^M$.

Even if compounds (M1) and (M2) contain an isotope such as $^2H$ (deuterium) and $^{13}C$ in an amount higher than an amount of natural abundance, compounds (M1) and (M2) have similar characteristics, and therefore can be preferably used.

Further preferred examples of compound (M1) and compound (M2) are compounds (M1-1) to (M1-41) and (M2-1) to (M2-27). In the compounds, definitions of $R^{MA}$, $R^{MB}$, $R^d$, $Z^M$, $A^M$, $Y^M$ and p are identical with the definitions in formula (M1) and formula (M2) described in the aspect of the invention.

The partial structure described below in compounds (M1-1) to (M1-41) and (M2-1) to (M2-27) are described. Partial structure (a1) represents 1,4-phenylene in which at least one piece of hydrogen is replaced by fluorine. Partial structure (a2) represents 1,4-phenylene in which at least one piece of hydrogen may be replaced by fluorine. Partial structure (a3) represents 1,4-phenylene in which at least one piece of hydrogen may be replaced by fluorine or methyl. Partial structure (a4) represents fluorene in which hydrogen in 9-position may be replaced by methyl.

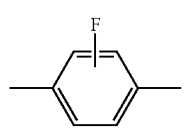
(a1)

(a2)

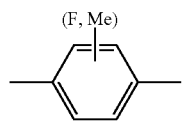
(a3)

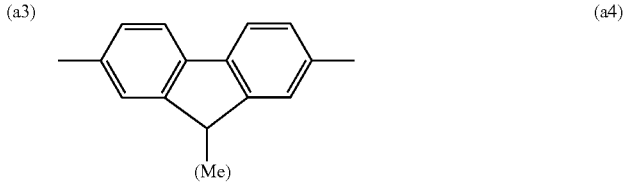
(a4)

-continued
(M1-1) 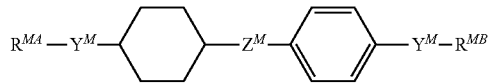
(M1-2) 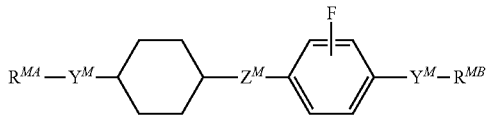
(M1-3) 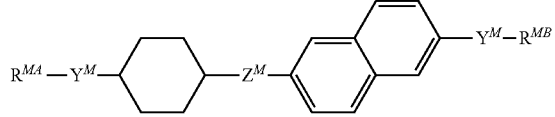
(M1-4) 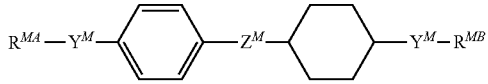
(M1-5) 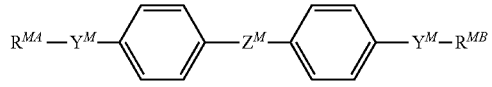
(M1-6) 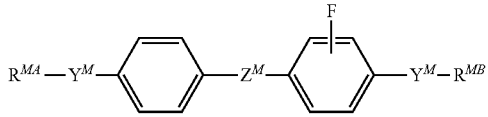
(M1-7) 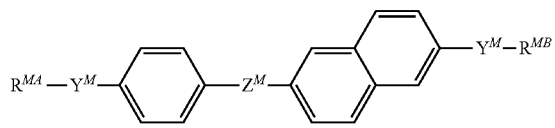
(M1-8) 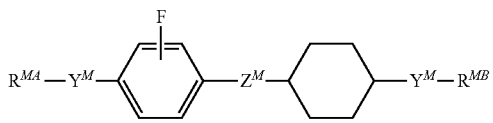
(M1-9) 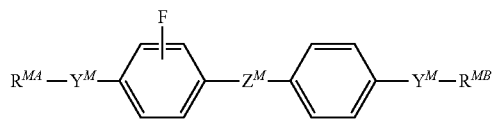
(M1-10) 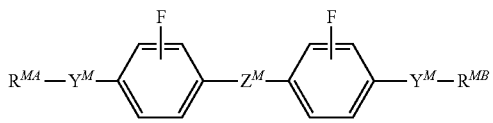
(M1-11) 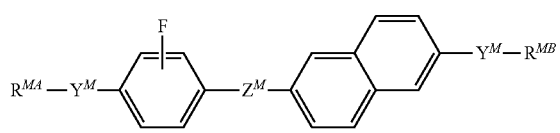
(M1-12) 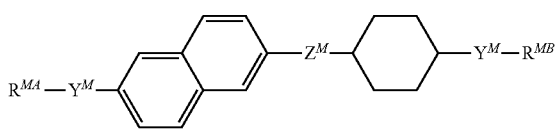
(M1-13) 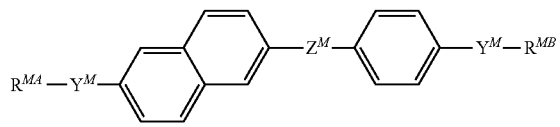
(M1-14) 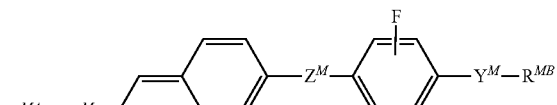
(M1-15) 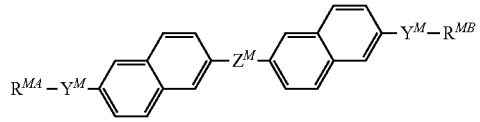
(M1-16) 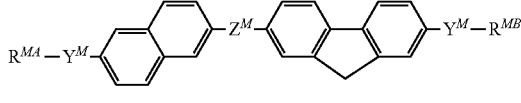
(M1-17) 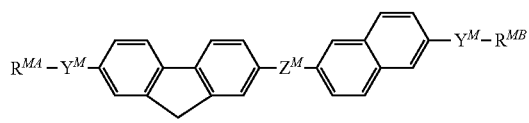
(M1-18) 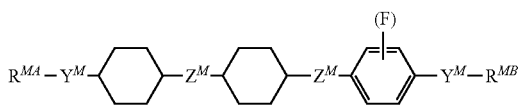
(M1-19) 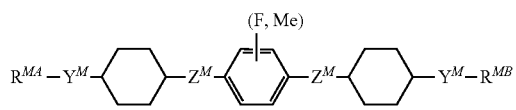
(M1-20) 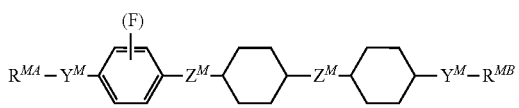
(M1-21) 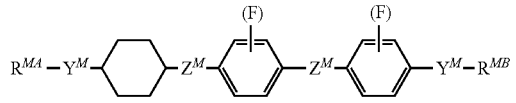
(M1-22) 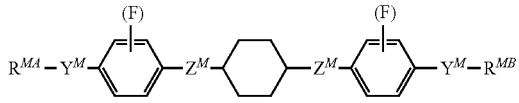

(M1-23) 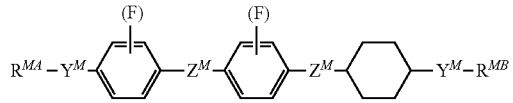
(M1-24) 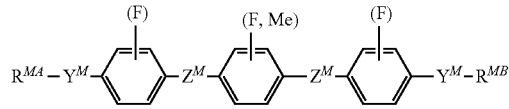
(M1-25) 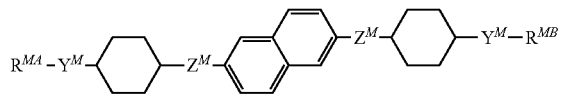
(M1-26) 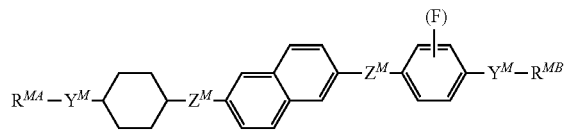
(M1-27) 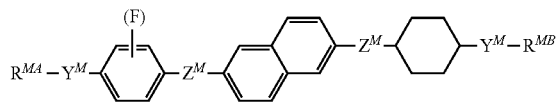
(M1-28)
(M1-29) 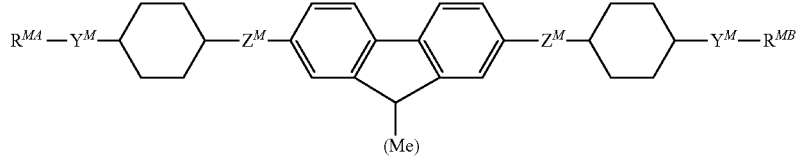
(M1-30) 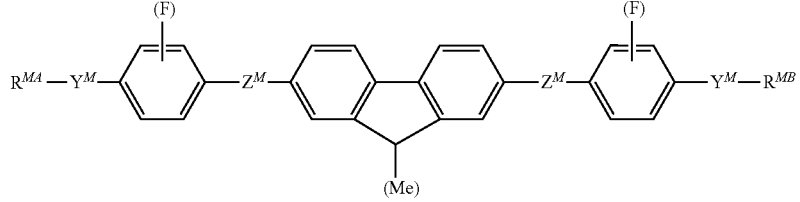
(M1-31) 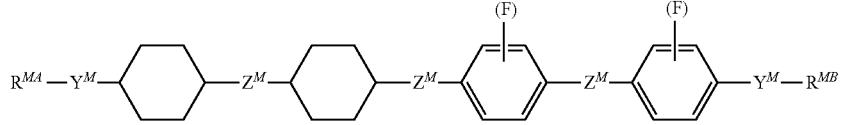
(M1-32) 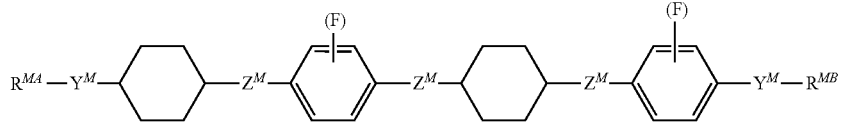
(M1-33) 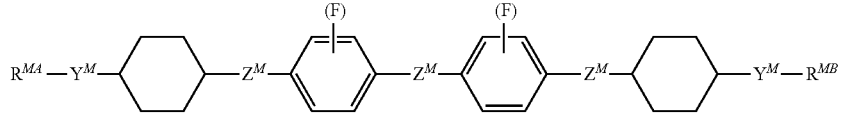
(M1-34) 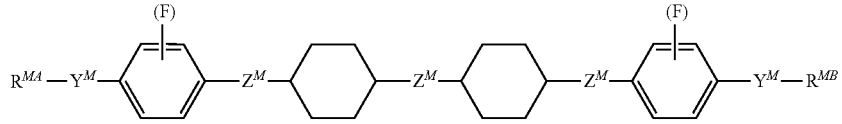
(M1-35)

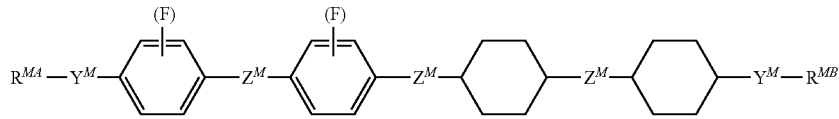
(M1-36)
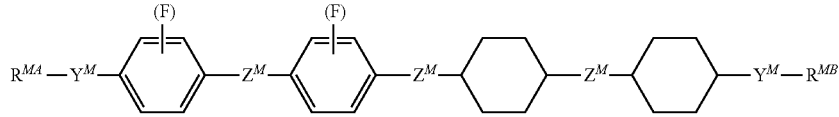
(M1-36)
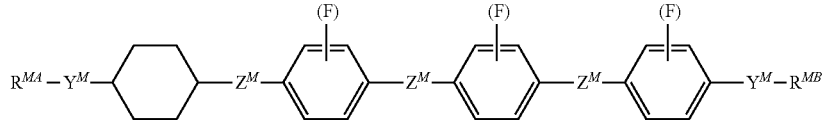
(M1-37)
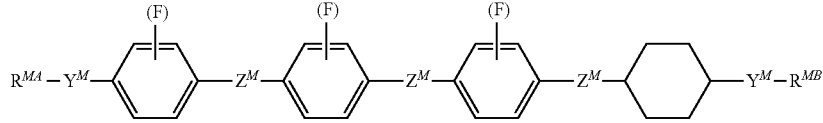
(M1-38)
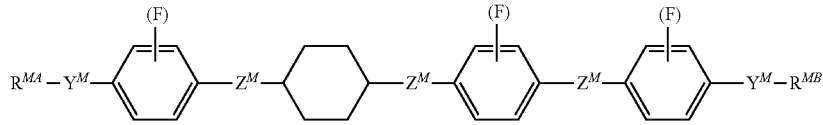
(M1-39)
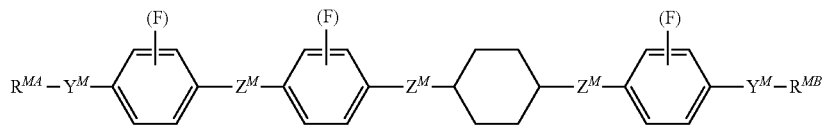
(M1-40)
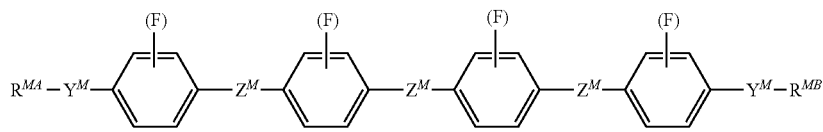
(M1-41)
(M2-1)
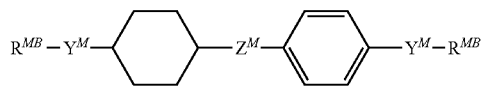
(M2-2)
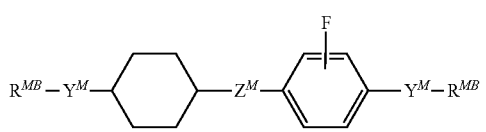
(M2-3)
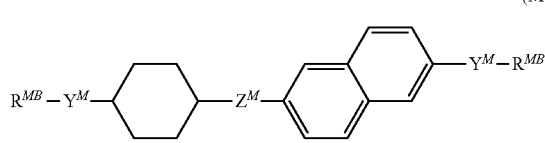
(M2-4)
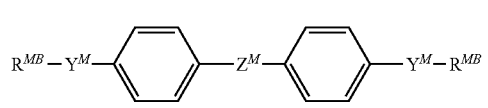
(M2-5)
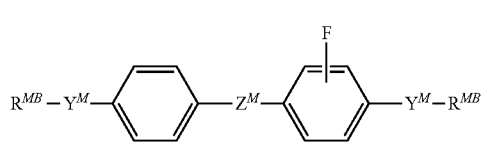
(M2-6)
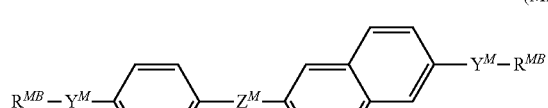
(M2-7)
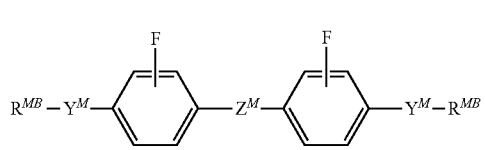
(M2-8)
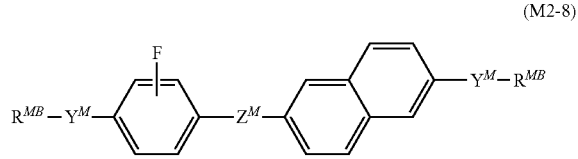

(M2-9)
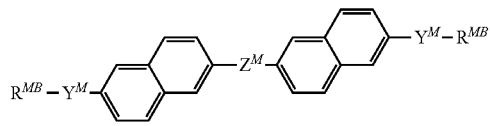
(M2-10)
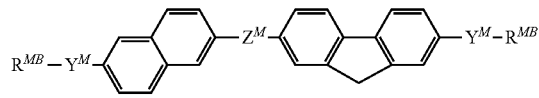
(M2-11)
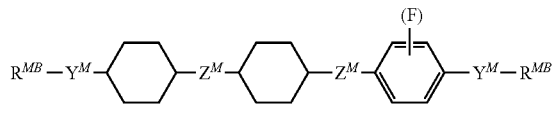
(M2-12)
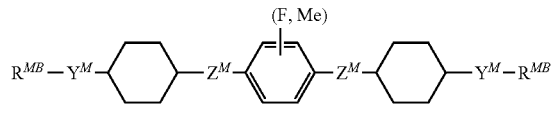
(M2-13)
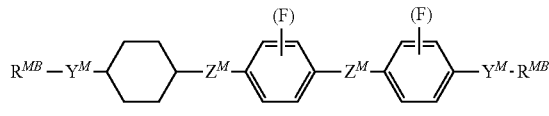
(M2-14)
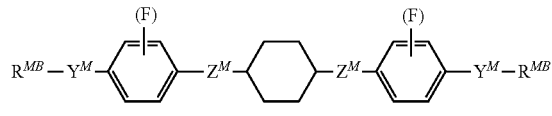
(M2-15)
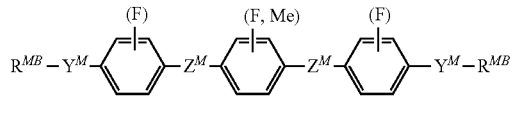
(M2-16)
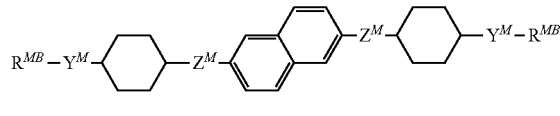
(M2-17)
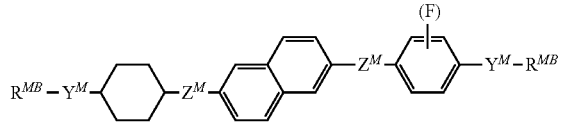
(M2-18)
(M2-19)
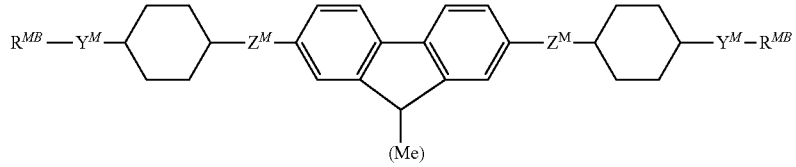
(M2-20)
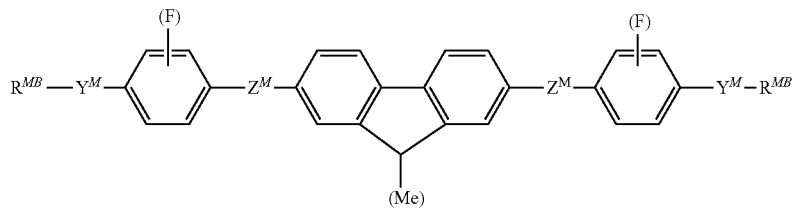
(M2-21)
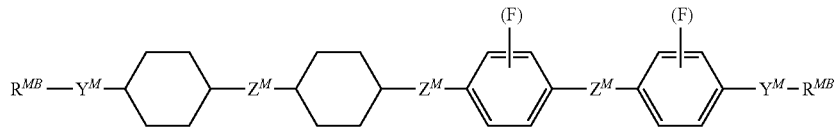
(M2-22)
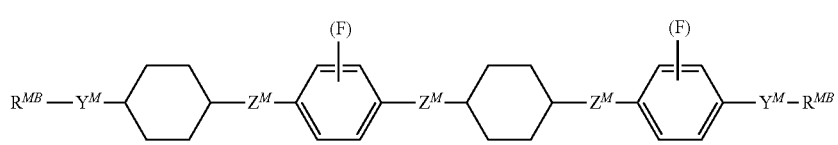
(M2-23)
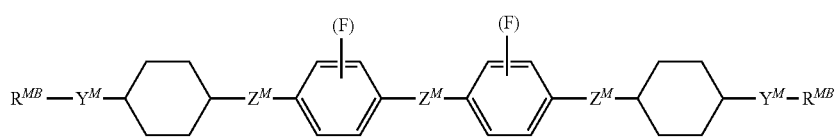

(M2-24)
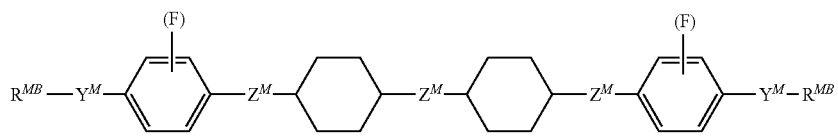

(M2-25)
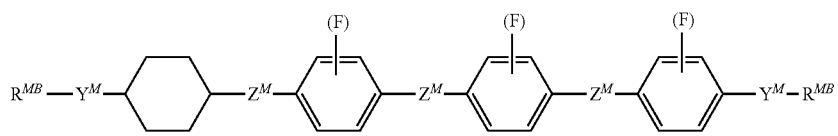

(M2-26)
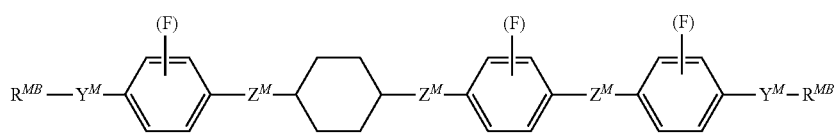

(M2-27)
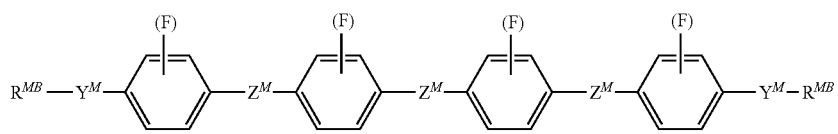

As the raw material monomer of the polymer, a polymerizable compound other than the monomer having no mesogen moiety, and monomers (M1) and (M2) both having the mesogen moiety as described above can be used when necessary.

For the purpose of optimizing the optical isotropy of the polymer/liquid crystal composite material according to the invention, a monomer having a mesogen moiety and three or more polymerizable functional groups can also be used. As the monomer having the mesogen moiety and three or more polymerizable functional groups, a publicly known compound can be preferably used. Specific examples include compounds (M4-1) to (M4-3), and further specific examples include compounds described in JP 2000-327632 A, JP 2004-182949 A and JP 2004-59772 A. However, in formulas (M4-1) to (M4-3), $R^{MB}$, $Z^M$, $Y^M$ and (F) are defined in a manner identical with the definitions described above.

(M4-1)

(M4-2)

(M4-3)

4-2-2 Monomer Having Polymerizable Functional Group and No Mesogen Moiety

Specific examples of a monomer having a polymerizable functional group and no mesogen moiety include a straight-chain or branched-chain acrylate having 1 to 30 carbons, or a straight-chain or branched-chain diacrylate having 1 to 30 carbons, and specific examples of a monomer having three or more polymerizable functional groups include glycerol propoxylate (1 PO/OH) triacrylate, pentaerythritol propoxylate triacrylate, pentaerythritol triacrylate, trimethylolpropane ethoxylate triacrylate, trimethylolpropane propoxylate triacrylate, trimethylolpropane triacrylate, di(trimethylolpropane) tetraacrylate, pentaerythritol tetraacrylate, di(pentaerythritol) pentaacrylate, di(pentaerythritol) hexacrylate and trimethylolpropane triacrylate, but are not limited thereto.

4-2-3 Polymerization Initiator

The polymerization reaction in manufacture of the polymer that constitutes the composite material of the invention is not limited and, for example, photoradical polymerization, thermal radical polymerization, photocationic polymerization or the like is performed.

Specific examples of a photoradical polymerization initiator that can be used in the photoradical polymerization include DAROCUR 1173 and 4265 (trade names for both, BASF Japan, Ltd.), and IRGACURE 184, 369, 500, 651, 784, 819, 907, 1300, 1700, 1800, 1850 and 2959 (trade names for all, BASF Japan, Ltd.).

Specific examples of a preferred initiator for the thermal radical polymerization by heat, in which the initiator can be used in the thermal radical polymerization, include benzoyl peroxide, diisopropyl peroxydicarbonate, t-butyl peroxy-2-ethylhexanoate, t-butyl peroxypivalate, t-butyl peroxydiisobutyrate, lauroyl peroxide, 2,2'-azobis(methyl isobutyrate) (MAIB), di-t-butyl peroxide (DTBPO), azobisisobutyronitrile (AIBN) and azobis(cyclohexancarbonitrile) (ACN).

Specific examples of a photocationic polymerization initiator that can be used in the photocationic polymerization include diaryliodonium salt (hereinafter, referred to as "DAS") and a triarylsulfonium salt (hereinafter, referred to as "TAS").

Specific examples of DAS include diphenyliodonium tetrafluoroborate, diphenyliodonium hexafluorophosphonate, diphenyliodonium hexafluoroarsenate, diphenyliodonium trifluoromethane sulfonate, diphenyliodonium trifluoroacetate, diphenyliodonium-p-toluene sulfonate, diphenyliodonium tetra(pentafluorophenyl)borate, 4-methoxyphenylphenyliodonium tetrafluoroborate, 4-methoxyphenylphenyliodonium hexafluorophosphonate, 4-methoxyphenylphenyliodonium hexafluoroarsenate, 4-methoxyphenylphenyliodonium trifluoromethane sulfonate, 4-methoxyphenylphenyliodonium trifluoroacetate and 4-methoxyphenylphenyliodonium-p-toluene sulfonate.

An improvement in sensitivity of DAS can also be achieved by adding a photosensitizer such as thioxanthone, phenothiazine, chlorothioxanthone, xanthone, anthracene, diphenylanthracene and rubrene to DAS.

Specific examples of TAS include triphenylsulfonium tetrafluoroborate, triphenylsulfonium hexafluorophosphonate, triphenylsulfonium hexafluoroarsenate, triphenylsulfonium trifluoromethanesulfonate, triphenylsulfonium trifluoroacetate, triphenylsulfonium p-toluenesulfonate, triphenylsulfonium tetra(pentafluorophenyl) borate, 4-methoxyphenyldiphenylsulfonium tetrafluoroborate, 4-methoxyphenyldiphenylsulfonium hexafluorophosphonate, 4-methoxyphenyldiphenylsulfonium hexafluoroarsenate, 4-methoxyphenyldiphenylsulfonium trifluoromethane sulfonate, 4-methoxyphenyldiphenylsulfonium trifluoroacetate and 4-methoxyphenyldiphenylsulfonium-p-toluene sulfonate.

Specific examples of the trade names of the photocationic polymerization initiator include Cyracure UVI-6990, Cyracure UVI-6974, and Cyracure UVI-6992 (trade names, respectively, UCC Corporation), ADEKA Optomer SP-150, SP-152, SP-170, SP-172 (trade names, respectively, ADEKA Corporation), Rhodorsil Photoinitiator 2074 (trade name, Rhodia Japan, Ltd.), IRGACURE 250 (trade name, BASF Japan, Ltd.) and UV-9380C (trade name, GE Toshiba Silicones, Co., Ltd.).

4-2-4 Curing Agent or the Like

In manufacture of the polymer that constitutes the composite material according to the invention, in addition to the monomer or the like and the polymerization initiator, one kind or two or more kinds of other preferred components, for example, the curing agent, the catalyst and the stabilizer, may be added thereto.

As the curing agent, a publicly known latent curing agent that has been ordinarily used as a curing agent for an epoxy resin can be used. Specific examples of the latent curing agent for the epoxy resin include an amine curing agent, a novolak resin curing agent, an imidazole curing agent and an acid anhydride curing agent. Specific examples of the amine curing agent include aliphatic polyamine such as diethylenetriamine, triethylenetetramine, tetraethylenepentamine, m-xylenediamine, trimethylhexamethylenediamine, 2-methylpentamethylenediamine and diethylaminopropylamine, alicyclic polyamine such as isophoronediamine, 1,3-bisaminomethylcyclohexane, bis(4-aminocyclohexyl)methane, norbornenediamine, 1,2-diaminocyclohexane and Laromin, and aromatic polyamine such as diaminodiphenylmethane, diaminodiphenylethane and m-phenylenediamine.

Specific examples of the novolak resin curing agent include a phenol novolak resin and a bisphenol novolak resin. Specific examples of the imidazole curing agent include 2-methylimidazole, 2-ethylhexilimidazole, 2-phenylimidazole and 1-cyanoethyl-2-phenylimidazolium trimellitate.

Specific examples of the acid anhydride curing agent include tetrahydrophthalic anhydride, hexahydrophthalic anhydride, methyltetrahydrophthalic anhydride, methylhexahydrophthalic anhydride, methylcyclohexene tetracarboxylic dianhydride, phthalic anhydride, trimellitic anhydride, pyromellitic anhydride and benzophenonetetracarboxylic dianhydride.

A curing accelerator for promoting a curing reaction of the polymerizable compound having a glycidyl group, an epoxy group or an oxetanyl group and the curing agent may be further used. Specific examples of the curing accelerator include tertiary amines such as benzyldimethylamine, tris(dimethylaminomethyl)phenol and dimethylcyclohexylamine, imidazoles such as 1-cyanoethyl-2-ethyl-4-methylimidazole and 2-ethyl-4-methylimidazole, an organic phosphorus compound such as triphenylphosphine, quaternary phosphonium salts such as tetraphenylphosphonium bromide, diazabicycloalkenes such as 1,8-diazabicyclo[5.4.0]undecene-7 and an organic acid salt thereof, quaternary ammonium salts such as tetraethylammonium bromide and tetrabutylammonium bromide, and a boron compounds such as boron trifluoride and triphenyl borate. The curing accelerators can be used alone or by mixing a plurality thereof.

In order to prevent undesired polymerization during storage, for example, addition of the stabilizer is preferred. As the stabilizer, all the compounds known to those skilled in the art can be used. Typified examples of the stabilizer include 4-ethoxyphenol, hydroquinone and butylated hydroxytoluene (BHT).

4-3 Composition of Polymer/Liquid Crystal Composite Material

A content of the liquid crystal composition in the polymer/liquid crystal composite material according to the invention is preferably as high as possible, if the content is within the range in which the composite material can develop the optically isotropic liquid crystal phase. The reason is that a value of the electric birefringence of the composite material of the invention becomes larger as the content of the liquid crystal composition is higher.

In the polymer/liquid crystal composite material of the invention, the content of the liquid crystal composition is preferably 60 to 99% by weight, further preferably 60% by weight to 98% by weight, and particularly preferably 80% by weight to 97% by weight, based on the composite material. Moreover, in the polymer/liquid crystal composite material of the invention, a content of the polymer is preferably 1% by weight to 40% by weight, further preferably 2% by weight to 40% by weight, and particularly preferably 3% by weight to 20% by weight, based on the composite material.

5 Optical Device

The optical device of the invention refers to the optical device including the liquid crystal composition or the polymer/liquid crystal composite material (hereinafter, the liquid crystal composition and the polymer/liquid crystal composite material according to the invention may be occasionally referred to generically as the liquid crystal medium) to be driven in the optically isotropic liquid crystal phase.

The liquid crystal medium is optically isotropic when no electric field is applied, but when the electric field is applied, the optical anisotropy is caused in the liquid crystal medium, and optical modulation by the electric field can be made.

Specific examples of structure of a liquid crystal display device include, as shown in FIG. 1, the structure in which electrode 1 extended from a left side and electrode 2 extended from a right side are alternately arranged in electrodes of a comb-shaped electrode substrate. When a potential difference exists between electrode 1 and electrode 2, on the comb-shaped electrode substrate as shown in FIG. 1, if attention is paid to one electrode, a state in which electric fields in two directions, namely an upward direction and a downward direction on the diagram, can be provided.

The liquid crystal composition of the invention can be used in the optical device. The liquid crystal composition of the invention exhibits a low drive voltage and a short response time. Therefore, the optical device in the preferred aspect of the invention can be driven at the low voltage, and can achieve a high-speed response.

6 Compound

The liquid crystal compounds of the invention are compounds represented by formulas (1-1-1) and (1-5-1).

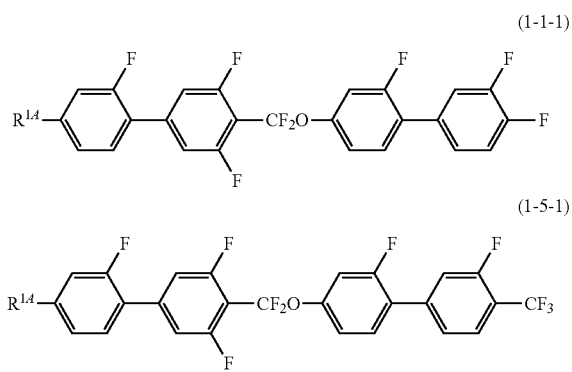

(In the formulas, $R^{14}$ is alkyl having 1 to 12 carbons.).

The compound represented by formula (1-1-1) has the high clearing point, a large value of the dielectric anisotropy and a large value of the refractive index anisotropy, and the compound represented by formula (1-2) has the comparatively high clearing point, the large value of the dielectric anisotropy, and the comparatively good compatibility at the low temperature. The composition in which the compounds are used has the low drive voltage and the wide temperature range of the liquid crystal phase, and a small temperature dependence of the drive voltage in the temperature range centering on the operating temperature, and thus is useful as the component of the liquid crystal composition.

EXAMPLES

The invention will be described below in greater detail by way of Examples. However, the invention is not limited by the Examples. Unless otherwise noted, "%" means "% by weight."

Moreover, a compound obtained was identified using a nuclear magnetic resonance spectrum obtained according to $^1$H-NMR analysis, a gas chromatogram obtained according to gas chromatography (GC) analysis or the like. Analytical methods were as described below.

1) Analytical Method 1-1) $^1$H-NMR Analysis

As a measuring apparatus, DRX-500 (trade name, made by Bruker BioSpin Corporation) was used. A sample prepared in Example or the like was dissolved in a deuterated solvent such as $CDCl_3$ in which the sample was soluble, and measurement was carried out under conditions of room temperature, 24 times of accumulation and 500 MHz. In addition, in explaining a nuclear magnetic resonance spectrum obtained, s, d, t, q and m stand for a singlet, a doublet, a triplet, a quartet and a multiplet, respectively. Tetramethylsilane (TMS) was used as a reference material for a zero point of chemical shifts (δ values).

1-2) GC Analysis

As a measuring apparatus, GC-14B Gas Chromatograph made by Shimadzu Corporation was used. As a column, capillary column CBP1-M25-025 (length 25 m, bore 0.22 mm, film thickness 0.25 μm; dimethylpolysiloxane as a stationary liquid phase; non-polar) made by Shimadzu Corporation was used. Helium was used as a carrier gas, and a flow rate was adjusted at 1 milliliter per minute. Temperature in a sample vaporizing chamber was set at 300° C. and temperature of a detector (FID) unit was set at 300° C.

The sample was dissolved in toluene and prepared to be a 1% solution, and 1 microliter of the solution obtained was injected into the sample vaporizing chamber.

As a recorder, C-R6A Chromatopac made by Shimadzu Corporation or the equivalent thereof was used. In the gas chromatograms obtained, a retention time of a peak corresponding to each of component compounds and values of peak areas are shown.

In addition, as a solvent for diluting the sample, chloroform or hexane, for example, may be used. Moreover, as the column, capillary column DB-1 (length 30 m, bore 0.32 mm, film thickness 0.25 μm) made by Agilent Technologies Inc., HP-1 (length 30 m, bore 0.32 mm, film thickness 0.25 μm) made by Agilent Technologies Inc., Rtx-1 (length 30 m, bore 0.32 mm, film thickness 0.25 μm) made by Restek Corporation, BP-1 (length 30 m, bore 0.32 mm, film thickness 0.25 μm) made by SGE International Pty. Ltd., or the like may be used.

A ratio of the peak areas in the gas chromatogram corresponds to a ratio of the component compounds. In general, weight percent of each of the component compounds in an analytical sample is not completely identical with a percentage of each of the peak areas in the analytical sample. However, when the column described above was used in the invention, the weight percent of each of the component compounds in the analytical sample substantially corresponds to the percentage of each of the peak areas in the analytical sample because a correction coefficient is essentially 1 (one). The reason is that no significant difference exists in the correction coefficients of the components in the liquid crystal compound. An internal standard method by the gas chromatograms is used in order to determine a composition ratio of the liquid crystal compounds in a liquid crystal composition more accurately by the gas chromatograms. Each liquid crystal compound component (test-component) weighed accurately in a fixed amount and a standard liquid crystal compound (standard reference material) are simultaneously measured according to gas chromatography, and the relative intensity of the ratio of the peak areas obtained between the test-component and the standard reference material is calculated in advance. When corrected based on the relative intensity of the peak area of each component relative to the standard reference material, the composition ratio of the liquid crystal compounds in the liquid crystal composition can be determined more accurately according to the gas chromatographic analysis.

1-3) Sample for Measuring Physical Properties of Liquid Crystal Compound or the Like A sample for determining values of physical property of a liquid crystal compound includes two types of cases: a case where the compound itself is used as the sample, and a case where the compound is mixed with a base liquid crystal to be used as the sample.

In the latter case where the sample prepared by mixing the compound with the base liquid crystal is used, measurement is carried out according to the method described below. First, the sample is prepared by mixing 15% of the liquid crystal compound obtained and 85% of the base liquid crystal. Then, according to an extrapolation method based on the calculation equation as shown below, extrapolated values are calculated from measured values of the sample obtained. The extrapolated values are described as the values of physical property of the compound.

[Extrapolated value]=(100×[measured value of a sample]−[% of base liquid crystal]×[measured value of the base liquid crystal])/[% of the compound].

When a smectic phase or crystals precipitate at 25° C. even at the ratio of the liquid crystal compound to the base liquid crystal (15%:85%), a ratio of the liquid crystal compound to the base liquid crystal was changed in the order of (10%:90%), (5%:95%) and (1%:99%), the physical properties of the sample were measured at a composition in which no smectic phase or no crystals precipitated at 25° C., and the extrapolated values were determined according to the equation, and described as the physical properties of the compound.

As the base liquid crystal used for measurements, a variety of kinds exist. For example, a composition of base liquid crystal (A) (%) is as described below.
(Base Liquid Crystal A)

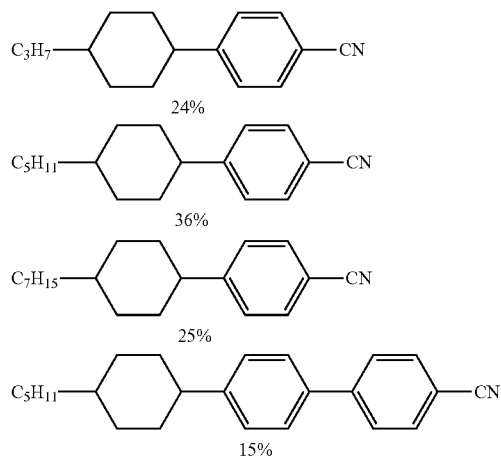

1-4) Methods for Determining Values of Physical Properties of Liquid Crystal Compound or the Like Determination of values of physical properties was performed according to the methods described below. Most of the measuring methods are described in EIAJ ED-2521A of the Standard of Electronic Industries Association of Japan, or modified thereon. Moreover, no TFT was attached to a TN device used for measurements.

Among measured values, in the case where the liquid crystal compound itself was used as the sample, the values obtained were described as experimental data. In the case where the mixture of the liquid crystal compound with the base liquid crystal was used as the sample, the values obtained according to the extrapolation method were described as experimental data.

1-4-1) Phase Structure and Phase Transition Temperature (° C.):

Measurement was carried out according to method (1) and method (2) described below.

(1) A compound was placed on a hot plate of a melting point apparatus (FP-52 Hot Stage made by Mettler Toledo International Inc.) equipped with a polarizing microscope, and a state of a phase and a change thereof were observed by the polarizing microscope while the compound was heated at a rate of 3° C. per minute, and a kind of liquid crystal phase was specified.

(2) A sample was heated and then cooled at a rate of 3° C. per minute using a differential scanning calorimeter, DSC-7 System or Diamond DSC System, made by PerkinElmer, Inc. A starting point of an endothermic peak or an exothermic peak caused by a change of phase of the sample was determined by extrapolation, and thus a phase transition temperature was determined.

Hereinafter, the crystals were expressed as K, and when the crystals were further distinguishable, each of the crystals was expressed as $K_1$ or $K_2$. The smectic phase was expressed as Sm, the nematic phase as N and the chiral nematic phase as N*. A liquid (isotropic) was expressed as I. When smectic B phase or smectic A phase were distinguishable in the smectic phase, each of the phases was expressed as SmB or SmA, respectively. BP represents a blue phase or an optically isotropic liquid crystal phase. A state of coexistence of two phases may sometimes be represented in the forms of (N*+I) or (N*+BP). Specifically, (N*+I) represents a phase in which a non-liquid crystal isotropic phase and a chiral nematic phase coexist, and (N*+BP) represents a phase in which a BP phase or an optically isotropic liquid crystal phase and a chiral nematic phase coexist. Un represents an unidentified phase that is not optically isotropic. As an expression of the phase transition temperature, for example, "K 50.0 N 100.0 I" means 50.0° C. in a phase transition temperature from the crystals to the nematic phase (KN), and 100.00° C. in a phase transition temperature from the nematic phase to the liquid (NI). A same rule also applied to any other expression.

1-5) Maximum Temperature of Nematic Phase ($T_{NI}$; ° C.):

A sample (a mixture of the liquid crystal compound and the base liquid crystal) was placed on a hot plate of a melting point apparatus (FP52 Hot Stage made by Mettler Toledo International Inc.) equipped with a polarizing microscope, and was observed by the polarizing microscope while the sample was heated at a rate of 1° C. per minute. Temperature when part of the sample changed from the nematic phase to the isotropic liquid was described as a maximum temperature. Hereinafter, the maximum temperature of the nematic phase may simply be occasionally abbreviated as "maximum temperature."

1-6) Compatibility at Low Temperature:

Samples in which the liquid crystal compound and the base liquid crystal were mixed for the liquid crystal compound to be 20%, 15%, 10%, 5%, 3% and 1% were prepared, and placed in glass vials. After the glass vials were kept in freezers at −10° C. or −20° C. for a predetermined period of time, whether or not the crystals or the smectic phase precipitated was observed.

1-7) Viscosity (Bulk Viscosity; η; Measured at 20° C.; mPa·s)

The mixture of the liquid crystal compound and the base liquid crystal was measured by a cone-plate (E type) viscometer.

1-8) Refractive Index Anisotropy (Δn)

Measurement was carried out by an Abbe refractometer with a polarizing plate mounted on an ocular by using light at a wavelength of 589 nanometers at a temperature of 25°

C. A surface of a main prism was rubbed in one direction, and then a sample (a mixture of the liquid crystal compound and the base liquid crystal) was added dropwise onto the main prism. A refractive index (n∥) was measured when the direction of polarized light was parallel to the direction of rubbing. A refractive index (n⊥) was measured when the direction of polarized light was perpendicular to the direction of rubbing. Values of refractive index anisotropy (Δn) were calculated from an equation: Δn=n∥−n⊥.

1-9) Dielectric Anisotropy (Δε; Measured at 25° C.)

A sample (a mixture of the liquid crystal compound and the base liquid crystal) was put in a liquid crystal cell in which a distance (gap) between two glass substrates was about 9 μm and a twist angle was 80 degrees. A voltage of 20 V was applied to the cell, and a dielectric constant (ε∥) in the major axis direction of liquid crystal molecules was measured. A voltage of 0.5 V was applied to the cell, and a dielectric constant (ε⊥) in the minor axis direction of the liquid crystal molecules was measured. A value of dielectric anisotropy was calculated from an equation: Δε=ε∥−ε⊥.

1-10) Pitch (P; 25° C. Measurement; Nm)

Pitch length was measured using selective reflection (Handbook of Liquid Crystals (Ekisho Binran in Japanese), page 196, (issued in 2000, Maruzen Co., Ltd.)). A relational formula: <n>p/λ=1 holds for selective reflection wavelength λ. Here, <n> represents an average refractive index and is given by the following formula: $<n>=\{(n_{\parallel}^2+n_{\perp}^2)/2\}^{1/2}$. The selective reflection wavelength was measured by a microspectrophotometer (JEOL Ltd., trade name MSV-350). The pitch was determined by dividing obtained reflection wavelength by an average refractive index. Because the pitch of a cholesteric liquid crystal having a reflection wavelength in a region of wavelength longer than the wavelength of visible light is proportional to a reciprocal of a concentration of an optically active compound in a region in which the concentration of the optically active compound is low, the pitch was determined by measuring several pitch lengths of a liquid crystal having a selective reflection wavelength in a visible light region, and applying a linear extrapolation method. "Optically active compound" corresponds to a chiral agent of the invention.

In the invention, values of characteristic of the liquid crystal composition can be determined according to the method described below. Most of the methods are applied as described in EIAJ ED-2521A of the Standard of Electronic Industries Association of Japan, or as modified thereon. No TFT was attached to a TN device used for measurement.

1-11) Maximum Temperature of Nematic Phase (NI; ° C.):

A sample was placed on a hot plate in a melting point apparatus equipped with a polarizing microscope and was heated at a rate of 1° C. per minute. Temperature when part of the sample began to change from a nematic phase to an isotropic liquid was measured. A maximum temperature of the nematic phase may be occasionally abbreviated as "maximum temperature."

1-12) Minimum Temperature of Nematic Phase ($T_c$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_c$ was expressed as $T_c$≤−20° C. A minimum temperature of the nematic phase may be occasionally abbreviated as "minimum temperature."

1-13) Transition Temperature of Optically Isotropic Liquid Crystal Phase

A sample was placed on a hot plate of a melting point measuring apparatus equipped with a polarizing microscope. A sample was first heated, in a crossed nicol state, to temperature at which the sample becomes a non-liquid crystal isotropic phase, and then the temperature was decreased at a rate of 1° C./min to develop a liquid crystal phase that is completely a chiral nematic phase or an optically isotropic liquid crystal phase. Temperature at which phase transition was caused in a temperature-decreasing process was measured, subsequently the temperature was increased at a rate of 1° C./min, and temperature at which the phase transition was caused in a temperature-increasing process was measured. In the invention, unless otherwise noted, the temperature at which the phase transition was caused in the temperature-increasing process was taken as a phase transition temperature. When discrimination of the phase transition temperature was difficult in a dark field under crossed nicols in an optically isotropic liquid crystal phase, the phase transition temperature was measured by shifting the polarizing plate by 1 to 10° from the crossed nicol state.

1-14) Viscosity (Rotational Viscosity; γ1; Measured at 25° C.; mPa·s)

(1) Sample having positive dielectric anisotropy: Measurement was carried out according to the method described in M. Imai et al., Molecular Crystals and Liquid Crystals, Vol. 259, p. 37 (1995). A sample was put in a TN device in which a twist angle was 0° and a distance (cell gap) between two glass substrates was 5 μm. A voltage was applied stepwise to the device in the range of 16 V to 19.5 V at an increment of 0.5 V. After a period of 0.2 second with no voltage, a voltage was applied repeatedly under conditions of only one rectangular wave (rectangular pulse; 0.2 second) and no voltage (2 seconds). A peak current and a peak time of a transient current generated by the application were measured. A value of rotational viscosity was obtained from the measured values and a calculation equation (8) on page 40 of the paper presented by M. Imai et al. A value of dielectric anisotropy required for the calculation was determined by the method of measuring the dielectric anisotropy described below in the device used in measurement of the rotational viscosity.

(2) Sample having negative dielectric anisotropy: Measurement was carried out according to the method described in M. Imai et al., Molecular Crystals and Liquid Crystals, Vol. 259, p. 37 (1995). A sample was put in a VA device in which a distance (cell gap) between two glass substrates was 20 μm. A voltage was applied stepwise to the device in the range of 30 V to 50 V at an increment of 1 V. After a period of 0.2 second with no voltage, a voltage was applied repeatedly under the conditions of only one rectangular wave (rectangular pulse; 0.2 second) and no voltage (2 seconds). A peak current and a peak time of a transient current generated by the application were measured. A value of rotational viscosity was obtained from the measured values and a calculation equation (8) on page 40 of the paper presented by M. Imai et al. As the dielectric anisotropy value required for the calculation, a value measured in the dielectric anisotropy measuring method described below was used.

1-15) Refractive Index Anisotropy (Δn; Measured at 25° C.):

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of refractive index anisotropy was calculated from an equation: Δn=n∥−n⊥. When a sample was a composition, the refractive index anisotropy was measured by the method described above.

1-16) Dielectric Anisotropy (Δε; Measured at 25° C.):

(1) Composition having positive dielectric anisotropy: A sample was put in a liquid crystal cell in which a distance (gap) between two glass substrates was about 9 μm and a twist angle was 80 degrees. A voltage of 20 V was applied to the cell, and a dielectric constant (ε∥) in the major axis direction of liquid crystal molecules was measured. A voltage of 0.5 V was applied to the cell, and a dielectric constant (ε⊥) in the minor axis direction of the liquid crystal molecules was measured. A value of dielectric anisotropy was calculated from an equation: Δε=ε∥−ε⊥.

(2) Composition having negative dielectric anisotropy: A sample was put in a liquid crystal cell processed into homeotropic alignment, and a dielectric constant (ε∥) was measured by applying a voltage of 0.5 V. The sample was put in a liquid crystal cell processed into homogeneous alignment, and a dielectric constant (ε⊥) was measured by applying a voltage of 0.5 V. A value of dielectric anisotropy was calculated from an equation: Δε=ε∥−ε⊥.

1-17) Threshold Voltage (Vth; Measured at 25° C.; V)

1) Composition having positive dielectric anisotropy: A sample was put in a normally white mode liquid crystal display device in which a distance (cell gap) between two glass substrates was (0.5/An) μm and a twist angle was 80 degrees. Here, Δn represents a value of refractive index anisotropy measured by the method described above. Rectangular waves having a frequency of 32 Hz were applied to the device. A voltage of the rectangular wave was increased and a value of voltage when the transmittance of the light transmitted through the device became 90% was measured.

2) Composition having negative dielectric anisotropy: A sample was put in a normally black mode liquid crystal device in which a distance (cell gap) between two glass substrates was approximately 9 μm, and which was processed into homeotropic alignment. Rectangular waves having a frequency of 32 Hz were applied to the device. A voltage of the rectangular wave was increased and a value of voltage when the transmittance of the light transmitted through the device became 10% was measured.

1-18) Voltage Holding Ratio (VHR; Measured at 25° C.; %)

A TN device used for measurement had a polyimide-alignment film, and a distance (cell gap) between two glass substrates was 6 μm. A sample was put in the device, and then the device was sealed with an ultraviolet-polymerizable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was obtained. Area B is an area without decay. A voltage holding ratio is a percentage of area A to area B.

1-19) Helical Pitch (Measured at 20° C.; μm)

A Cano wedge cell method was applied to measurement of a helical pitch. The sample was injected into a Cano wedge cell, and a distance (a; unit μm) between disclination lines observed from a cell was measured. Helical pitch (P) was calculated from formula: P=2·a·tan θ. Here, θ is an angle between two glass plates in the wedge cell.

Alternatively, pitch length was measured using selective reflection (Handbook of Liquid Crystals (Ekisho Binran in Japanese), page 196, issued in 2000, Maruzen Co., Ltd.). A relational formula: <n>p/λ=1 holds in selective reflection wavelength λ. Here, <n> represents an average refractive index and is given by the following formula: <n>={(n∥²+n⊥²)/2)}^{1/2}. The selective reflection wavelength was measured by a microspectrophotometer (JEOL Ltd., trade name MSV-350). The pitch was obtained by dividing obtained reflection wavelength by an average refractive index.

Because the pitch of the cholesteric liquid crystal having the reflection wavelength in the region of the wavelength longer than the wavelength of visible light is proportional to the reciprocal of the concentration of the chiral agent in the region in which the concentration of the chiral agent is low, the pitch was obtained by measuring several pitch lengths of the liquid crystal having the selective reflection wavelength in the visible light region, and applying the linear extrapolation method.

A proportion (percentage) of the component or the liquid crystal compound is expressed in terms of weight percent (% by weight) based on the total weight of the liquid crystal compound. A composition is prepared by measuring the weight of components, such as liquid crystal compounds, and then mixing the components. Therefore, the weight percent of the component is easily calculated.

Example 1

Compound (1-1-1S) of the present application was prepared according to the scheme described below:

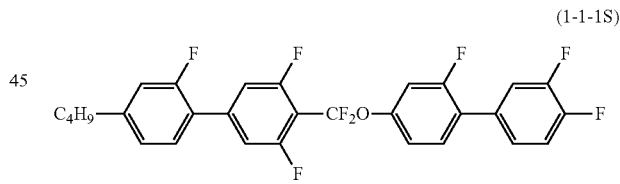
(1-1-1S)

(In compound (1-1-1), R¹ is butyl.).

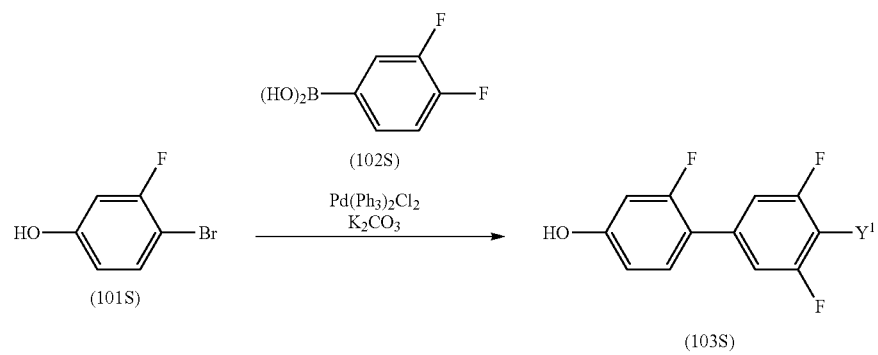

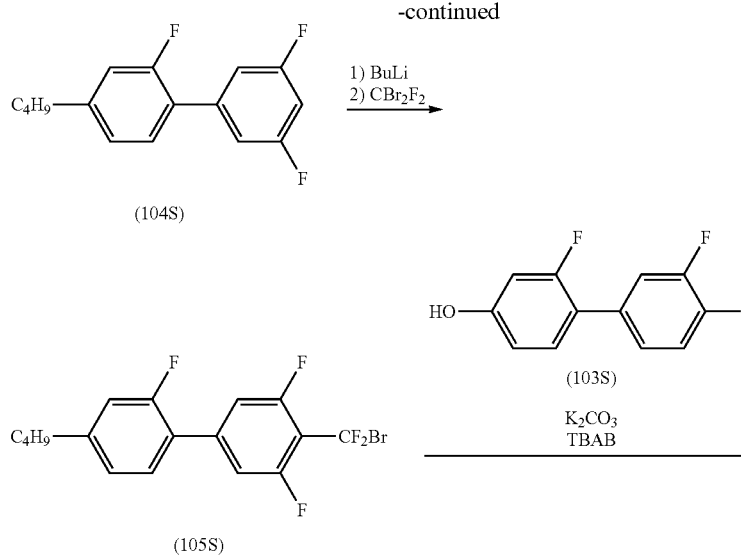

(First Step) Synthesis of Compound (103S)

Under a nitrogen flow, a mixed solution of compound (101S) (25.0 g, 131 mmol), compound (102S) (20.9 g, 132 mmol), potassium carbonate (39.8 g, 288 mmol), dichlorobis(triphenyl phosphine)palladium(II) (0.919 g, 1.31 mol), triphenylphosphine (0.685 g, 2.62 mmol), tetrabutylammonium bromide (4.22 g, 13.1 mmol), toluene (75 mL) and isopropanol (75 mL) was heated and stirred at 80° C. for 5 hours. The resulting reaction liquid was poured into water, diethyl ether (500 mL) was added thereto, and washed three times with water, and then an organic phase was concentrated under reduced pressure. Heptane was added to a residue and the resulting solution was stirred, cooled to 0° C. and subjected to filtration, and a crystal obtained through filtration was taken out to obtain compound (103S) (14.8 g, 56.6 mmol).

(Second Step) Synthesis of Compound (105S)

Under a nitrogen flow, an n-butyl lithium/n-hexane solution (1.60 mol/L) (62.1 mL, 99.3 mmol) was slowly added dropwise to a THF (150 mL) solution of compound (104S) (25.0 g, 94.6 mmol) at −40° C., and the resulting solution was stirred at a temperature as was for 1 hour. Subsequently, a dibromodifluoroethane (23.8 g, 114 mmol)/THF (50 mL) solution was slowly added dropwise in the system at a temperature as was, and the resulting solution was stirred for 1 hour, while temperature was gradually returned to room temperature. The resulting reaction liquid was poured into water and the resulting solution was subjected to extraction with toluene (300 mL), and washed three times with water, and then an organic phase was concentrated under reduced pressure. The residue was purified by silica gel column chromatography (solvent: toluene/n-heptane=1/5) to obtain compound (105S) (37.0 g (73%), 68.4 mmol). The mixture was used as was for the next reaction.

(Third Step) Synthesis of Compound (1-1-15)

Under a nitrogen flow, a DMF (50 mL) mixed solution of compound (103S) (4.10 g, 18.3 mmol) obtained in the first step, compound (105S) (9.85 g (73%), 18.3 mmol) obtained in the preceding step, potassium carbonate (5.31 g, 38.4 mmol) and tetrabutylammonium bromide (1.77 g, 5.50 mmol) was heated and stirred at 70° C. for 2 hours. The resulting reaction liquid was poured into water, and the resulting solution was subjected to extraction with toluene (100 mL), and washed three times with water and twice with sodium bicarbonate water, and then an organic phase was concentrated under reduced pressure. The residue was purified by silica gel column chromatography (solvent: toluene/ n-heptane 1/5) and further by recrystallization (solvent: ethanol/n-heptane 1/1) and filtration to obtain compound (1-1-1S) (6.04 g, 11.2 mmol) being a final object. A phase transition temperature (° C.) of the compound was C 49.9 N 93.6 I.

$^1$H-NMR (CDCl$_3$): δ (ppm) 0.64-0.97 (3H, t), 1.35-1.42 (2H, m), 1.60-1.66 (2H, m), 2.64-2.68 (2H, t), 7.01-7.03 (1H, dd), 7.06-7.08 (1H, dd), 7.15-7.26 (6H, m), 7.31-7.40 (3H, m).

$^{19}$F-NMR (CDCl$_3$): δ (ppm) −61.18--−61.58 (2F, t), −111.31--−111.45 (2F, dt), −115.17--−115.22 (1F, dd), −118.32--−118.36 (1F, dd), −137.97--−138.07 (1F, m), −139.25--−139.35 (1F, m).

Next, as base liquid crystal A, the four compounds described above were mixed to prepare base liquid crystal A having a nematic phase. Physical properties of base liquid crystal A were as described below.

Maximum temperature ($T_{NI}$)=71.7° C.; dielectric anisotropy (Δε)=11.0; refractive index anisotropy (Δn)=0.137.

Liquid crystal composition AS1 composed of base liquid crystal A (85%) and compound (1-1-1S) (15%) obtained was prepared. Values of physical properties of liquid crystal composition AS1 obtained were determined and extrapolated values of physical properties of compound (1-1-1S) were calculated by extrapolating the measured values. The values were as described below.

Maximum temperature ($T_{NI}$)=63.7° C.; dielectric anisotropy (Δε)=34.1; refractive index anisotropy (Δn)=0.170.

Compound (1-1-1S) was found to be a compound having a large dielectric anisotropy (Δε), a large refractive index anisotropy and a good compatibility from the results described above.

Example 2

Compound (1-5-1S) of the present application was prepared according to the scheme described below.

(1-5-1S)

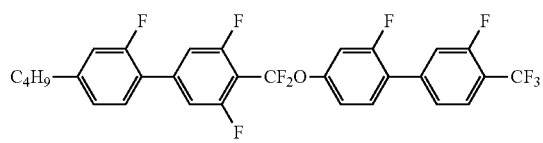

(In compound (1-5-1), $R^1$ is butyl.).

(112S)

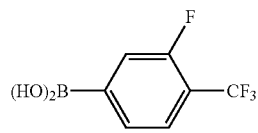

Compound (1-5-1S) (3.50 g, 5.97 mmol) was obtained according to a scheme completely similar to the scheme in Example 1 except that compound (101S) and (104S) in Example 1 were used as starting materials, and compound (112S) was used in place of compound (102S). A phase transition temperature (° C.) of the compound was C 43.6 N 83.2 I.

$^1$H-NMR (CDCl$_3$): δ (ppm) 0.938-0.968 (3H, t), 1.35-1.42 (2H, m), 1.60-1.67 (2H, m), 2.65-2.68 (2H, t), 7.01-7.03 (1H, dd), 7.06-7.08 (1H, dd), 7.18-7.23 (4H, m), 7.32-7.35 (3H, m), 7.39-7.46 (3H, m), 7.66-7.70 (1H, dd).

$^{19}$F-NMR (CDCl$_3$): δ (ppm) −61.51--−61.68 (2F, t), −61.77--−61.79 (3F, d), −111.31--−111.44 (2F, dt), −114.58--114.71 (2F, m), −118.31--−118.36 (1F, dd).

Example 3

Compound (1-9-1S) of the present application was prepared according to the scheme described below.

(1-9-1S)

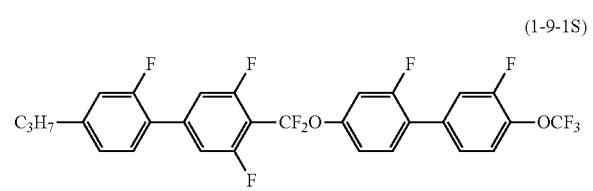

(In compound (1-9-1), $R^1$ is propyl.).

(122S)

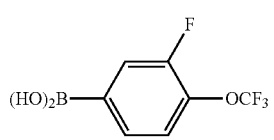

(124S)

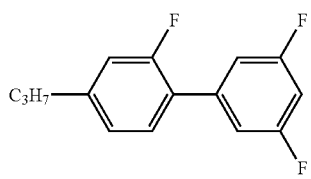

Compound (1-9-1S) (6.30 g, 10.7 mmol) was obtained according to a scheme completely similar to the scheme in Example 1 except that compound (101S) and (104S) in Example 1 were used as starting materials, compound (122S) was used in place of compound (102S), and compound (124S) was used in place of compound (104S). A phase transition temperature (° C.) of the compound was C 49.6 N 116.9 I.

$^1$H-NMR (CDCl$_3$): δ (ppm) 0.962-0.991 (3H, t), 1.66-1.71 (2H, m), 2.62-2.66 (2H, t), 7.01-7.03 (1H, dd), 7.06-7.08 (1H, dd), 7.17-7.23 (4H, m), 7.31-7.43 (5H, m).

$^{19}$F-NMR (CDCl$_3$): δ (ppm) −59.19--−59.20 (3F, d), −61.50--−61.61 (2F, t), −111.31--−111.44 (2F, dt), −114.92--114.96 (1F, dd), −118.34--−118.38 (1F, dd), −128.89--−128.96 (1F, m).

Example 4

Preparation of Nematic Liquid Crystal Composition (NLC)

Nematic liquid crystal composition NLC-A containing compound (1-1-1S) prepared in Example 1 was prepared by mixing compounds shown below. Moreover, liquid crystal composition NLC-R was prepared as a reference of NLC-A. NLC-A is a composition in which part of NLC-R was replaced by compound (1).

TABLE 1

| | | (NLC-A) | (NLC-R) |
|---|---|---|---|
| C$_6$H$_{13}$—[structure]—CF$_2$O—[structure]—F | (3-3A) | 5.0 wt % | 5.0 wt % |
| C$_5$H$_{11}$—[structure]—CF$_2$O—[structure]—F | (3-3A) | 5.0 wt % | 5.0 wt % |

TABLE 1-continued
| | | (NLC-A) | (NLC-R) |
|---|---|---|---|
| 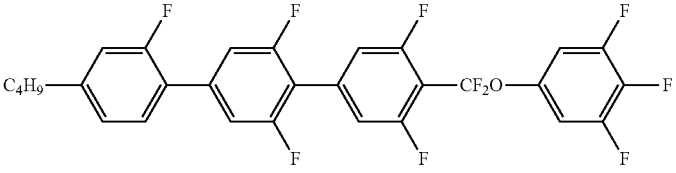 | (3-3A) | 5.0 wt % | 5.0 wt % |
| 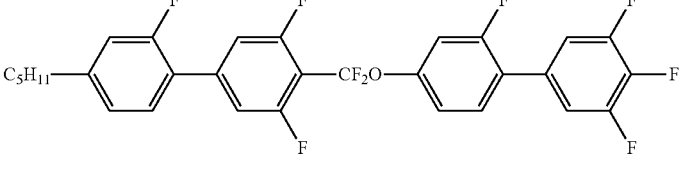 | (3-2C) | 7.5 wt % | 15.0 wt % |
| 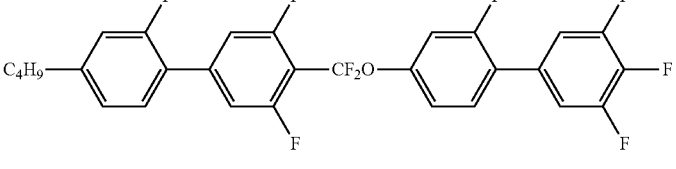 | (3-2C) | 7.5 wt % | 15.0 wt % |
| 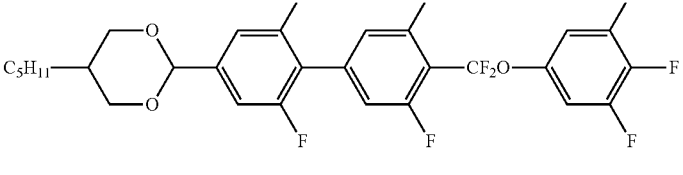 | (7-2-2F) | 15.5 wt % | 15.5 wt % |
| 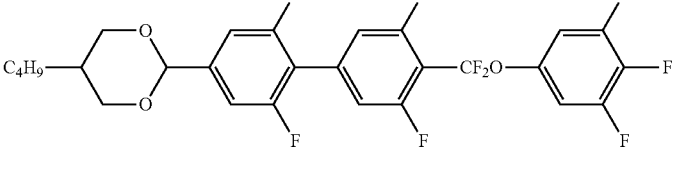 | (7-2-2F) | 15.5 wt % | 15.5 wt % |
| 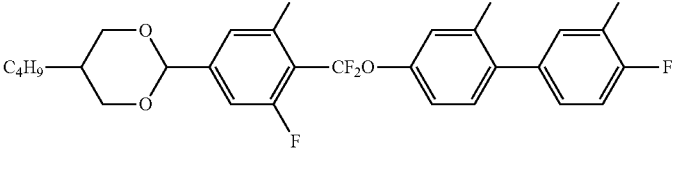 | (7-1-1) | 12.0 wt % | 12.0 wt % |
| 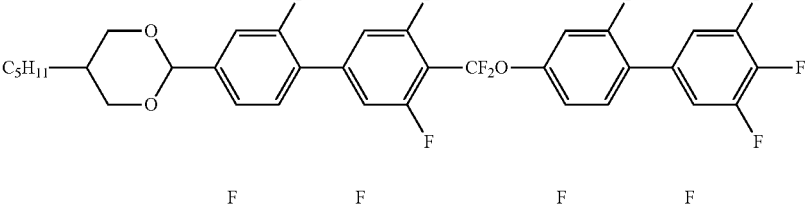 | (7-7) | 12.0 wt % | 12.0 wt % |
| 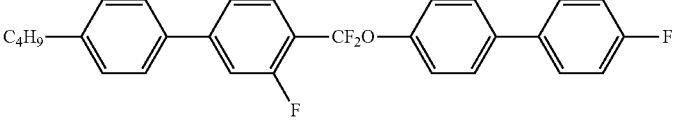 | (1-1-1S) | 15.0 wt % | |

A phase transition temperature (° C.) of NLC-A was N 110.6 to 111.8 I, and a phase transition temperature (° C.) of NLC-R was N 108.5 to 109.8 I.

Example 5

Preparation of Chiral Liquid Crystal Composition (CLC)

Chiral liquid crystal compositions CLC-A and CLC-R were prepared by mixing each of nematic liquid crystal compositions obtained in Example 4 and chiral agent (CD1) shown below. Compositions and phase transition temperatures of the chiral liquid crystal composition were as described below.

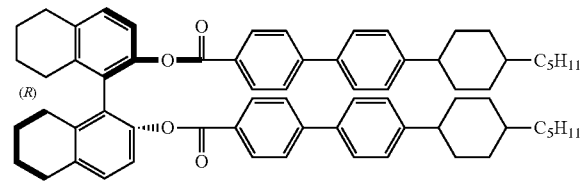
CD1

| CLC-A | |
|---|---|
| NLC-A | 94.8% by weight |
| CD-1 | 5.2% by weight |

Phase transition temperature (° C.): N* 101.3 to 101.6 BP 103.1 BP+I 104.5 I

| CLC-R | |
|---|---|
| NLC-R | 94.8% by weight |
| CD-1 | 5.2% by weight |

Phase transition temperature (° C.): N* 99.3 to 99.7 BP 101.4 BP+I 102.3 I

Example 6

Preparation of Liquid Crystal Composition (MLC) being Mixture with Polymerizable Monomer Liquid crystal compositions MLC-A and MLC-R were prepared by heating and mixing a mixture of each of chiral liquid crystal compositions (CLC) prepared in Example 5 and a polymerizable monomer in an isotropic phase. Formulations of the liquid crystal compositions are shown below.

In addition, LCA-12 is 1,4-di(4-(6-(acryloyloxy)dodecyloxy)benzoyloxy)-2-methylbenzene, DMPA is 2,2'-dimethoxyphenylacetophenone, and a photopolymerization initiator.

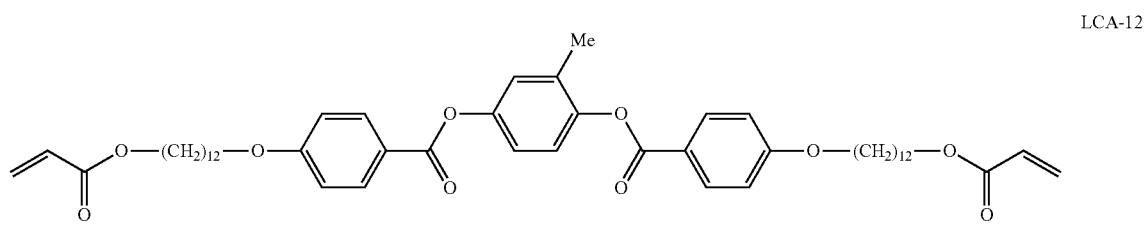
LCA-12

| MLC-A | |
|---|---|
| CLC-A | 88.4% by weight |
| n-hexadecyl acrylate | 6.2% by weight |
| LCA-12 | 5.0% by weight |
| DMPA | 0.4% by weight |

Phase transition temperature (° C.): N* 67.5 to 68.1 BP 72.5 BP+I 73.4 I

| MLC-R | |
|---|---|
| CLC-R | 88.4% by weight |
| n-hexadecyl acrylate | 6.2% by weight |
| CA-12 | 5.0% by weight |
| DMPA | 0.4% by weight |

Phase transition temperature (° C.): N* 66.8 to 67.4 I

Example 7

Cell with Polymer/Liquid Crystal Composite Material Interposed Therebetween

Liquid crystal composition (MLC-A) being a mixture of chiral liquid crystal composition (CLC-A) and a polymerizable monomer was interposed between a comb-shaped electrode substrate subjected to no alignment treatment and a facing glass substrate (not provided with an electrode), and the resulting assembly was heated to a blue phase.

In the above state, the assembly was irradiated with ultraviolet light (ultraviolet light intensity 23 mWcm$^{-2}$ (365 nm)) for 1 minute, in which a polymerization reaction was performed at 68.0° C. to prepare a cell in which polymer/liquid crystal composite material (PSBP-A) was interposed therebetween (cell thickness 7 to 9 µm). Even if the polymer/liquid crystal composite material (PSBP-A) obtained was cooled to room temperature, the material maintained an optically isotropic liquid crystal phase.

Comparative Example 1

Cell with Polymer/Liquid Crystal Composite Material Interposed Therebetween

Liquid crystal composition (MLC-R) being a mixture of chiral liquid crystal composition (CLC-R) and a polymerizable monomer was interposed between a comb-shaped electrode substrate subjected to no alignment treatment and a facing glass substrate (not provided with an electrode), and the resulting assembly was heated to a blue phase.

In the above state, the assembly was irradiated with ultraviolet light (ultraviolet light intensity 23 mWcm$^{-2}$ (365 nm)) for 1 minute, and a polymerization reaction was performed at 67.3° C. to prepare a cell in which polymer/liquid crystal composite material (PSBP-R) was interposed therebetween (cell thickness 7 to 9 μm). Even if the thus obtained polymer/liquid crystal composite material (PSBP-R) was cooled to room temperature, the material maintained an optically isotropic liquid crystal phase.

Example 8

Optical System Using Cell

Figure 2:
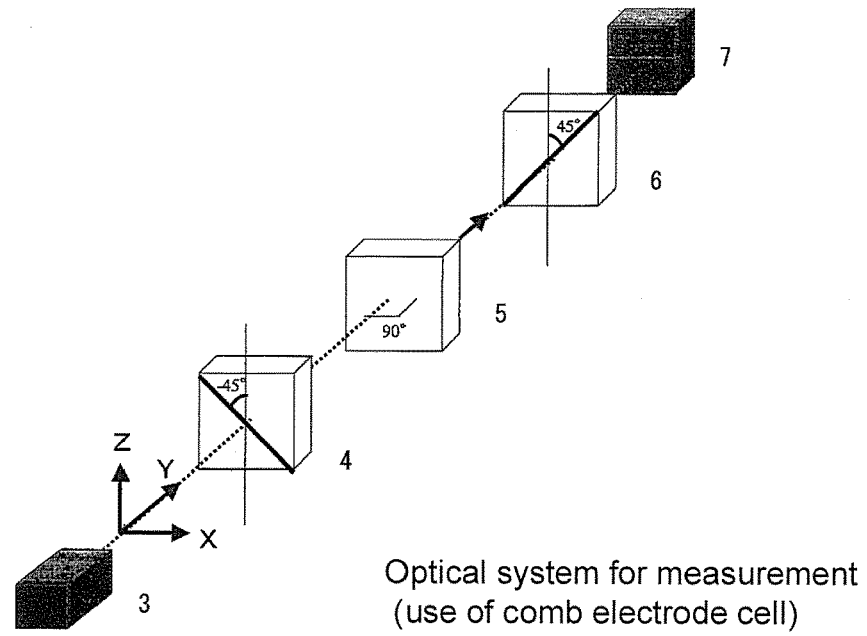
FIG. 2 shows an optical system used in Examples.

The combo-shaped electrode cells 5 in which the polymer/liquid crystal composite materials were interposed therebetween as obtained in Example 6 and Comparative Example 1 were set in an optical system shown in FIG. 2. Specifically, as a light source 3, a white light source of a polarization microscope (ECLIPSE LV100POL made by Nikon Corporation) was used, and the cell in which the polymer/liquid crystal composite material was interposed therebetween was set such that an angle of incidence to the cell was adjusted to be perpendicular to a cell plane, and a line direction of the comb-shaped electrode became 45 degrees relative to Polarizer 4 and Analyzer 6, respectively, and as a photodetector 7, an multimedia display tester (3298 made by Yokogawa) (MUYOKOGAWA) was used (FIG. 2).

A relationship was investigated between applied voltage and transmittance of the polymer/liquid crystal composite material at room temperature by using the optical system. Values of physical properties of the polymer/liquid crystal composite material (PSBP) interposed therebetween in the cell were as described below. In addition, data of response time is during saturated voltage application and during removal.

PSBP-A

Saturated voltage ($V_{MAX}$) was 72.4 (V), a contrast ratio was 1,107, response velocity ($V_{10-90}$) during voltage application was 1.14 (ms), and response velocity ($V_{90-10}$) during voltage removal was 0.82 (ms).

PSBP-R

Saturated voltage ($V_{MAX}$) was 67.5(V), a contrast ratio was 1,042, response velocity ($V_{10-90}$) during voltage application was 1.33 (ms), and response velocity ($V_{90-10}$) during voltage removal was 0.74 (ms).

Example 9

Comparison of Temperature Dependence of Saturated Voltage

Figure 3:
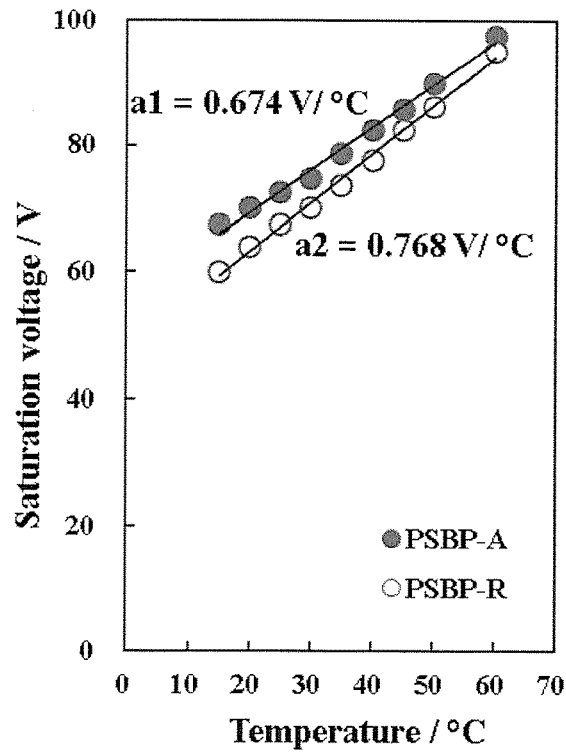
FIG. 3 shows temperature dependence of saturated voltage of a polymer/liquid crystal composite material used in Example 9.

According to the method presented in Example 7, a relationship was investigated between applied voltage and transmittance of the polymer/liquid crystal composite material in the temperature range of 15 to 60° C. to verify temperature dependence of saturated voltage. FIG. 3 shows a relationship between saturated voltage and temperature as measured using PSBP-A and PSBP-R. Here, a1 and a2 in the Figure each are a value obtained by dividing the saturated voltage in 15 to 60° C. by a temperature in the temperature range with regard to PSBP-A and PSBP-R, and as the value is smaller, the temperature dependence of saturated voltage is smaller.

From FIG. 3, while a2 of PSBP-R is 0.768, a1 of PSBP-R results in 0.674, which shows that the temperature dependence of saturated voltage in 15 to 60° C. was improved by about 10%. From the result, PSBP-A was found to have lower temperature dependence of drive voltage, while the drive voltage was somewhat larger, in comparison with PSBP-R. Compound (1) was found to be a compound effective in improving the temperature dependence of the drive voltage in the device.

Example 10

Preparation of Nematic Liquid Crystal Composition (NLC)

Nematic liquid crystal composition NLC-B containing compound (1-5-1S) prepared in Example 2 was prepared by mixing compounds shown below. Moreover, liquid crystal composition NLC-R2 was prepared as a reference of NLC-B. NLC-B is a composition in which part of compounds in NLC-R2 was replaced by compound (1).

TABLE 2

| | (NLC-B) | (NLC-R2) |
|---|---|---|
| 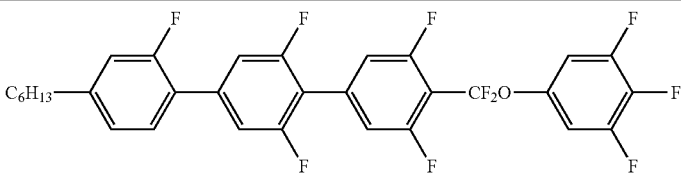 (3-3A) | 5.0 wt % | 5.0 wt % |

TABLE 2-continued
| Structure | | (NLC-B) | (NLC-R2) |
|---|---|---|---|
| 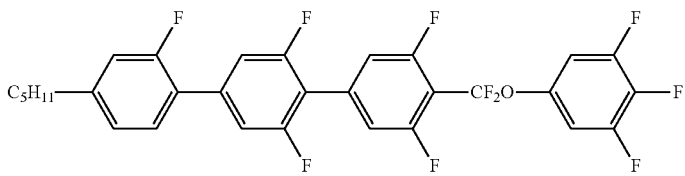 | (3-3A) | 5.0 wt % | 5.0 wt % |
| 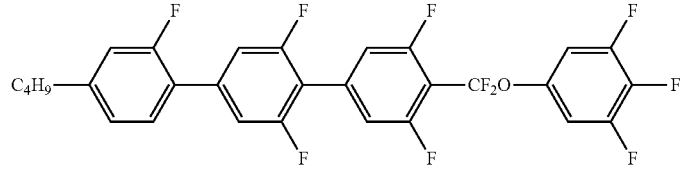 | (3-3A) | 5.0 wt % | 5.0 wt % |
| 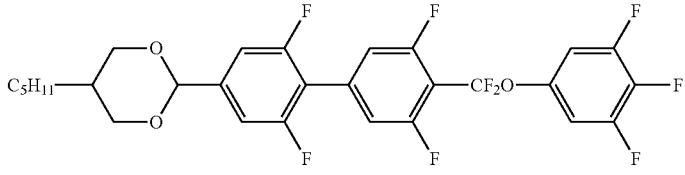 | (7-2-2F) | 15.5 wt % | 15.5 wt % |
| 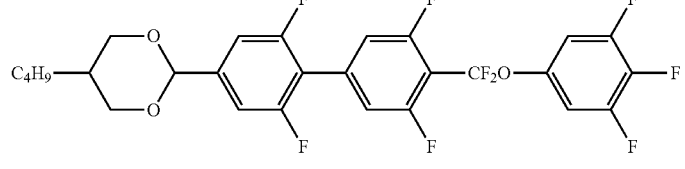 | (7-2-2F) | 15.5 wt % | 15.5 wt % |
| 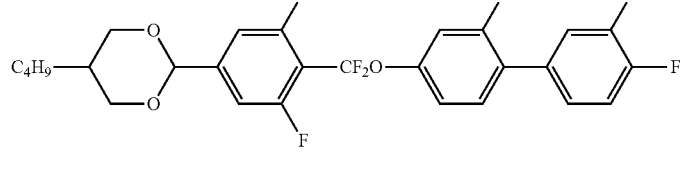 | (7-1-1) | 12.0 wt % | 12.0 wt % |
| 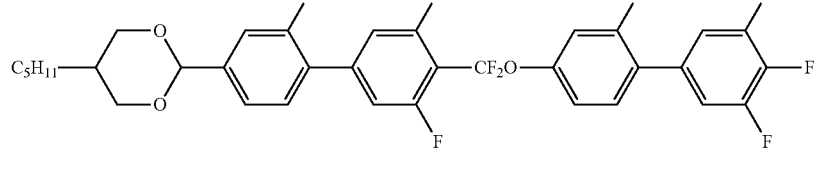 | (7-7) | 12.0 wt % | 12.0 wt % |
| 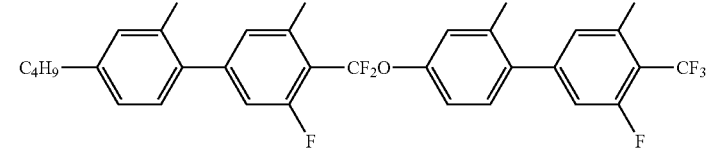 | (3-2C) | | 30.0 wt % |
| 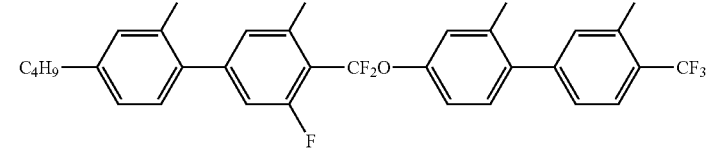 | (1-5-1S) | 30.0 wt % | |

A phase transition temperature of NLC-B (° C.) was N 109.0 to 110.3 I and a phase transition temperature of NLC-R2 (° C.) was N 111.1 to 113.0 I.

Example 11

Preparation of Chiral Liquid Crystal Composition (CLC)

Chiral liquid crystal compositions CLC-B and CLC-R2 were prepared by mixing each of nematic liquid crystal compositions obtained in Example 10, and chiral agent (CD1) shown in the section in Example 6. Compositions and phase transition temperatures of the chiral liquid crystal compositions were as described below.

| CLC-B | |
|---|---|
| NLC-B | 94.2% by weight |
| CD-1 | 5.8% by weight |

Phase transition temperature (° C.): N* 98.9 to 99.2 BP+I 109.0 I

| CLC-R2 | |
|---|---|
| NLC-R2 | 94.2% by weight |
| CD-1 | 5.8% by weight |

Phase transition temperature (° C.): N* 95.3 BP 103.3 BP+I 104.6 I

Example 12

Preparation of Liquid Crystal Composition (MLC) being Mixture with Polymerizable Monomer Liquid crystal compositions MLC-B and MLC-R2 were prepared by heating and mixing a mixture of each of chiral liquid crystal compositions (CLC) prepared in Example 11 and a polymerizable monomer in an isotropic phase. Formulations of the liquid crystal compositions are shown below. In addition, LCA-12 and DMPA represent the compounds identical with the compounds in Example 6.

| MLC-B | |
|---|---|
| CLC-B | 88.1% by weight |
| n-hexadecyl acrylate | 6.4% by weight |
| LCA-12 | 5.1% by weight |
| DMPA | 0.4% by weight |

Phase transition temperature (° C.): N* 64.0 to 64.6 BP 68.3 BP+I 68.8 I

| MLC-R2 | |
|---|---|
| CLC-R2 | 88.1% by weight |
| n-hexadecyl acrylate | 6.4% by weight |
| LCA-12 | 5.1% by weight |
| DMPA | 0.4% by weight |

Phase transition temperature (° C.): N* 63.4 to 63.8 BP 70.0 I

Example 13

Cell with Polymer/Liquid Crystal Composite Material Interposed Therebetween

Liquid crystal composition (MLC-B) being a mixture of chiral liquid crystal composition (CLC-B) and a polymerizable monomer was interposed between a comb-shaped electrode substrate subjected to no alignment treatment and a facing glass substrate (not provided with an electrode), and the resulting assembly was heated to a blue phase.

In the above state, the assembly was irradiated with ultraviolet light (ultraviolet light intensity 23 mWcm$^{-2}$ (365 nm)) for 1 minute, and a polymerization reaction was performed at 65.0° C. to prepare a cell in which polymer/liquid crystal composite material (PSBP-B) was interposed therebetween (cell thickness 7 to 9 μm). Even if the thus obtained polymer/liquid crystal composite material (PSBP-B) was cooled to room temperature, the material maintained an optically isotropic liquid crystal phase.

Comparative Example 2

Cell with Polymer/Liquid Crystal Composite Material Interposed Therebetween

Liquid crystal composition (MLC-R2) being a mixture of chiral liquid crystal composition (CLC-R2) and a polymerizable monomer was interposed between a comb-shaped electrode substrate subjected to no alignment treatment and a facing glass substrate (not provided with an electrode), and the resulting assembly was heated to a blue phase.

In the above state, the assembly was irradiated with ultraviolet light (ultraviolet light intensity 23 mWcm$^{-2}$ (365 nm)) for 1 minute, and a polymerization reaction was performed at 64.1° C. to prepare a cell in which polymer/liquid crystal composite material (PSBP-R2) was interposed therebetween (cell thickness 7 to 9 μm). Even if the thus obtained polymer/liquid crystal composite material (PSBP-R2) was cooled to room temperature, the material maintained an optically isotropic liquid crystal phase.

Example 14

Optical System Using Cell

The comb-shaped electrode cells in which the polymer/liquid crystal composite materials were interposed therebetween as obtained in Example 13 and Comparative Example 2 were set in an optical system shown in FIG. 2. Specifically, as a light source, a white light source of a polarization microscope (ECLIPSE LV100POL made by Nikon Corporation) was used, and the cell in which the polymer/liquid crystal composite material was interposed therebetween was set such that an angle of incidence to the cell was adjusted to be perpendicular to a cell plane, and a line direction of the comb-shaped electrode became 45 degrees relative to Polarizer 4 and Analyzer 6, respectively, and as a photodetector 7, an multimedia display tester (3298 made by Yokogawa) (MUYOKOGAWA) was used (FIG. 2).

A relationship was investigated between applied voltage and transmittance of the polymer/liquid crystal composite material at room temperature by using the optical system. Values of physical properties of the polymer/liquid crystal composite material (PSBP) interposed therebetween in the cell were as described below. In addition, data of response time is during saturated voltage application and during removal.

PSBP-B

Saturated voltage ($V_{MAX}$) was 86.3(V), a contrast ratio was 868, response velocity ($V_{10-90}$) during voltage application was 0.900 (ms), and response velocity ($V_{90-10}$) during voltage removal was 0.80 (ms).

PSBP-R2

Saturated voltage ($V_{MAX}$) was 78.9 (V), a contrast ratio was 1,046, response velocity ($V_{10-90}$) during voltage application was 1.10 (ms), and response velocity ($V_{90-10}$) during voltage removal was 0.600 (ms).

Example 15

Comparison of Temperature Dependence of Saturated Voltage

Figure 4:
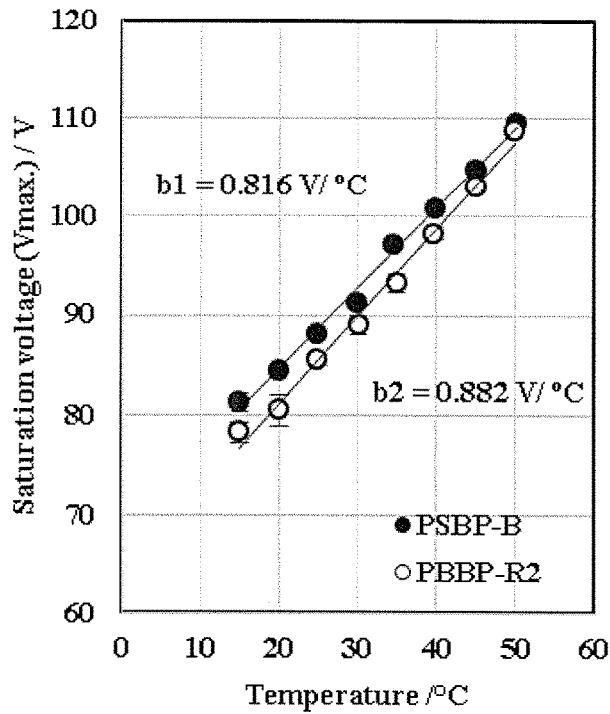
FIG. 4 shows temperature dependence of saturated voltage of a polymer/liquid crystal composite material used in Example 15.

According to the method presented in Example 13, a relationship was investigated between applied voltage and transmittance of the polymer/liquid crystal composite material in the temperature range of 15 to 50° C. to verify temperature dependence of saturated voltage. FIG. 4 shows a relationship between saturated voltage and temperature as measured using PSBP-B and PSBP-R2. Here, b1 and b2 in the Figure each are a value obtained by dividing the saturated voltage of PSBP-B and PSBP-R2 in 15 to 50° C. a temperature in by the temperature range, and as the value is smaller, the temperature dependence of saturated voltage is smaller.

From FIG. 4, while b2 of PSBP-R2 is 0.882, b1 of PSBP-B is 0.816, which shows that the temperature dependence of saturated voltage in 15 to 60° C. was improved by about 8%. From the result, PSBP-B was found to have lower temperature dependence of drive voltage, while the drive voltage was somewhat larger, in comparison with PSBP-R2. Compound (1) was found to be a compound effective in improving the temperature dependence of the drive voltage in the device.

Example 16

Preparation of Nematic Liquid Crystal Composition (NLC)

Nematic liquid crystal composition NLC-C containing compound (1-9-1S) prepared in Example 3 was prepared by mixing compounds shown below. Liquid crystal composition NLC-R3 was prepared as a reference of NLC-C. NLC-C is a composition in which part of compounds in NLC-R3 was replaced by compound (1).

TABLE 3

| Structure | | (NLC-C) | (NLC-R3) |
|---|---|---|---|
| $C_5H_{11}$—[2F-phenyl]—[2F-phenyl]—[2F-phenyl]—$CF_2O$—[2F-phenyl]—F | (3-3A) | 2.3 wt % | 2.3 wt % |
| $C_4H_9$—[2F-phenyl]—[2F-phenyl]—[2F-phenyl]—$CF_2O$—[2F-phenyl]—F | (3-3A) | 2.3 wt % | 2.3 wt % |
| $C_5H_{11}$—[dioxane]—[2F-phenyl]—[2F-phenyl]—$CF_2O$—[2F-phenyl]—F | (7-2-2F) | 9.0 wt % | 9.0 wt % |
| $C_4H_9$—[dioxane]—[2F-phenyl]—[2F-phenyl]—$CF_2O$—[2F-phenyl]—F | (7-2-2F) | 9.0 wt % | 9.0 wt % |
| $C_3H_7$—[dioxane]—[2F-phenyl]—[2F-phenyl]—$CF_2O$—[2F-phenyl]—F | (7-2-2F) | 8.4 wt % | 8.4 wt % |

TABLE 3-continued

| Structure | Code | (NLC-C) | (NLC-R3) |
|---|---|---|---|
| C5H11-dioxane-C6H2F2-CF2O-C6H3F-C6H2F2-F | (7-1-2) | 15.0 wt % | 15.0 wt % |
| C4H9-dioxane-C6H2F2-CF2O-C6H3F-C6H2F2-F | (7-1-2) | 15.0 wt % | 15.0 wt % |
| C3H7-dioxane-C6H2F2-CF2O-C6H3F-C6H2F2-F | (7-1-2) | 15.0 wt % | 15.0 wt % |
| C3H7-C6H3F-C6H2F2-CF2O-C6H3F-C6H2F2-OCF3 | (3-2C) | | 24.0 wt % |
| C3H7-C6H3F-C6H2F2-CF2O-C6H3F-C6H3F-OCF3 | (1-9-1S) | 24.0 wt % | |

A phase transition temperature (° C.) of NLC-C was N 95.6 to 96.1 I, and a phase transition temperature (° C.) of NLC-R3 was N 92.3 to 92.6 I.

Example 17

Preparation of Chiral Liquid Crystal Composition (CLC)

Chiral liquid crystal compositions CLC-C and CLC-R3 were prepared by mixing each of nematic liquid crystal compositions obtained in Example 16, and chiral agent (CD1) shown in the section in Example 6. Compositions and phase transition temperatures of the chiral liquid crystal compositions were as described below.

| CLC-C | |
|---|---|
| NLC-C | 94.2% by weight |
| CD-1 | 5.8% by weight |

Phase transition temperature (° C.): N* 86.3 to 86.7 BP+I 94.4 I

| CLC-R3 | |
|---|---|
| NLC-R3 | 94.2% by weight |
| CD-1 | 5.8% by weight |

Phase transition temperature (° C.): N* 82.5 to 82.8 BP+I 92.3 I

Example 18

Preparation of Liquid Crystal Composition (MLC) being Mixture with Polymerizable Monomer Liquid crystal compositions MLC-C and MLC-R3 were prepared by heating and mixing a mixture of each of chiral liquid crystal compositions (CLC) prepared in Example 17 and a polymerizable monomer in an isotropic phase. Formulations of the liquid crystal compositions are shown below. In addition, LCA-12 and DMPA represent the compounds identical with the compounds in Example 6.

| MLC-C | |
|---|---|
| CLC-C | 88.1% by weight |
| n-hexadecyl acrylate | 6.4% by weight |
| LCA-12 | 5.1% by weight |
| DMPA | 0.4% by weight |

Phase transition temperature (° C.): N* 55.0 to 55.3 BP 61.4 BP+I 61.9 I

| MLC-R3 | |
|---|---|
| CLC-R3 | 88.1% by weight |
| n-hexadecyl acrylate | 6.4% by weight |
| LCA-12 | 5.1% by weight |
| DMPA | 0.4% by weight |

Phase transition temperature (° C.): N* 52.0 to 52.4 BP 60.0 BP+I 60.6 I

Example 19

Cell with Polymer/Liquid Crystal Composite Material Interposed Therebetween

Liquid crystal composition (MLC-C) being a mixture of chiral liquid crystal composition (CLC-C) and a polymerizable monomer was interposed between a comb-shaped electrode substrate subjected to no alignment treatment and a facing glass substrate (not provided with an electrode), and the resulting assembly was heated to a blue phase.

In the above state, the assembly was irradiated with ultraviolet light (ultraviolet light intensity 23 mWcm$^{-2}$ (365 nm)) for 1 minute, and a polymerization reaction was performed at 55.5° C. to prepare a cell in which polymer/liquid crystal composite material (PSBP-C) was interposed therebetween (cell thickness 7 to 9 μm). Even if the thus obtained polymer/liquid crystal composite material (PSBP-C) was cooled to room temperature, the material maintained an optically isotropic liquid crystal phase.

Comparative Example 3

Cell with Polymer/Liquid Crystal Composite Material Interposed Therebetween

Liquid crystal composition (MLC-R3) being a mixture of chiral liquid crystal composition (CLC-R3) and a polymerizable monomer was interposed between a comb-shaped electrode substrate subjected to no alignment treatment and a facing glass substrate (not provided with an electrode), and the resulting assembly was heated to a blue phase.

In the above state, the assembly was irradiated with ultraviolet light (ultraviolet light intensity 23 mWcm$^{-2}$ (365 nm)) for 1 minute, and a polymerization reaction was performed at 53.7° C. to prepare a cell in which polymer/liquid crystal composite material (PSBP-R3) was interposed therebetween (cell thickness 7 to 9 μm). Even if the thus obtained polymer/liquid crystal composite material (PSBP-R3) was cooled to room temperature, the material maintained an optically isotropic liquid crystal phase.

Example 20

Optical System Using Cell

The comb-shaped electrode cells 5 in which the polymer/liquid crystal composite materials were interposed therebetween as obtained in Example 19 and Comparative Example 3 were set in an optical system shown in FIG. 2. Specifically, as a light source 3, a white light source of a polarization microscope (ECLIPSE LV100POL made by Nikon Corporation) was used, and the cell in which the polymer/liquid crystal composite material was interposed therebetween was set such that an angle of incidence to the cell was adjusted to be perpendicular to a cell plane, and a line direction of the comb-shaped electrode became 45 degrees relative to Polarizer 4 and Analyzer 6, respectively, and as a photodetector 7, an multimedia display tester (3298 made by Yokogawa) (MUYOKOGAWA) was used (FIG. 2).

A relationship was investigated between applied voltage and transmittance of the polymer/liquid crystal composite material at room temperature by using the optical system. Values of physical properties of the polymer/liquid crystal composite material (PSBP) interposed therebetween in the cell were as described below. In addition, data of response time is during saturated voltage application and during removal.

PSBP-C

Saturated voltage ($V_{MAX}$) was 97.8(V), a contrast ratio was 1,284, response velocity ($V_{10-90}$) during voltage application was 0.90 (ms), and response velocity ($V_{90-10}$) during voltage removal was 0.80 (ms).

PSBP-R3

Saturated voltage ($V_{MAX}$) was 84.0 (V), a contrast ratio was 1,221, response velocity ($V_{10-90}$) during voltage application was 1.10 (ms), and response velocity ($V_{90-10}$) during voltage removal was 0.60 (ms).

Example 21

Comparison of Temperature Dependence of Saturated Voltage

Figure 5:
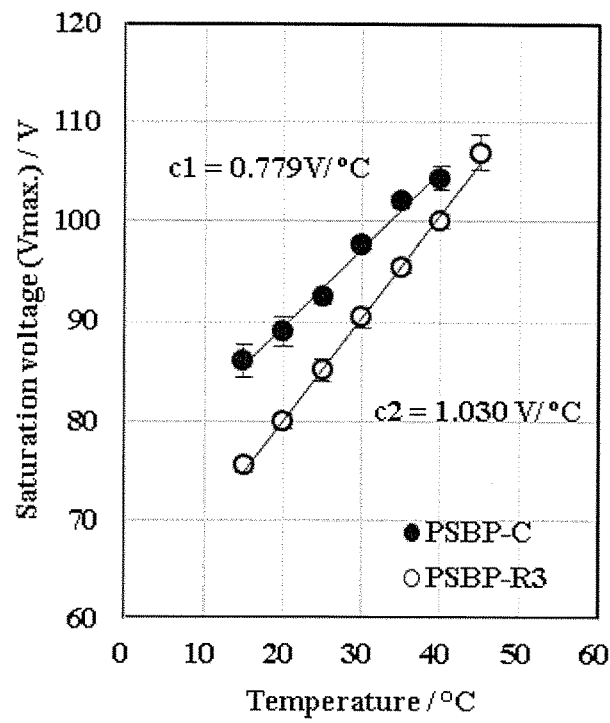
FIG. 5 shows temperature dependence of saturated voltage of a polymer/liquid crystal composite material used in Example 21.

According to the method presented in Example 19, a relationship was investigated between applied voltage and transmittance of the polymer/liquid crystal composite material in the temperature range of 15 to 45° C. to verify temperature dependence of saturated voltage. FIG. 5 shows a relationship between saturated voltage and temperature as measured using PSBP-C and PSBP-R3. Here, c1 and c2 in the Figure each are a value obtained by dividing the saturated voltage of PSBP-C and PSBP-R3 in 15 to 45° C. by a temperature in the temperature range, and as the value is smaller, the temperature dependence of saturated voltage is smaller.

From FIG. 5, while c2 of PSBP-R3 is 1.03, c1 of PSBP-C is 0.779, which shows that the temperature dependence of saturated voltage in 15 to 45° C. was improved by about 20%. From the result, PSBP-C was found to have lower temperature dependence of drive voltage, while the drive voltage was somewhat larger, in comparison with PSBP-R3. Compound (1) was found to be a compound effective in improving temperature dependence of the drive voltage in the device.

Example 22

Preparation of Nematic Liquid Crystal Composition (NLC)

Nematic liquid crystal composition NLC-D containing compound (1-1-1S) prepared in Example 1 was prepared by mixing compounds shown below. Liquid crystal composition NLC-R4 was prepared as a reference of NLC-D. NLC-D is a composition in which part of compounds in NLC-R4 was replaced by compound (1).

TABLE 4
| | | |
|---|---|---|
| 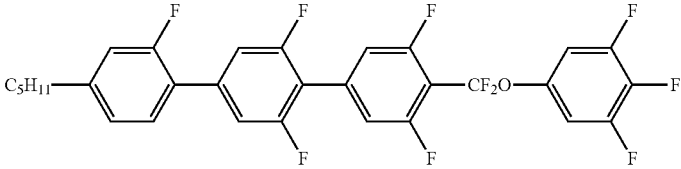 | (3-3A) 2.3 wt % | 2.3 wt % |
| 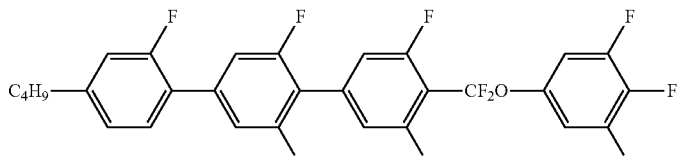 | (3-3A) 2.3 wt % | 2.3 wt % |
| 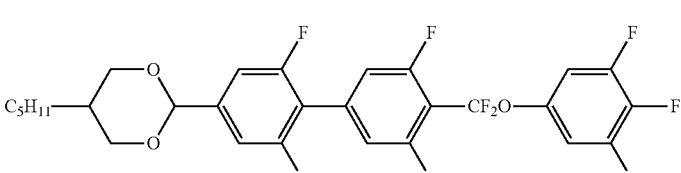 | (7-2-2F) 9.0 wt % | 9.0 wt % |
| 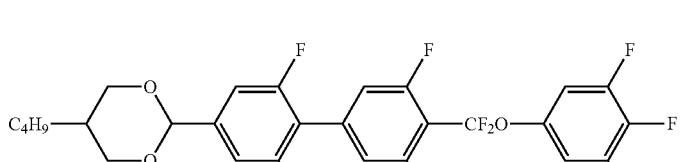 | (7-2-2F) 9.0 wt % | 9.0 wt % |
| 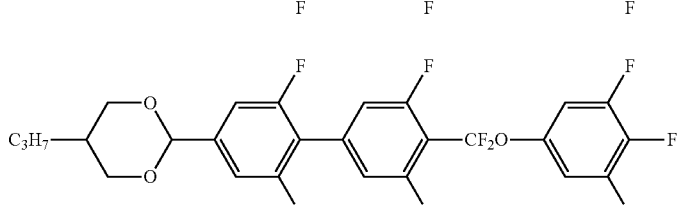 | (7-2-2F) 8.4 wt % | 8.4 wt % |
| 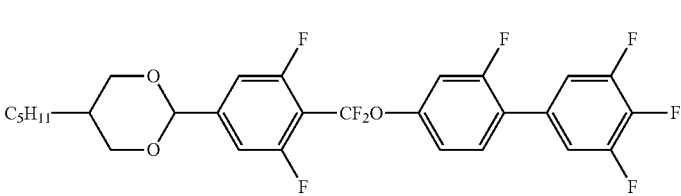 | (7-1-2) 15.0 wt % | 15.0 wt % |
| 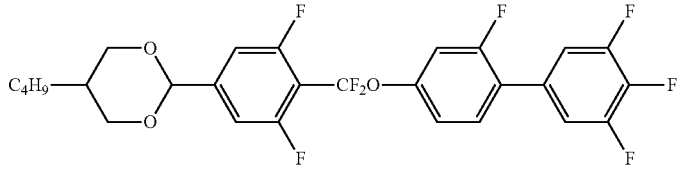 | (7-1-2) 15.0 wt % | 15.0 wt % |
| 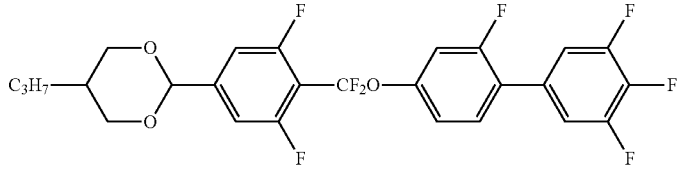 | (7-1-2) 15.0 wt % | 15.0 wt % |

TABLE 4-continued

| | | |
|---|---|---|
| (structure) | (3-2C) | (NLC-D) (NLC-R4) 24.0 wt % |
| (structure) | (1-1-1S) | 24.0 wt % |

A phase transition temperature (° C.) of NLC-D was N 86.2 to 86.4 I, and a phase transition temperature (° C.) of NLC-R4 was N 92.5 to 92.8 I.

Example 23

Preparation of Chiral Liquid Crystal Composition (CLC)

Chiral liquid crystal compositions CLC-D and CLC-R4 were prepared by mixing each of the nematic liquid crystal compositions obtained in Example 22, and chiral agent (CD1) shown in the section in Example 6. Formulations and phase transition temperature of the chiral liquid crystal compositions were as described below.

| CLC-D | |
|---|---|
| NLC-D | 94.2% by weight |
| CD-1 | 5.8% by weight |

Phase transition temperature (° C.): N* 76.8 BP+I 80.6 I

| CLC-R4 | |
|---|---|
| NLC-R4 | 94.2% by weight |
| CD-1 | 5.8% by weight |

Phase transition temperature (° C.): N* 82.5 to 82.7 BP 85.6 BP+I 86.3 I

Example 24

Preparation of Liquid Crystal Composition (MLC) being Mixture with Polymerizable Monomer Liquid crystal compositions MLC-D and MLC-R4 were prepared by heating and mixing a mixture of each of chiral liquid crystal compositions (CLC) prepared in Example 23 and a polymerizable monomer in an isotropic phase. Formulations of the liquid crystal compositions are shown below. Here, M4-2-1 is 1,3,4-tri(4-(6-(acryloyloxy)dodecyloxy)benzoyloxy)benzene, and DMPA represents a compound identical with the compound in Example 5.

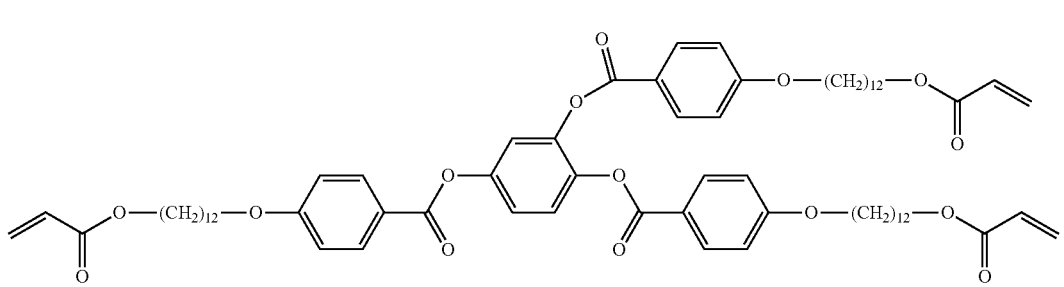

M4-2-1

| MLC-D | |
|---|---|
| CLC-D | 88.8% by weight |
| n-hexadecyl acrylate | 6.0% by weight |
| M4-2-1 | 4.8% by weight |
| DMPA | 0.4% by weight |

Phase transition temperature (° C.): N* 51.9 to 52.3 BP 53.6 BP+I 54.1 I

| MLC-R4 | |
|---|---|
| CLC-R4 | 88.1% by weight |
| n-hexadecyl acrylate | 6.0% by weight |
| M4-2-1 | 4.8% by weight |
| DMPA | 0.4% by weight |

Phase transition temperature (° C.): N* 45.8 BP 48.6 BP+I 49.0 I

Example 25

Cell with Polymer/Liquid Crystal Composite Material Interposed Therebetween

Liquid crystal composition (MLC-D) being a mixture of chiral liquid crystal composition (CLC-D) and a polymerizable monomer was interposed between a comb-shaped electrode substrate subjected to no alignment treatment and a facing glass substrate (not provided with an electrode), and the resulting assembly was heated to a blue phase.

In the above state, the assembly was irradiated with ultraviolet light (ultraviolet light intensity 23 mWcm$^{-2}$ (365 nm)) for 1 minute, and a polymerization reaction was performed at 52.3° C. to prepare a cell in which polymer/liquid crystal composite material (PSBP-D) was interposed therebetween (cell thickness 7 to 9 μm). Even if the thus obtained polymer/liquid crystal composite material (PSBP-D) was cooled to room temperature, the material maintained an optically isotropic liquid crystal phase.

Comparative Example 4

Cell with Polymer/Liquid Crystal Composite Material Interposed Therebetween

Liquid crystal composition (MLC-R4) being a mixture of chiral liquid crystal composition (CLC-R4) and a polymerizable monomer was interposed between a comb-shaped electrode substrate subjected to no alignment treatment and a facing glass substrate (not provided with an electrode), and the resulting assembly was heated to a blue phase.

In the above state, the assembly was irradiated with ultraviolet light (ultraviolet light intensity 23 mWcm$^{-2}$ (365 nm)) for 1 minute, and a polymerization reaction was performed at 46.1° C. to prepare a cell in which polymer/liquid crystal composite material (PSBP-R4) was interposed therebetween (cell thickness 7 to 9 μm). Even if the thus obtained polymer/liquid crystal composite material (PSBP-R4) was cooled to room temperature, the material maintained an optically isotropic liquid crystal phase.

Example 26

Optical System Using Cell

The comb-shaped electrode cells 5 in which the polymer/liquid crystal composite materials were interposed therebetween as obtained in Example 25 and Comparative Example 4 were set in an optical system shown in FIG. 2. Specifically, as a light source 3, a white light source of a polarization microscope (ECLIPSE LV100POL made by Nikon Corporation) was used, and the cell in which the polymer/liquid crystal composite material was interposed therebetween was set such that an angle of incidence to the cell was adjusted to be perpendicular to a cell plane, and a line direction of the comb-shaped electrode became 45 degrees relative to Polarizer 4 and Analyzer 6, respectively, and as a photodectector 7, an multimedia display tester (3298 made by Yokogawa) (MUYOKOGAWA) was used (FIG. 2).

A relationship was investigated between applied voltage and transmittance of the polymer/liquid crystal composite material at room temperature by using the optical system. Values of physical properties of the polymer/liquid crystal composite material (PSBP) interposed therebetween in the cell were as described below. In addition, data of response time is during saturated voltage application and during removal.

PSBP-D

Saturated voltage ($V_{MAX}$) was 99.4 (V), a contrast ratio was 1,989, response velocity ($V_{10-90}$) during voltage application was 0.80 (ms), and response velocity ($V_{90-10}$) during voltage removal was 0.40 (ms).

PSBP-R4

Saturated voltage ($V_{MAX}$) was 89.1 (V), a contrast ratio was 2392, response velocity ($V_{10-90}$) during voltage application was 0.70 (ms), and response velocity ($V_{90-10}$) during voltage removal was 0.40 (ms).

Example 27

Comparison of Temperature Dependence of Saturated Voltage

Figure 6:
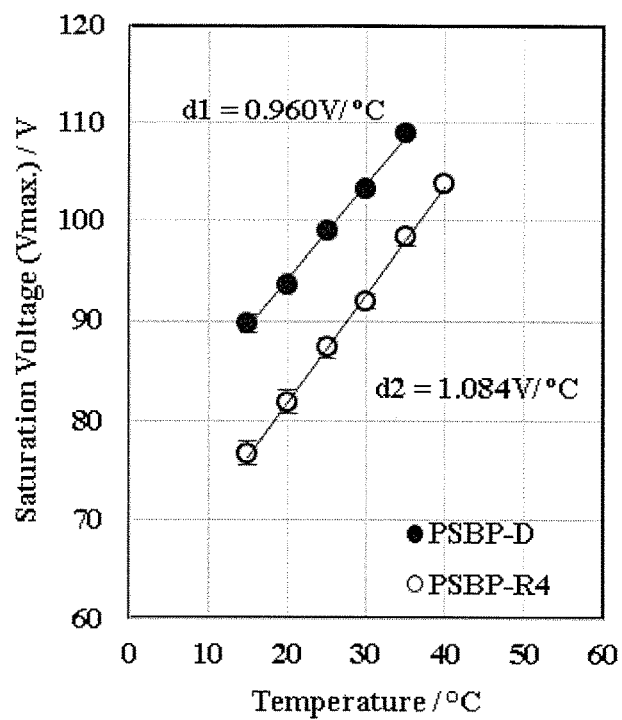
FIG. 6 shows temperature dependence of saturated voltage of a polymer/liquid crystal composite material used in Example 27.

According to the method presented in Example 25, a relationship was investigated between applied voltage and transmittance of the polymer/liquid crystal composite material in the temperature range of 15 to 45° C. to verify temperature dependence between saturated voltage. FIG. 6 shows a relationship between saturated voltage and temperature as measured using PSBP-D and PSBP-R4. Here, d1 and d2 in the Figure each are a value obtained by dividing the saturated voltage of PSBP-D and PSBP-R4 in 15 to 40° C. by a temperature the temperature range, and as the value is smaller, the temperature dependence of saturated voltage is smaller.

From FIG. 6, while d2 of PSBP-R4 is 1.08, d1 of PSBP-D is 0.960, which shows that the temperature dependence of saturated voltage in 15 to 40° C. was improved by about 10%. From the result, PSBP-D was found to have lower temperature dependence of drive voltage, while the drive voltage was somewhat larger, in comparison with PSBP-R4. Compound (1) was found to be a compound effective in improving the temperature dependence of the drive voltage in the device.

INDUSTRIAL APPLICABILITY

Specific examples of methods of utilizing the invention include an optical device in a display device in which a polymer/liquid crystal composite is used, or the like.

What is claimed is:

1. A liquid crystal composition that contains an achiral component T containing at least one compound (1) represented by formula (1) as a first component and a chiral agent containing at least one compound represented by formulas (K6) to (K7) to develop an optically isotropic liquid crystal phase:

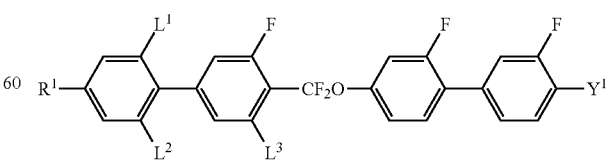

(1)

wherein, in formula (1), R$^1$ is hydrogen, alkyl having 1 to 12 carbons, alkenyl having 2 to 12 carbons, alkynyl having 2 to 12 carbons or alkoxy having 1 to 11 carbons; L¹ is fluorine, L² is hydrogen and L³ is fluorine; and Y¹ is fluorine, $CF_3$ or —$OCF_3$;

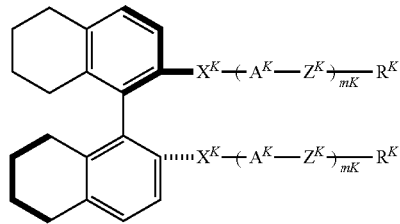
(K6)

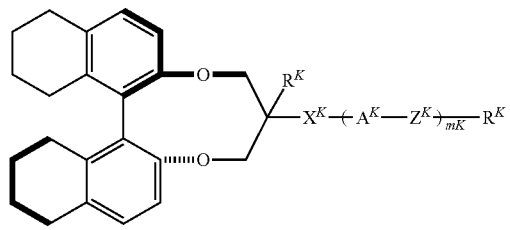
-continued
(K7)

wherein, in the formulas, $R^K$ is each independently hydrogen, halogen, —C≡N, —N=C=O, —N=C=S or alkyl having 1 to 12 carbons, at least one piece of —$CH_2$— in $R^K$ may be replaced by —O—, —S—, —COO— or —OCO—, at least one piece of —$CH_2$—$CH_2$— in $R^K$ may be replaced by —CH=CH—, —CF=CF— or and at least one piece of hydrogen in $R^K$ may be replaced by fluorine or chlorine;

$A^K$ is each independently an aromatic 6-membered to 8-membered ring, a non-aromatic 3-membered to 8-membered ring or a condensed ring having 9 or more carbons, and at least one piece of hydrogen of the rings may be replaced by halogen, alkyl or haloalkyl having 1 to 3 carbons, —$CH_2$— of the rings may be replaced by —O—, —S— or —NH—, and —CH= may be replaced by —N=;

$Z^K$ is each independently a single bond or alkylene having 1 to 8 carbons, at least one piece of —$CH_2$— in $Z^K$ may be replaced by —O—, —S—, —COO—, —OCO—, —CSO—, —OCS—, —CH=N— or —N=CH—, at least one piece of —$CH_2$—$CH_2$— in $Z^K$ may be replaced by —CH=CH—, —CF=CF— or and at least one piece of hydrogen of $Z^K$ may be replaced by halogen;

$X^K$ is each independently a single bond, —COO—, —OCO—, —$CH_2O$—, —$OCH_2$—, —$OCF_2$— or —$CH_2CH_2$—; and mK is each independently an integer from 1 to 3.

2. The liquid crystal composition according to claim 1, further containing at least one of compound (3) represented by formula (3) or compound (7) represented by formula (7) as a second component of the achiral component T:

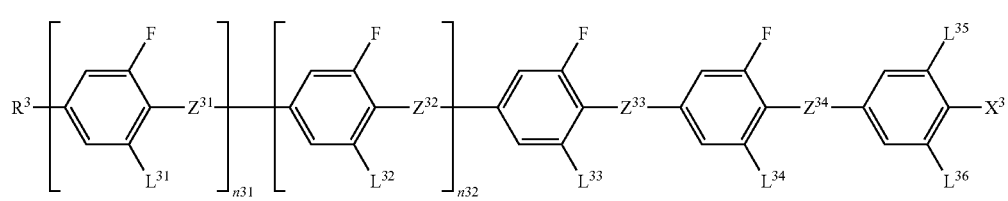
(3)

wherein, in formula (3), $R^3$ is hydrogen or alkyl having 1 to 12 carbons, at least one piece of —$CH_2$— in $R^3$ may be replaced by —O—, —S—, —COO— or —OCO—, at least one piece of —$CH_2$—$CH_2$— in $R^3$ may be replaced by —CH=CH—, —CF=CF— or —C≡C—, and at least one piece of hydrogen in $R^3$ may be replaced by fluorine or chlorine, however, in $R^3$, a case where —O— and —CH=CH— are adjacent is excluded, and a case where —CO— and —CH=CH— are adjacent is excluded;

$Z^{31}$, $Z^{32}$, $Z^{33}$ and $Z^{34}$ are each independently a single bond or alkylene having 1 to 4 carbons, and at least one piece of —$CH_2$— in the alkylene may be replaced by —O—, —COO— or —$CF_2O$—;

$L^{31}$, $L^{32}$, $L^{33}$, $L^{34}$, $L^{35}$ and $L^{36}$ are each independently hydrogen or fluorine;

$X^3$ is hydrogen, halogen, —$SF_5$ or alkyl having 1 to 10 carbons, at least one piece of —$CH_2$— in $X^3$ may be replaced by —O—, —S—, —COO— or —OCO—, at least one piece of —$CH_2$—$CH_2$— in $X^3$ may be replaced by —CH=CH—, —CF=CF— or —C≡C—, and at least one piece of hydrogen in $X^3$ may be replaced by fluorine or chlorine, however, in $X^3$, a case where —O— and —CH=CH— are adjacent is excluded, and a case where —CO— and —CH=CH— are adjacent is excluded;

n31 and n32 are each independently 0 or 1;

however, when n31+n32=1 and $Z^{33}$ is $CF_2O$, both $L^{35}$ and $L^{36}$ are fluorine;

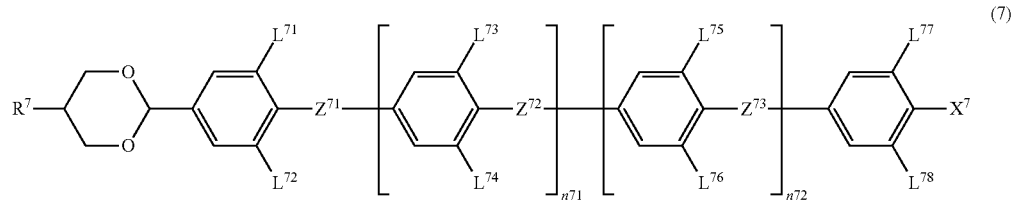
(7)

wherein, in formula (7), $R^7$ is hydrogen or alkyl having 1 to 12 carbons, at least one piece of —$CH_2$— in $R^7$ may be replaced by —O—, —S—, —COO— or —OCO—, at least one piece of —$CH_2$—$CH_2$— in $R^7$ may be replaced by —CH=CH—, —CF=CF— or —C≡C—, and at least one piece of hydrogen in $R^7$ may be replaced by fluorine or chlorine, however, in $R^7$, a case where —O— and —CH=CH— are adjacent is excluded, and a case where —CO— and —CH=CH— are adjacent is excluded;

$L^{71}$, $L^{72}$, $L^{73}$, $L^{74}$, $L^{75}$, $L^{76}$, $L^{77}$ and $L^{78}$ are each independently hydrogen or fluorine;

$Z^{71}$, $Z^{72}$ and $Z^{73}$ are each independently a single bond, —COO— or —$CF_2O$—;

n71 and n72 are each independently 0 or 1; and $X^7$ is hydrogen, halogen, —$SF_5$ or alkyl having 1 to 10 carbons, at least one piece of —$CH_2$— in $X^7$ may be replaced by —O—, —S—, —COO— or —OCO—, at least one piece of —$CH_2$—$CH_2$— in $X^7$ may be replaced by —CH=CH—, —CF=CF— or —C≡C—, at least one piece of hydrogen in $X^7$ may be replaced by fluorine or chlorine, however, in $X^7$, a case where —O— and —CH=CH— are adjacent is excluded, and a case where —CO— and —CH=CH— are adjacent is excluded.

3. The liquid crystal composition according to claim 2, wherein compound (3) is a compound represented by any one of formula (3-2) or (3-3):

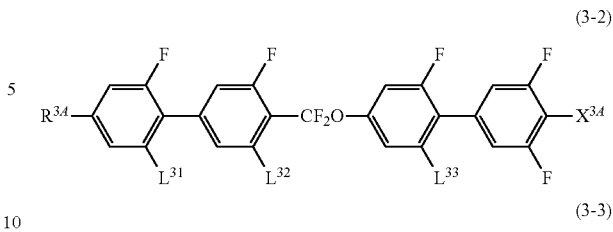

(3-2)

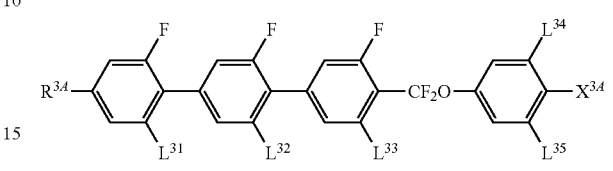

(3-3)

wherein, in the formulas, $R^{3A}$ is each independently alkyl having 1 to 12 carbons, alkenyl having 2 to 12 carbons or alkoxy having 1 to 11 carbons;

$L^{31}$, $L^{32}$, $L^{33}$, $L^{34}$ and $L^{35}$ are each independently hydrogen or fluorine; and $X^{3A}$ is fluorine, chlorine, —$CF_3$ or —$OCF_3$.

4. The liquid crystal composition according to claim 2, wherein compound (7) is a compound represented by any one of formulas (7-1) to (7-8):

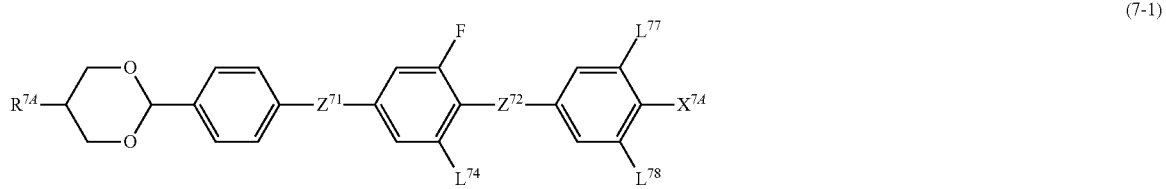

(7-1)

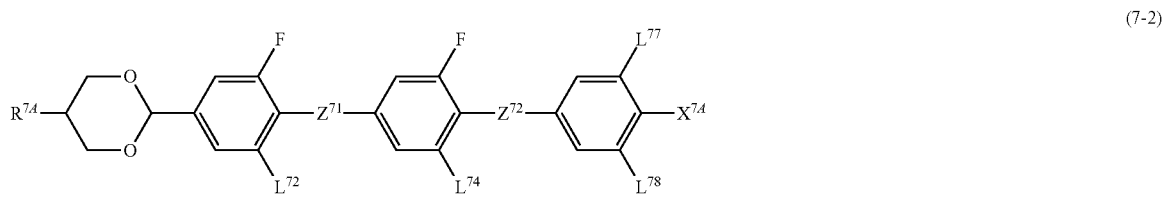

(7-2)

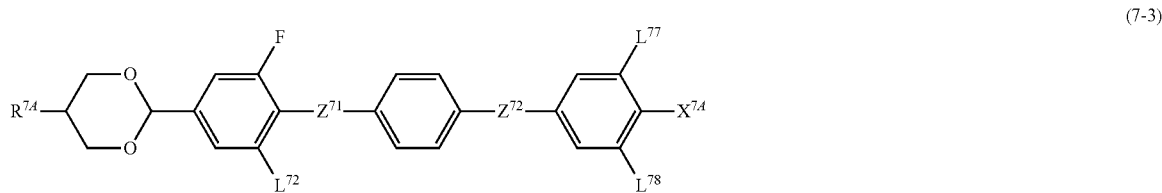

(7-3)

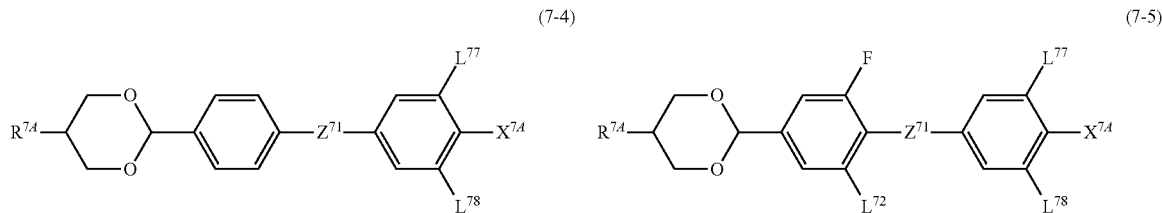

(7-4)                                                      (7-5)

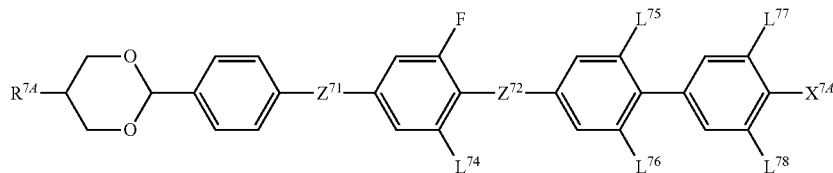
(7-6)

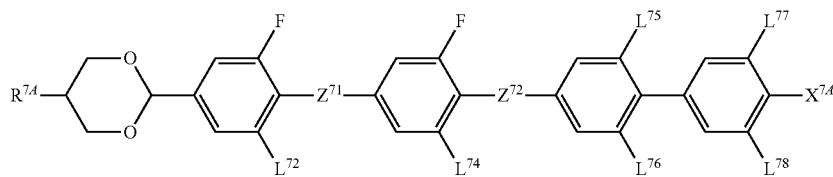
(7-7)

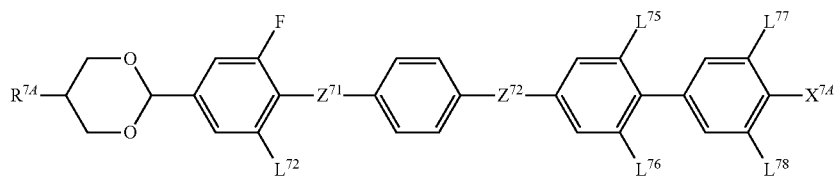
(7-8)

wherein, in the formulas, $R^{74}$ is each independently hydrogen, alkyl having 1 to 12 carbons or alkenyl having 2 to 12 carbons or alkoxy having 1 to 11 carbons;

$L^{72}$, $L^{74}$, $L^{75}$, $L^{76}$, $L^{77}$ and $L^{78}$ are each independently hydrogen or fluorine;

$X^{74}$ is each independently fluorine, chlorine, —$CF_3$ or —$OCF_3$, and $Z^{71}$ and $Z^{72}$ are each independently a single bond, —COO— or —$CF_2O$—, but at least one thereof is —COO— or —$CF_2O$—.

5. The liquid crystal composition according to claim 2, wherein compound (7) is a compound represented by any one of formulas (7-2-2-E), (7-2-5-E), (7-2-7-E), (7-2-2-F), (7-2-5-F), (7-2-6-F) or (7-2-7-F):

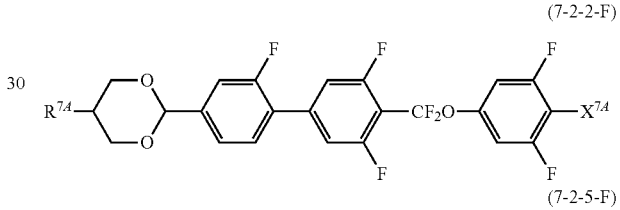
(7-2-2-E)

(7-2-5-E)

(7-2-7-E)

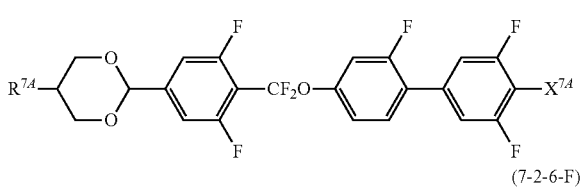
(7-2-2-F)

(7-2-5-F)

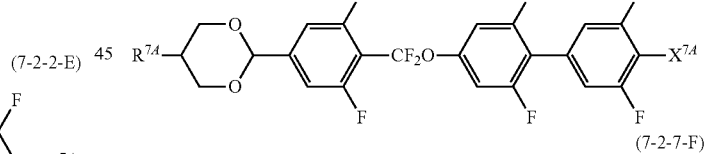
(7-2-6-F)

(7-2-7-F)

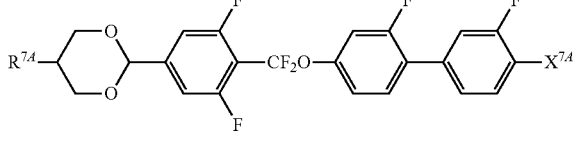

wherein, in the formulas, $R^{74}$ is each independently alkyl having 1 to 12 carbons, alkenyl having 2 to 12 carbons or alkoxy having 1 to 11 carbons; and $X^{74}$ is fluorine, chlorine, —$CF_3$ or —$OCF_3$.

6. The liquid crystal composition according to claim 2, containing 20% by weight to 60% by weight of compound (3) in total or 30% by weight to 70% by weight of compound (7) in total, in addition to 10% by weight to 30% by weight of compound (1) in total, based on the total weight of the achiral component T.

7. The liquid crystal composition according to claim 1, further containing at least one of compound (4) represented by formula (4) and compound (2) represented by formula (2) as a third component of the achiral component T;

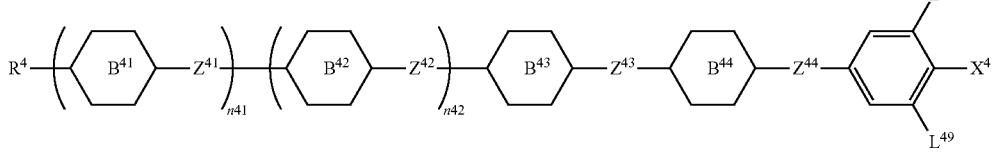

(4)

wherein, in formula (4), $R^4$ is alkyl having 1 to 12 carbons, alkenyl having 2 to 12 carbons or alkoxy having 1 to 11 carbons;
$B^{41}$, $B^{42}$, $B^{43}$, and $B^{44}$ are each independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine 2,5-diyl;
$Z^{41}$, $Z^{42}$, $Z^{43}$ and $Z^{44}$ are each independently a single bond, ethylene, —COO—, —OCO—, —CF$_2$O— or —OCF$_2$—;
$L^{48}$ and $L^{49}$ are each independently hydrogen or fluorine;
$X^4$ is fluorine, chlorine, —CF$_3$ or —OCF$_3$;
n41 and n42 are each independently 0 or 1;
however, a case where all of $B^{41}$, $B^{42}$, $B^{43}$ and $B^{44}$ are 1,4-phenylene replaced by fluorine is excluded; and when n41+n42=1 and $Z^{43}$ is —CF$_2$O—, both $L^{48}$ and $L^{49}$ are fluorine;

however, in $R^2$, a case where —O— and —CH=CH— are adjacent is exclude, and a case where —CO— and —CH=CH— are adjacent is excluded;

$A^{21}$, $A^{22}$, $A^{23}$, $A^{24}$ and $A^{25}$ are each independently 1,4-cyclohexylene, 1,3-dioxane-2,5-diyl, 1,4-phenylene, 1,4-phenylene in which one or two pieces of hydrogen are replaced by fluorine, 1,4-phenylene in which two pieces of hydrogen are each replaced by fluorine and chlorine, pyridine-2,5-diyl or pyrimidine-2,5-diyl;
$Z^{21}$, $Z^{22}$, $Z^{23}$, $Z^{24}$, $Z^{25}$ and $Z^{26}$ are each independently a single bond or alkylene having 1 to 4 carbons, and at least one piece of —CH$_2$— in the alkylene may be replaced by —O—, —COO— or —CF$_2$O—;
$L^{21}$, $L^{22}$ and $L^{23}$ are each independently hydrogen or fluorine;
$X^2$ is fluorine, chlorine, —CF$_3$ or —OCF$_3$;
n21, n22, n23, n24 and n25 are each independently 0 or 1, and an expression: $2 \leq n21+n22+n23+n24+n25 \leq 3$ holds,

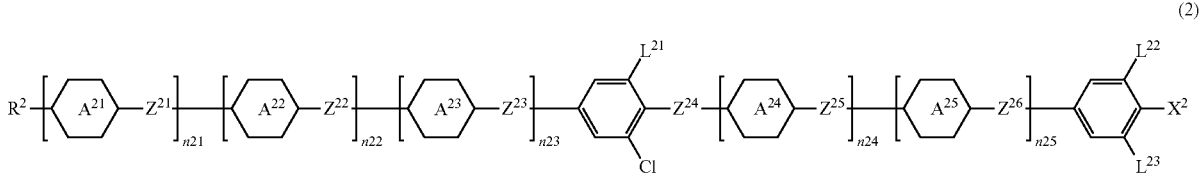

(2)

wherein, in formula (2), $R^2$ is hydrogen or alkyl having 1 to 12 carbons, at least one piece of —CH$_2$— in $R^2$ may be replaced by —O—, —S—, —COO—, —OCO—, —CH=CH—, —CF=CF— or —C≡C—, and at least one piece of hydrogen in $R^2$ may be replaced by halogen or alkyl having 1 to 3 carbons;

however, when n21+n22+n23+n24+n25=2, both $L^{22}$ and $L^{23}$ are fluorine.

8. The liquid crystal composition according to claim 7, wherein compound (4) is a compound represented by any one of formulas (4-1) to (4-9):

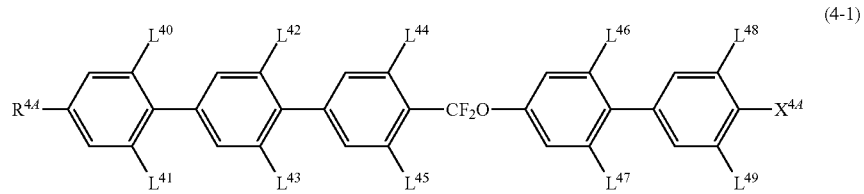

(4-1)

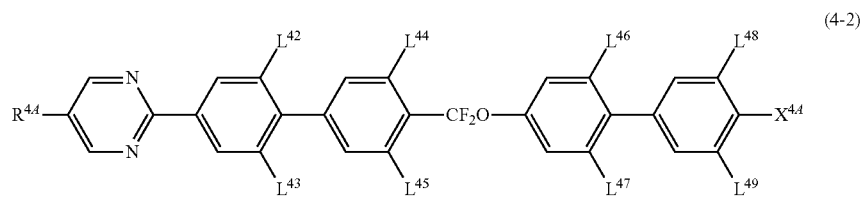

(4-2)

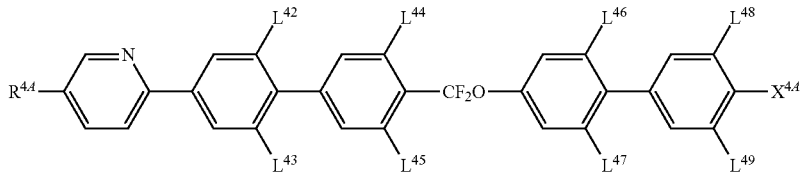
(4-3)
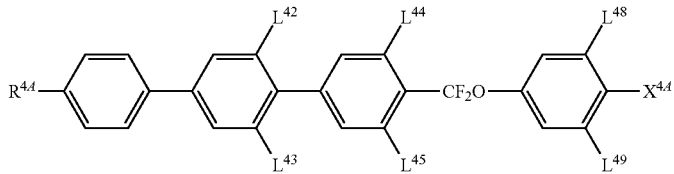
(4-4)
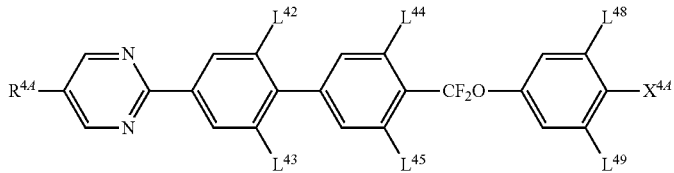
(4-5)
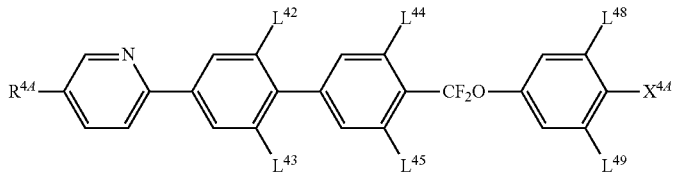
(4-6)
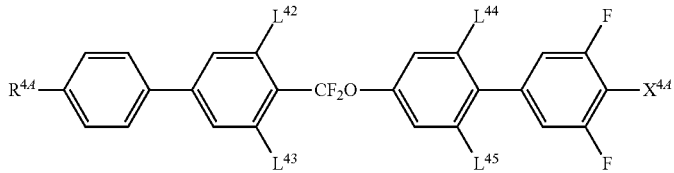
(4-7)
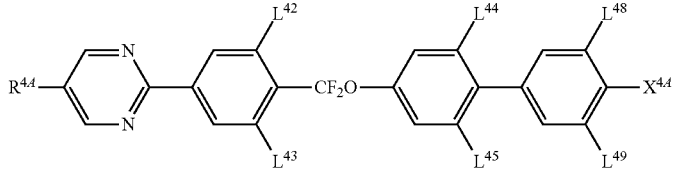
(4-8)
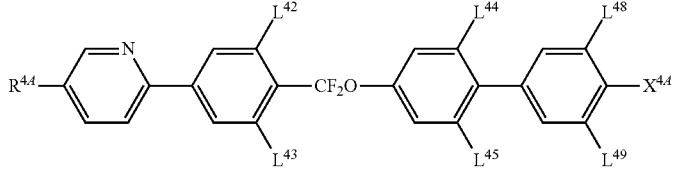
(4-9)
wherein, in the formulas, $R^{4A}$ is each independently alkyl having 1 to 12 carbons, alkenyl having 2 to 12 carbons or alkoxy having 1 to 11 carbons; $X^{4A}$ is fluorine, chlorine, —$CF_3$ or —$OCF_3$; and $L^{40}$ to $L^{49}$ are each independently hydrogen or fluorine.
9. The liquid crystal composition according to claim 7, wherein compound (2) is a compound represented by any one of formulas (2-1-1-2), (2-1-2-1), (2-1-3-1), (2-1-3-2), (2-1-4-2) or (2-1-4-3):

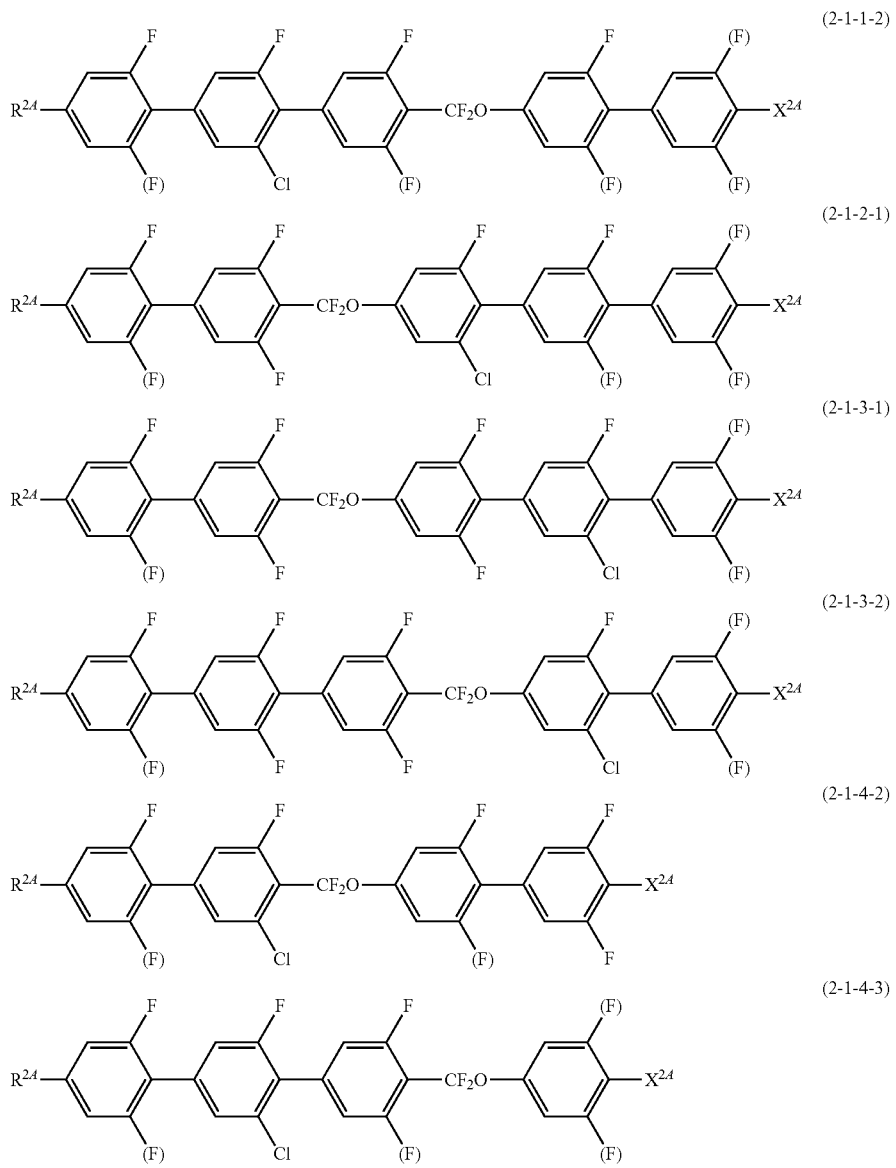

wherein, in the formulas, $R^{2A}$ is each independently alkyl having 1 to 12 carbons, alkenyl having 2 to 12 carbons or alkoxy having 1 to 11 carbons;

(F) is each independently hydrogen or fluorine; and $X^{2A}$ is fluorine chlorine —$CF_3$ or —$OCF_3$.

10. The liquid crystal composition according to claim 1, exhibiting a chiral nematic phase at any temperature in a temperature range from −20° C. to 70° C., and having 700 nanometers or less in a helical pitch in at least part of the temperature range.

11. A mixture, containing the liquid crystal composition according to claim 1 and a polymerizable monomer.

12. A composite material of polymer and liquid crystal, obtained by polymerizing the mixture according to claim 11 and used for a device driven by an optically isotropic liquid crystal phase.

* * * * *